(12) United States Patent
Hayward et al.

(10) Patent No.: US 6,264,958 B1
(45) Date of Patent: Jul. 24, 2001

(54) GENES OF KAPOSI'S SARCOMA ASSOCIATED HERPESVIRUS

(75) Inventors: Gary S. Hayward, Baltimore; John Nicholas, Towson; Marvin R. Reitz, Derwood; J. Marie Hardwick, Baltimore, all of MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/230,637
(22) PCT Filed: Jul. 24, 1997
(86) PCT No.: PCT/US97/12931
§ 371 Date: Nov. 23, 1999
§ 102(e) Date: Nov. 23, 1999
(87) PCT Pub. No.: WO98/04284
PCT Pub. Date: Feb. 5, 1998

Related U.S. Application Data

(60) Provisional application No. 60/022,591, filed on Jun. 25, 1996.

(51) Int. Cl.[7] .................... A61K 39/245; A61K 39/12; C12P 19/34
(52) U.S. Cl. ................... 424/229.1; 424/204.1; 435/91.33; 435/91.1; 514/44; 530/300; 530/324; 536/23.72
(58) Field of Search ............... 424/204.1, 229.1; 435/91.33, 91.1; 514/44; 530/300, 324; 536/23.72

(56) References Cited

U.S. PATENT DOCUMENTS

| | | |
|---|---|---|
| 5,801,042 | 9/1998 | Chang et al. . |
| 5,830,759 | 11/1998 | Chang et al. . |
| 5,849,564 * | 12/1998 | Chang et al. ............ 435/252.3 |
| 5,854,398 | 12/1998 | Chang et al. . |
| 5,861,500 | 1/1999 | Chang et al. . |

OTHER PUBLICATIONS

Russo et al . PNAS USA, Dec. 1996, vol. 93, pp. 14862–14876.*
Boshoff et al. Nature Medicine, Dec. 1995, vol. 1, No. 12, pp. 1274–1278.*
Zhong et al. PNAS USA, vol. 93, pp.6641–6646, Jun. 1996.*
Moore et al. "primary Characterization of a Herpesvirus Agent Associated with Kaposi's Sarcoma" Journal of Virology, Jan. 1996, vol. 70, No. 1, pp. 549–558.
Chang et al. "Identification of Herpesvirus–Like DNA Sequences in AIDS–Associated Kaposi's Sarcoma" Science Dec. 16, 1994, vol. 266, pp. 1865–1869.

* cited by examiner

Primary Examiner—Ali R. Salimi
(74) Attorney, Agent, or Firm—Banner & Witcoff, Ltd.

(57) ABSTRACT

A human gamma herpesviris genome known as Kaposi sarcoma associated herpesvirus (KSHV) or human herpesvirus 8 (HHV-8) is present in virtually all AIDS and non-AIDS Kaposi's sarcoma (KS) lesions, as well as in body cavity based lymphomas (BCBL), Multiple myeloma, and in multicentric Casdeman's disease. Isolation and DNA sequencing of a 17-kb segment encompassing a HHV-8 divergent locus (DL-B) between ORF11 and ORF17 revealed the presence of nine viral ORFs with gene products related to cellular proteins. These include the complete thymidylate synthase (TS) gene and a dihydrofolate reductase (DHFR) gene, four cytokine genes (vIL6, vMIP-1A, vMIP-1B and BCK) that have not previously been found to be encoded by a virus, and a Bcl2 homologue. This region in HHV-8 also contains the T1.1 abundant lytic cycle nuclear RNA gene and encompasses two genes (or exons) encoding proteins with C4HC3 zinc finger domains of the PHD/LAP subtype. The latter are related to the spliced immediatelady IE1 protein of the bovine gamma-2 class herpesvirus BHV-4 and a similar motif found in HVS ORF12. Transcripts form the IE-1A, IE-1B, DHFR, and MIP-1B genes were all detected by Northern blot hybridization analysis in a BCBL cell line at 12-h after induction with butyrate, but were not present before induction, indicating that these are all primarily lytic cycle genes.

10 Claims, 16 Drawing Sheets

THYMIDYLATE SYNTHETASE (TS)

```
        1                                                             50
HHV-8   MFPFVPLSLY VAKKLFRARG FRFCQKPGVL ALAPEVDPCS IQHEVTGAET
HVS     .......... .......... .......... .......... ...MSTHTEE
HVA     .......... .......... .......... .......... .......MEE
VZV     .......... .......... .......... .......MGDL SCWTKVPGFT
Human   .......... .......... .....PVAGS ELPRRPLPPA AQERDAEPRP 51                                                            100
HHV-8   PHEELQYLRQ LREILCRGSD RLDRTGIGTL SLFGMQARYS LRDHFPLLTT
HVS     QHGEHQYLSQ VQHILNYGSF KNDRTGTGTL SIFGTQSRFS LENEFPLLTT
HVA     LHAEHQYLSQ VKHILNCGNF KHDRTGVGTL SVFGMQSRYS LEKDFPLLTT
VZV     LTGELQYLKQ VDDILRYGVR KRDRTGIGTL SLFGMQARYN LRNEFPLLTT
Human   PHPELQYLGQ IQHILRCGVR KDDRTGTGTL SVFGMQARYS LRDEFPLLTT 101                                                           151
HHV-8   KRVFWRGMVQ ELLWFLKGST DSRELSRTGV KIWDKNGSRE FLAGFGLAHR
HVS     KRVFWRGMVE ELLWFIRGST DSKELSAAGV HIWDANGSRS FLDKLGFYDR
HVA     KRVFWRGMVE ELLWFIRGST DSKELAASGV HIWDANGSRS YLDKLGLFDR
VZV     KRVFWRAMVE ELLWFIRGST DSKELAAKDI HIWDIYGSSK FLNRNGFHKR
Human   KRVFWKGVLE ELLWFIKGST NAKELSSKGV KIWDANGSRD FLDSLGFSTR 151                                                           200
HHV-8   REGDLGPBYG FQWRHFGAAY VDADADYTGQ GFDQLSYIVD LIKNNPHDRR
HVS     DEGDLGPVYG FQWRHFGAEY KGVGRLYKGE GMDQLKQLID TIKTNPTDRR
HVA     EEGDLGPVYG FQWRHFGAEY QGLKHNYGGE GMDQLKQIIN TIHTNPTDRR
VZV     HTGDLGPIYG FQWRHFGAEY KDCQSNYLQQ GIDQLQTVID TIKTNPESRR
Human   EEGDLGPVYG FQWRHFGAEY RDMESDYSGQ GMDQLQRVID TIKTNPDDRR 201                                                           250
HHV-8   IIMCAWNPAD LSLMALPPCH LLCGFYVADG ELSCQLYQRS GDMGLGVPFN
HVS     MLMCAWNVSD IPKMMLPPCH VLSQFYVCDG KLSCQLYQRS ADMGLGVPFN
HVA     MLMCAWNVLD VPKMALPPCH VLSQFYVCDG KLSCQLYQRS ADMGLGVPFN
VZV     MIISSWNPKD IPLMMLPPCH TLQQFYVANG ELSCQVYQRS GDMGLGVPFN
Human   IIMCAWNPRD LPLMALPPCH ALCQFYVVNS ELSCQLYQRS GDMGLGVPFN 251                                                           300
HHV-8   IASYSLLTYM LAHMTGLRPG EFIHTLGDAH IYKTHIEPLR LQLTRTPRPF
HVS     IASYSLLTCM IAHVTNLVPG EFIHTIGDAH IYVDHIDALK MQLTRTPRPF
HVA     IASYSLLTCM LAHVTLLVPG EFIHTLGDAH VYVNHVDALT EQLTRTPRPF
VZV     IAGYALLTYI VAHMTGLKTG DLIHTMGDAH IYLNHIDALK VQLARSPKPF
Human   IASYALLTYM IAHTTGLKPG DFIHTLGDAH IYLNHIEPLK IQLQREPRPF 301
HHV-8   PRLEILRSVS SMEEFTPDDF RLVDYCPHPT IRMEMAV
HVS     PTLRFARNVS CIDDFKADDI ILENYNPHPI IKMHMAV
HVA     PTLKFARKVA SIDDFKANDI ILENYNPYPS IKMPMAV
VZV     PCLKILRNVT DINDFKWDDF QLDGYNPHPP LKMEMAL
Human   PKLRILRKME KIDDFKAEDF QIEGYNPHPT IKMEMAV
```

FIG. 5A

DIHYDROFOLATE REDUCTASE (DHFR)

```
                    1                                                              50
HHV-8       MDPTLYCVVA VDTKLGIGKN RCLPWPALRG DMRRFRQLIT DCAVPGKQNM
HVS         MVQALNCIVA VAQNMGIGKQ GNLPWPRLMN DFKHFQRMTT TSSVPDKQNL
Human       .VGSLNCIVA VSQNMGIGKN GDLPWPPLRN EFRYFQRMTT TSSVEGKQNL
Pig         .VRPLNCIVA VSQNMGIGKN GDLPWPPLRN EYKYFQRMTT TSSVEGKQNL
Drosophila  .MLRFNLIVA VCENFGIGIR GDLPW.RIKS ELKYFSRTTK RTSDPTKQNA 51                                                             100
HHV-8       VMMGRRTWLS IPAGCRPLAG RINVVLSRTL ETPP.PGAHF LASSLDAALG
HVS         VIMGKKIWFS IPEKNRPLKG RINVVLSKEL KELP.HRAHF LAKSLDDALK
Human       VIMGKKTWFS IPEKNRPLKG RINLVLSREL KEPP.QGAHF LSRSLDDALK
Pig         VIMGRKIWFS IPEKNRPLKD RINIVLSREL KEPP.QGAHF LAKSLDDALK
Drosophila  VMMGRKTYFG VPESKRPLPD RLNIVLSTTL QESDLPKGVL LCPNLETAMK 101                                                             150
HHV-8       LARSPELAQQ IDKVWVIGGG DLYREALTGP WPVRLFLTRV LHDFACDMFL
HVS         LTEQPELANK VDMVWIIGGS SVYKEAMSYP CDLKLFVTRI MQDFECDTFF
Human       LTEQPELANK VDMVWIVGGS SVYKEAMNHP GHLKLFVTRI MQDFESDTFF
Pig         LTEQPELKDK VDMVWIVGGS SVYKEAMNKP GHIRLFVTRI KMEFESDTFF
Drosophila  ILEEQ...NE VENIWIVGGS GVYEEAMASP RCHRLYITQI MQKFDCDTFF 151                                                             200
HHV-8       SHDSLAAYAR VNPKPGEQER VFQERGIFYM FETYIKVTQS SDTALPDLER
HVS         PEFDLEKYKL LIEYPSVLSN VQEEKSIKYK FEVYEKNH
Human       PEIDLEKYKL LPEYPGVLSD VQEEKGIKYK FEVYEKND
Pig         PEIDLEKYKL LSECSGVPSD VQEEKGIKYK FEVYEKNN
Drosophila  PAIP.DSFRE VAPDSDMPLG VQEENGIKFE YKILEKHS

201
HHV-8       PRPATPPFSE TS
```

```
           *  *              *  *        * *
 1  MASKDVEEGVEGPICWICREEVGNEGIHPCACTGELDVVHPQCLSTWLTV  50
    |   ||| ||   | ||||  || ||  |||  ||||||    |||||||  |
 1  M...EDED.V..PMCWICNEELGNERFRACGCTGELENVHRSCLSTWLTI  44
        * *
51  SRNTACQMCRVIYRTRTQWRS..RLNLWREMERQEIFELFLLMSVVVAGL  98
    |||||||  |  |  ||  ||      ||   ||||  |||    ||  |
45  SRNTACQICGVMYNTRVVWRPLREMTLLRRLTYQEGLELIVFIFIMTLGA  94

99  VGVALCTWTLLVILTAPAGTFSPGAVLGFLCFFGFYQIFIVFAFGGICRV  148
    | |    |  | |                |      |  |    ||
95  AGLAAATWWLYIVGGHDPEIDHVAAAAYYVFFVFYQLFVVFGLGAFFHM  144

149 SGTVRALYAANNTRVTVLPYR.RPRRPTANEDNIELTVLVGPAGGTDEEP  197
            |           |   || ||
145 MRHVGRAYAAMNTRVEVFPYRPRPTSPECAVEEIELQEILPRGDNQDEEG  194

198 TDESSEGDVASGDKERDGSSGDEPDGGPNDRAGLRGTARTDLCAPTKKPV  247
         |      |    |  ||                |
195 PAGAAPGDQNGPAGAAPGDQDGPADGAPVHRDSEESVDEAAGYKEAGEPT  244

248 RKNHPKNNG  256
    | |    |
245 HNDGRDDNVEPTAVGCDCNNLGAERYRATYCGGYVGAQSGDGAYSVSCHN  294

295 KAGPSSLVDILPQGLPGGGYGSMGVIRKRSAVSSALMFH  333
```

FIG. 6A

B BCK

```
HV8bck    MWSMCWV.LR AHLGLLFWVA VIELCAASGP ATIMASDCCE NSLSSARLPP
HV8MIP1a  MAPVHV..LC CVSVLLATPY LTPTESAGSL VSYTPNSCCY .GFQQ.HPPP
HV8MIP1b  M.DTKGI.LL VAVLT.ALLC LQSGDTLGAS W.HRPDKCCL .GYQK.RPLP
HuMIP1a   MQVSTSS.LA VLLCTMALCN QV...LSAPL AADTPTACCF .SYTS.RQIP
HuRANT    MKVSAAR.LA VILIATALCA PA...SAS.PY SSDT.TPCCF .AYI.ARPLP
Hutac2    MKLCVTV.LS .LLMLVAAFC SP...ALSAPM GSDPPTACCF .SYT.ARKLP
Mumcp1    MQVPVML.LG .LLFTVAGWS IH..VLSQRD AVNAPLTCCY .SFTS.KMIP
Ramcp1    MQVSVTL.LG .LLFTVAACS IH..VLSQRD AVNAPLTCCY .SFTG.KMIP
Hucc      MKVSAAL.IW .LLLIAAAFS PQ...GLTGPA SV...PTTCCF N.LAN.RKIP
```

```
                          *                   *
HV8bck    DKLICGWYW. .TSTVYCRQK AMIFVTHSGR KVCGSPAKRR TRLLMEKHTE
HV8MIP1a  VQILKEWYP. .TS.PACPKP GMILLTKRGR QICADPSKNW VRQLMQRLPA
HV8MIP1b  QVLLSSWYP. .TS.QLCSKP GMIFLTKRGR QVCADKSKDW VKKLMQQLPV
HuMIP1a   .QNFIADYFE .TS.SQCSKP SMIFLTKRGR QVCADPSEEW VQKYVSDLEL
HuRANT    .RAHIKEYFY .TS.GKCSNP AMVPVTRKNR QVCANPEKKW VREYINSLE
Hutac2    .RNFVVDYYE .TS.SLCSQP AMVFQTKRGK QVCADPSESW VQEYVYLLEL
Mumcp1    .MSRLESYKR ITS.SRCPKE AMFVTKLKR EVCADPKKEW VQTYIKNLDR
Ramcp1    .MSRLENYKR ITS.SPCPKE AMMFVTKLKR EICADONKEW VQKYIRKLDQ
Hucc      .LQRLESYRR ITS.PKCPQK AMIFRTKLAK DICADQKKRW VQDSMKYLDQ
```

```
HV8bck    IPLAKRVALR AGKGLCP
HV8MIP1a  IA
HV8MIP1b  TAR
HuMIP1a   SA
HuRANT    S
Hutac2    N
Mumcp1    NQMRSEPTTLFK TASALRSSAP LNVKLTRKSE ANASTTFSTT TSSTSVGVTS
Ramcp1    NQVRSETTVFKY IASTLRTSAP LNVNLTHKSE ANASTLFSTT TSSTSVEVTS
Hucc      KSPTPKP
```

```
Mumcp1    VTVN
Ramcp1    MTEN
```

FIG. 6B

C VIL-6

```
         1                                                                    50
vIL-6   MCWFKLWSL. ...LLCGSLL VSGTRGKLPD APEFE..... ..........K
Human   MNSFSTSAFG PVAFSLGLLL VLPAAFPAPV PPGEDSKDVA APHRQPLTSS 51                       *         *                               100
vIL-6   DLLIQRLNWM LWVIDECFRD LCYRTGICKG ILEPAAIFHL KLPAINDTDH
Human   ERIDKQIRYI LQGISALRKE TCNKSNMCES SKEALAENNL NLPKMAEKDG

*              *                                                  150
vIL-6   CGLIGFNETS CLRKLADGFF EFEVLFKFLT TEFGKSVINV DVMELLTKTL
Human   CFQSGFNEET CLVKIITGLL EFEVYLEYLQ NRFESSEEQA RAVQMSTKVL 151                                                                200
vIL-6   GWDIQEELNK LTKTHYSPPK FDRGLLGRLQ GLKYWVRHFA SFYVLSAMEK
Human   IQFLQKKAKN LDAITTPDPT TNASLLTKLQ AQNQWLQDMT THLILRSFKE 201
vIL-6   FAGQAVRMLD SIPDVTPDVH DK
Human   FLQSSLRALR QM
```

FIG. 6C

BKS Sublcass of PHD/LAP Finger Motifs                                    C4HC3

```
                    2 x Zn
            ┌─────────────────────────────────────┐
           CWIC         C C  f     H Cf  Wf          C fC        Y
           CX2C         CXC X4-7   HX2C             CX2C
CRZYS1A    EDSCWICLAGAE----SGLRPCRCPRSV---HLSCLGRWQLQQAGRS----EEQRCRFCRCG
M110.3     EKYCKFCPGTESDNALSFVHPCRCRGSIHWVHHQCLAMWFSKANAVQ-----QVMCIQCQTRYQ
YSSM4      GATCRICRGEATEDN-PLPHPCRCRGSIKYMHESCLLEWVASKNIDISKPGADVKCDICHYPIQ
D2089.2    TVUCRICFDNDTSSD-SLIKPCSCSGTVAYVHNGCLEQWVRTTSNID--------CTICQDMFE
F58E6.1    RRICRICQMHEGD----MVRPCDCAGTMGDVHEECLTKWVNMSNKKT--------CEICKSEYT
SWPOX      MDPVCWICKDDYSIEK----NYCNCKNEYKVVHDECMKKWIQYSRERS--------CKLCNKEYN
HHV8IE1B   VPVCWICNEELGNER---FRACGCTGELENVHRSCLSTWLTISRNTA--------CQICGVVYN
HHV8IE1A   GPICWTCREEYGNEG---IHPCACTGELDVVHPQCLSTWLTVSRNTA--------CQNCRVIYR
BHV4IE1B   YAECWICKGSEGIID---VKYCHCIGDLQYVHSECLVHWIRVSGTKQ--------CKFCQYTYI
BHV4IE1A   GKQCWICRDGESLPE---ARYCNCYGPLQYCHEECLKTWISMSGEKK--------CKFCGTOYK
HVSORF12   QKKCLICCNIGEEEL---LQACDCPSRV---HHTCLQSHIQCFKSSM--------CTFCEKKYK
```

FIG. 7A

OTHER PHD/LAP Class Motifs                                               C4HC3

```
           C fC          Ff  C      fH Cf              W C  C
           CX2C          CX2-4C X4  HX2C               CX2C
HUMAF10    IGGCGVCSDERGWAENP-LVYCDGHGCSVAVHGACYGIVQVP--------TGPWFCRKCESQ
HUMMLLa    RVVCFLCASSGNVE----FVYCQV--CCEPFHKFCLEENERF----LEDQLENWCRRCRFC
```

FIG. 7B

Ring Finger Motifs                                                       C3HC4

```
                    Zn(I)              Zn(II)
            ┌────────────────┬───────────────────┐
           C  C              C H FC Cf            CP C
           CX2C              CXHX2CX2C            CX2C
           β-Sheet           β-Sheet    α-Helix   β-Sheet
RAG-1      SISCQICEHILADPV--ET------NCKHVFCRVCILRCLK-VMGS--------YCPSCRYPCF
HSVICP0    GDVCAVCTDEIAPHLRCDT-----FPCMHRFCIPCM-KTWNQLRNT--------CPLCNAKLV
PML        FLRCQQCQAEAKCP-KL-------LPCLHTLCSGCLEASGM------------QCPICQAPWP
BRCA1      ILECFICLELIKEFVST-------KCDHIFCKFCMLKLLNQKKGPS-------QCPLCKNDIT
```

FIG. 7C

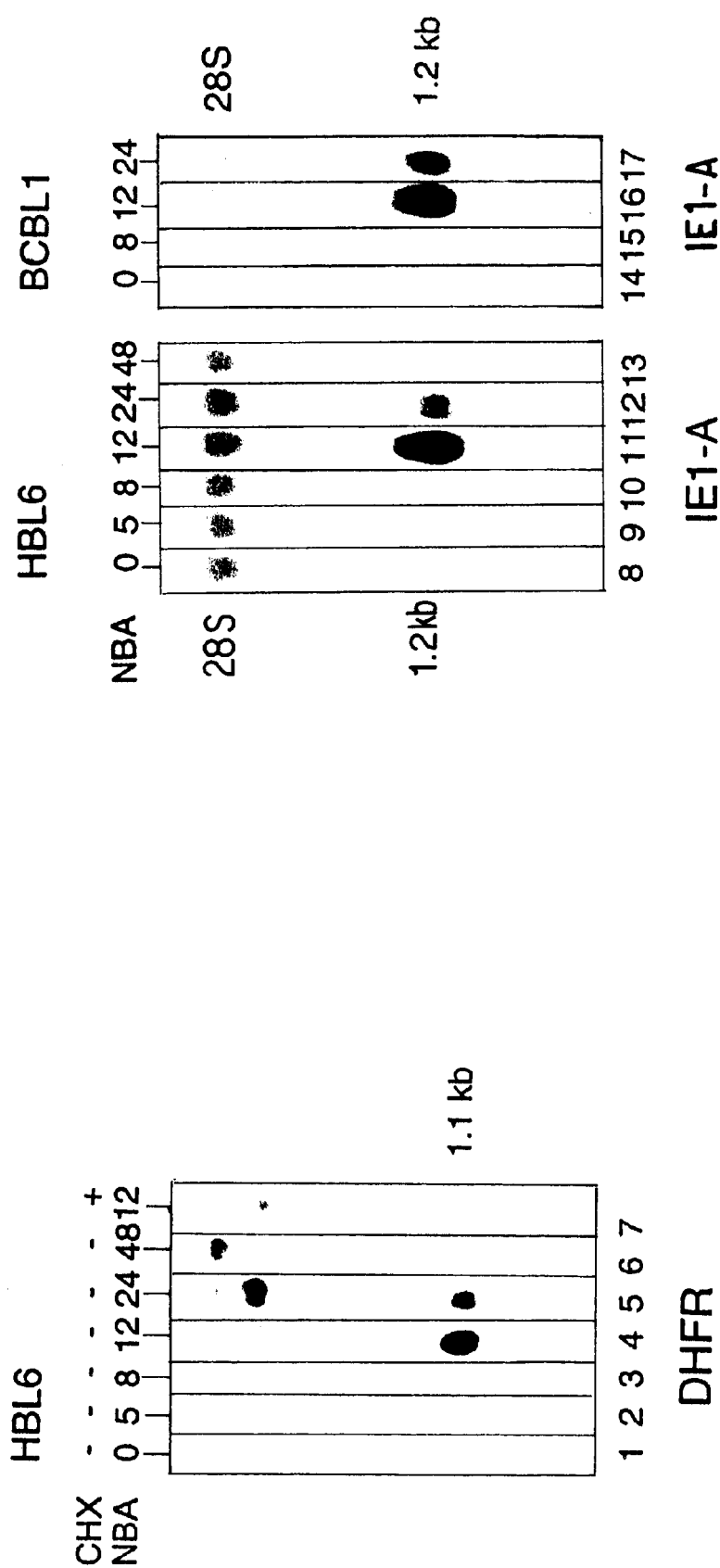

GENES OF KAPOSI'S SARCOMA ASSOCIATED HERPESVIRUS

This application claims the benefit of provisional application Ser. No. 60/022,591, filed Jun. 25, 1996.

The U.S. Government has a paid-up license in this invention and the right in limited circumstances to require the patent owner to license others on reasonable terms as provided for by the terms of grants awarded by the National Institutes of Health U01 CA37314, R01 CA73585, and P30 CA06973.

TECHNICAL FIELD OF THE INVENTION

This invention is related to the field of virology, in particular to the area of herpes viruses. More particularly the invention relates to the diagnosis of a herpes virus associated with human diseases.

BACKGROUND OF THE INVENTION

Kaposi's Sarcoma (KS) is the most frequent neoplastic complication seen in patients who are infected with HIV and is especially prevalent in male homosexual AIDS patients (26, 66). It is generally thought to be associated with a sexually and blood borne agent that is transmitted independently of HIV (10). A large proportion of Kaposi's sarcoma (KS) lesions, from both HIV-associated AIDS patients and from non-HIV associated classical and endemic sources, have been found to contain two small DNA fragments representing sequences from a putative novel gamma class herpesvirus genome referred to as KSHV or human herpesvirus-8 (HHV-8) (6, 19, 45). Several additional rare lymphomas, including multicentric Castleman's Disease and Body Cavity Based Large Cell lymphomas (BCBL), but few other tumor or normal tissue samples contain these same DNA sequences (16–18, 57). Additional recent evidence has shown that these sequences are part of a large episomal viral genome in BCBL cell lines (46, 52), that HHV-8 DNA positive BCBL cell lines can be induced to produce herpesvirus-like particles (52), and that sera from most patients with KS (but not normal sera) have antibodies to HHV-8 proteins (30, 37). In addition, evidence has been found that HHV-8 is also associated with Multiple myeloma. (Rettig et al., Science 276:1851–1854, 1997.) Together, these results suggest the strong likelihood that this proposed new infectious virus may be the etiological agent of KS (13, 44, 46, 52).

The two small DNA segments found in the original KS lesion studied (19) represent parts of the genes encoding the ORF25 major capsid, the ORF26 minor capsid protein and the ORF75 protein, based on the nomenclature used for the most closely related gamma herpesvirus HVS. The proposed HHV-8 protein fragments of ORF26 and ORF75 display 60% and 30% amino acid identity with their HVS (2, 12) and EHV-2 counterparts (29) and show a slightly more distant relationship to EBV. The known gamma-1 herpesviruses include human EBV and its close relatives in great apes and old world primates (35). The gamma-2 viruses originally included the rhadinoviruses, exemplified by HVS and its close relatives in new world primates, and the cottontail rabbit virus H.sylvilagis. The biological feature of lymphotrophism, including the ability to immortalize and establish a circular plasmid or episomal latent state, was the major common feature that placed them all into the gamma herpesvirus group, and their preferences for B-cells (EBV) or T-cells (HVS) was used as a criterion to discriminate between the gamma-1 and gamma-2 class subgroupings (11, 43, 56). Subsequently, DNA sequence analyses of small segments of EHV-2 and EHV-5 (14, 67), bovine herpesvirus type 4 (BHV-4) and the mouse herpesvirus MHV68, have also revealed closer protein sequence relationships and gene order to HVS than to any other known herpesviruses, despite exhibiting a much broader permissive host cell range including cultured fibroblasts, and a latency trophism that may include T-cells, B-cells or macrophages (15, 25, 39, 60, 67).

Complete genomic DNA sequence data is now available for three prototype gamma herpesviruses including EBV (7), HVS (3, 4, 48) and EHV-2 (61). EHV-2 appears to represent a distinct subgroup of the gamma-2 herpesviruses based on its overall (G+C)-content of 58%, compared to the much lower 35% and 43% for the unique regions of HVS and BHV4 (14, 22), together with the presence of large 18-kb terminal direct-repeat structures, rather than the short multicopy tandem-repeat patterns found at the termini of HVS and BHV-4 (9, 15, 58). Apart from the essentially co-linear organization of major gene blocks (31), each of these gamma herpesviruses contain several clusters of additional genes that are unique to each species and are often not found in any other herpesvirus (32). In EBV, these species-specific or subtype-specific genes include the EBNAs and all other latency-associated genes, the lytic cycle transcriptional and replication control protein ZTA, virus cell-type-specific receptors, and gene products that interfere with or protect against immune surveillance mechanisms (23, 32, 34, 41, 42). All of these optional genes, plus others with as yet unidentified functions, map to within one of six divergent loci in gamma herpesvirus genomes that we refer to from left to right as DL-A to DL-F (39). Amongst the relevant virus-specific and subtype-specific genes that are unique to gamma herpesviruses there is a thymidylate synthase (TS) gene in HVS and EHV-2, but not in EBV or BHV-4 (12, 36, 61). Both EBV and EHV-2, but not HVS or EHV-4, also encode vIL10 genes (54, 61, 65), and amongst the four only HVS encodes a DHFR gene (62). EBV and HVS, but not EHV-2 encode a Bcl-2 homologue and only HVS encodes a vIL17 gene (68). The TS, DHRF, vIL10 and vIL17 genes are highly conserved with the corresponding cellular versions (70 to 85% amino acid identity) and have been suggested to be relatively recent acquisitions as unspliced cDNA versions from the host mammalian genome.

Many intriguing questions arise as to how HHV-8 fits into this classification scheme and what is its evolutionary relationship to the other gamma herpesviruses, as well as whether HHV-8 is indeed an authentic infectious and ubiquitous human virus, rather than a relatively rare pathogen or recent acquisition from some exogenous primate source that has been spread more rapidly within the AIDS epidemic.

Thus there is a need in the art for additional tools for characterizing, diagnosing, and treating HHV-8 which has been found to be associated with a number of human diseases.

SUMMARY OF THE INVENTION

It is an object of the present invention to provide an isolated and purified HHV-8 virally encoded protein.

It is another object of the present invention to provide an antibody preparation which is specifically immunoreactive with an HHV-8 virally encoded protein, but is not immunoreactive with a cellular homologue of the protein.

It is an object of the present invention to provide a polynucleotide which encodes one or more of HHV-8 virally encoded proteins.

Another object of the invention is to provide a polynucleotide probe or primer for detecting HHV-8 virus divergent locus DL-B.

Another object of the invention is to provide a polypeptide which comprises at least 13 contiguous amino acids selected from a HHV-8 virally encoded protein.

Another object of the invention is to provide a method for diagnosing an HHV-8 associated disease, such as Kaposi's sarcoma, Castleman's disease, Multiple myeloma, and Body cavity based large cell lymphoma (BCBL).

Another object of the invention is to provide another method for diagnosing an HHV-8 associated disease.

Still another object of the invention is to provide a method of screening test compounds for candidate drugs for treating HHV-8 infections.

These and other objects of the invention are achieved by providing one or more of the embodiments described below. According to one embodiment of the invention an isolated and purified HHV-8 virally encoded protein is provided. The protein is selected from the group consisting of: TS, DHFR, Bcl-2, IL-6, MIP-1A, MIP-1B, BCK, IE-1A, and IE-1B, as shown in SEQ ID NO: 22, 23, 24, 25, 26, 27, 28, 29, and 30, respectively.

According to yet another embodiment of the invention an antibody preparation is provided which is specifically immunoreactive with an HHV-8 virally encoded protein, but is not immunoreactive with a cellular homologue of the protein. The virally encoded protein is selected from the group consisting of: TS, DHFR, Bcl-2, IL-6, MIP-1A, MIP-1B, BCK, IE-1A, and IE-1B, as shown in SEQ ID NO: 22, 23, 24, 25, 26, 27, 28, 29, and 30, respectively.

According to still another embodiment of the invention a polynucleotide is provided which encodes one or more of HHV-8 virally encoded proteins. The one or more virally encoded proteins are selected from the group consisting of: TS, DHFR, Bcl-2, IL-6, MIP-1A, MIP-1B, BCK, IE-1A and IE-1B, as shown in SEQ ID NO: 22, 23, 24, 25, 26, 27, 28, 29, and 30, respectively. The polynucleotide does not contain HHV-8 genes which are not in the divergent locus DL-B.

In still another embodiment of the invention a polynucleotide probe or primer is provided for detecting HHV-8 virus divergent locus DL-B. The probe or primer comprises at least 12 contiguous nucleotides selected from the group consisting of: SEQ ID NO: 1, 2, 3, 4, 5, 6, 7, 8, and 9.

In yet another embodiment of the invention a polypeptide is provided which comprises at least 13 contiguous amino acids selected from a HHV-8 virally encoded protein. The virally encoded protein is selected from the group consisting of: TS, DHFR, Bcl-2, IL-6, MIP-1A, MIP-1B, BCK, IE-1A, and IE-1B, as shown in SEQ ID NO: 22, 23, 24, 25, 26, 27, 28, 29, and 30, respectively.

Also provided by the present invention is a method for diagnosing a HHV-8 associated disease, such as Kaposi's sarcoma, Castleman's disease, Multiple myeloma, and Body cavity based large cell lymphoma (BCBL). The method comprises the steps of:

detecting an HHV-8 viral polynucleotide or protein in a body sample of a patient, wherein presence of an HHV-8 polynucleotide or protein indicates an HHV-8 associated disease, wherein the HHV-8 virally encoded protein is selected from the group consisting of: TS, DHFR, Bcl-2, IL-6, MIP-1A, MIP-1B, BCK, IE-1A, and IE-1B, as shown in SEQ ID NO: 22, 23, 24, 25, 26, 27, 28, 29, and 30, respectively, and the HHV-8 polynucleotide is selected from the group consisting of SEQ ID NO: 1, 2, 3, 4, 5, 6, 7, 8, and 9.

According to another embodiment of the invention another method is provided for diagnosing an HHV-8 associated disease. The method comprises:

detecting antibodies in the serum of a patient. The antibodies specifically bind to an HHV-8 protein selected from the group consisting of: TS, DHFR, Bcl-2, IL6, MIP-1A, MIP-1B, BCK, IE-1A, and IE-1B, as shown in SEQ ID NO: 22, 23, 24, 25, 26, 27, 28, 29, and 30, respectively.

Another embodiment of the invention is a method of screening test compounds for candidate drugs for treating HHV-8 infections. The method comprises:

contacting a test compound with an HHV-8 virally encoded protein selected from the group consisting of: TS, DHFR, Bcl-2, IL-6, MIP-1A, MIP-1B, and BCK, as shown in SEQ ID NO: 22, 23, 24, 25, 26, 27, 28, 29, and 30, respectively; and testing the protein for activity, wherein a test compound which inhibits activity of the protein is a candidate drug for treating HHV-8.

The present invention thus provides the art with a large number of new diagnostic and therapeutic agents for dealing with HHV-8. In addition, it provides the art with targets for development of drugs for treating HHV-8 infections.

BRIEF DESCRIPTION OF THE DRAWINGS

FIG. 5: Amino Acid Sequence of the Predicted HHV-8 Thymidylate Synthetase (TS) and Dihydrofolate Reductase (DHFR) Enzymes. (A) Alignment of the TS proteins of HHV-8 (SEQ ID NO:22), *H.saimiri* (HVS, SEQ ID NO:31), *H.ateles* (HVA, SEQ ID NO:32), varicella-zoster virus (VZV, SEQ ID NO:33) and human DNA (SEQ ID NO:34). Identical regions are boxed. Homology values are listed in Table 1. (B) Alignment of the DHFR proteins of HHV-8 (SEQ ID NO:23), *H.saimiri* (HVS, SEQ ID NO:35), human (SEQ ID NO:36), pig (SEQ ID NO:37), and Drosophila (SEQ ID NO:38). Identical regions are boxed. Homology values are listed in Table 1.

FIG. 6: Predicted Amino Acid Sequences of Zinc Finger and Cys-Bridge Proteins Encoded by HHV-8 DL-B ORFs. Identical regions are boxed. Conserved Cys and His residues characteristic of PHD/LAP zinc fingers and of IL-6 and β-chemokine Cys bridges are indicated by asterisks. (A) Comparative alignment of the IE-1A ORF encoding the 256 amino acid PHD/LAP zinc finger protein (SEQ ID NO:29) and the IE-1B ORF encoding the 333 amino acid PHD/LAP zinc finger protein (SEQ ID NO:30). Dotted lines denote similarities. (B) Comparative alignments of the HHV-8 ORF-encoding the 114 amino acid β-chemokine-like (BCK) protein (SEQ ID NO:28) with HHV-8 vMIP-1A (SEQ ID NO:26) and vMIP-1B (SEQ ID NO:27) and other β chemokines. The most closely related known proteins to HHV-8 BCK in BLAST and FASTA searches are rat and mouse MCP-1 [S07723, A30209], human T-cell activation protein-2 [A31767] and the human CC-chemokine [Z75668]. Human MIP1-α (SEQ ID NO:39) and RANTES (SEQ ID NO:40) as well as HHV8, vMIP1A and vMIP1B are also shown for comparison. (C) Comparative alignment of HHV-8 vIL-6 (SEQ ID NO:25) and human IL-6 (SEQ ID NO:45).

FIG. 7: Comparison of the Zinc Finger Motifs in HHV-8 IE-1A and IE-1B, BHV-4 IE1 Exons A and B and HVS ORF12 with Other PHD/LAP and RING Finger Subtypes. (A) Alignment of appropriate N-terminal sections of the two putative HHV-8 IE1 ORFs that contain C4HC3 motifs (SEQ ID NOS:52 and 53) with those of both exons of BHV-4 IE1 (64) (SEQ ID NOS:54 and 55) and ORF12 of HVS (SEQ ID NO:56), as well as Chlamydomonas ZYS-1A (SEQ ID NO:46), the swine pox virus C7 gene (40) (SEQ ID NO:51), *S.cerevisiae* SSM4 [P40318] (SEQ ID NO:48) and *C.elegans* D2089.2, F58E6.1 and M110.2 [Z36948 (SEQ ID NO:49), Z70754 (SEQ ID NO:50) and Z49968 (SEQ ID NO:47)]. These eleven motifs represent a distinct subset that we refer to as the BKS versions (BHV4, KSHV & Swinepox) of the C4HC3 PHD/LAP finger motif. The motif designated BHV-4 IE-1B represents nucleotide positions 715 to 873 in Genbank file Accession No. M60043. (B) Examples of two typical standard versions of cellular C4HC3 PHD/LAP zinc finger motifs from the human AF10 and MLLa proteins that are disrupted by translocations in acute myoblastic leukemia (55) (SEQ ID NOS: 57 and 58). (C) Comparative alignment of four prototype C3HC4 pattern RING finger motifs from RAG-1 (SEQ ID NO:59), HSV ICP0 (SEQ ID NO:60), PML (SEQ ID NO:61) and BRCA-1 (SEQ ID NO:62) and a depiction of their predicted cross-braced zinc coordinated structure (28).

FIG. 9: Time Course of Induction of IE-1A and DHFR mRNA in Butyrate Treated BCBL Cell Lines. (A) DHFR riboprobe, HBL6 cells. Lanes 1 to 6 RNA samples prepared at 0, 5, 8, 12, 24 and 48 h after addition of NBA; 7, 12 h after addition of NBA in the presence of CHX. (B) IE-1A riboprobe, HBL6 cells. Lanes 8 to 13, RNA samples prepared at 0, 5, 8, 12, 24 and 48 h after NBA addition. (C) IE-1A riboprobe, EBV negative BCBL-1 cells. Lanes 14 to 17. RNA samples prepared at 0, 5, 12 and 24 h after NBA addition.

DETAILED DESCRIPTION

Figure 1A:
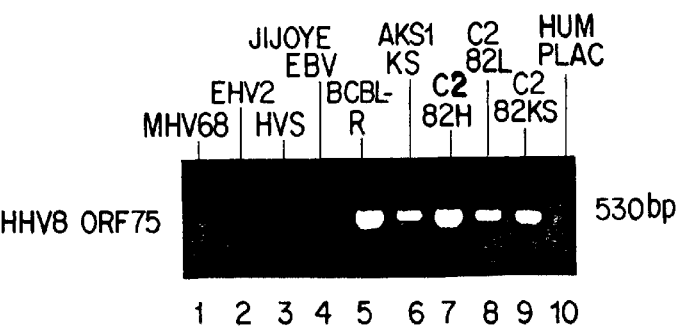
FIG. 1: Evidence for a Viral Thymidylate Synthetase Gene in Human BCBL DNA as Detected by the Redundant PCR Probe Approach. The diagram shows direct ethidium bromide stained PCR product DNA bands in the appropriate selected size range after fractionation of each set of products by electrophoresis on parallel agarose gels (panels A to E). Size marker lanes containing a multimerized 123-bp ladder series were included in the outside lanes in all gels (not shown). The template samples used in lanes 1 to 10 include control gamma herpesvirus DNA (lanes 1 to 4), BCBL and KS samples (lanes 5, 6 & 9) heavy and light CsCl fractionated C282 DNA samples (lanes 7 and 8), and negative control human placental DNA (lane 10). Each PCR reaction mixture contained 100 ng of template cellular DNA or 3 ng each of the EHV-2 virion DNA, the sucrose gradient fractioned BCBL-R sample and the CsCl fractionated C282H and L samples.

It is a discovery of the inventors that the DL-B locus of HHV-8 DNA from both KS and BCBL samples encodes as many as nine ORFs that are related to known cellular proteins, including TS and DHFR enzymes and two LAP zinc-finger motif proteins that are characteristic of several other gamma-2 class herpesviruses. These HHV-8 encoded cytokine genes, (Il-6, MIP-1A, and MIP-1B) and a Bcl2 homologue also mapped to this locus. In addition, a fourth HHV-8 cytokine gene related to β chemokines and referred to as BCK has been found.

Isolated and purified proteins from the DlB locus are provided. These proteins can be made using the nucleotide sequences which encode them naturally in the virus. They can also be made using other variant coding sequences, or they can be made synthetically. Isolated and purified proteins have been removed from the cellular millieu, and have been purified to at least form 10% of the proteins (by weight) in the preparation. Preferably the preparation will be more pure, so that the HHV-8 protein forms at least 25, 40, 50 60, 75, 85, 90, or 95% of the protein in the preparation. Any means known in the art can be used to purify and isolate the protein from cells. Particularly useful methods are based on the sequence information dislcosed here, such as immunological methods. Such methods rely on the use of antibodies which bind to the protein with specificity.

Polypeptide portions of the proteins can also be useful, both as immunogens and as antigens or reagents. These can be preferably at least 13, 15, 17, 19, 21, 23, 25, 30, 35, or 50 contiguous amino acids of the respective proteins. The polypeptides can also be covalently linked to other amino acids, as in fusion proteins which link the viral sequences to other useful sequences, such as enzymes, secretion leader sequences, and immunological tags.

Antibodies can be made according to any method known in the art. Whole proteins, polypeptide portions of proteins, fusion proteins, can all be used to immunize animals to raise an humoral immune response. The antibodies can be purified, for example, using affinity chromatography. The antibodies can be monoclonal, if the spleen of the immunized animal is used to make hybridomas or otherwise immortalized cells. Specifically binding antibodies are those which bind with a greater binding affinity to the particular HHV-8 protein than to other proteins. Preferably the greater binding affinity is at least two-fold and preferably at least ten-fold greater than to other proteins.

Polynucleotides according to the invention are all or portions of genes which have been purified away from other non-DL-B HHV-8 sequences. Preferably other cellular polynucleotides have also been removed. The polynucleotides can be in expression constructions, labeled to form a probe, appended with a restriction enzyme site, or in any other form which may be useful for a particular purpose. They may also be used as primers for synthesis and amplification. In addition, they can be joined to sequences to form ribozymes, as is well known in the art. Preferably at least 12, 20, 30, 40, 50, 100, or 200 contiguous nucleotides of the natural HHV-8 sequence are used. Means for synthesizing, isolating, labeling, and cloning polynucleotide sequences are well known in the art. The polynucleotides can be cDNA or viral genomic DNA; they may also be put in constructs in inverse orientation to form anti-sense constructs which express RNA complementary to the native mRNA. They may also be part of ribozymes.

The viral promoters and regulatory elements may be used to control other (non-viral) sequences in chimeric constructs. Conversely, non-viral promoters and regulatory elements can be used to control the viral sequences disclosed herein.

Methods for diagnosing a disease associated with HHV-8 include any by which HHV-8 viral polynucleotides or proteins are detected in a body sample of a patient. The body sample may be a tissue sample, blood, serum, sputum, saliva, etc. Any source of viral proteins or nucleic acids will provide a suitable sample. It may be desirable to treat the patient or the sample prior to the step of testing with a drug or agent which induces viral expression. Such drugs or agents include butyrate, phenylbutyrate, and azacytidine, and derivatives thereof. Detection methods include any that are known in the art. Protein and antibody detection methods include without limitation: ELISAs, immunoblots, immunoprecipitation. Autoantibodies can be detected using the same techniques. Nucleic acid detection methods include PCR, Northern blots, Southern blots, in situ hybridizations, etc. Any convenient technique or format can be employed to test for the disclosed HHV-8 proteins and gene sequences. The presence of HHV-8 DL-B proteins or nucleic acid sequences in the sample indicates an HHV-8 infection which may develop into one of the diseases which HHV-8 plays an etiological role. Antiviral treatments may ameliorate or alleviate the development of the full disease symptoms.

The HHV-8 proteins of the present invention can be used to screen for test compounds which are useful for treating HHV-8 infections. Such screening methods typically employ the contacting of a test compound with one of the virally encoded proteins and determining whether the activity of the protein is inhibited by the test compound. A test compound which inhibits function of one or more of the viral proteins is a candidate drug for treating HHV-8. Further testing to determine that the test compound does not inhibit the cellular homolog of the HIV-8 protein will establish specificity for the virus. These screening assays can be performed using in vitro or in vivo formats. In the former, isolated proteins are contacted in a cell-free system with the test compounds. In the latter cells which express the viral proteins are contacted with the test compounds. The functional assays for the protein can be performed thereafter, either in vitro or in vivo. As described herein, the viral proteins of DL-B share activities with their cellular homologues, therefore similar assays can be used for the viral proteins as for the cellular homologues.

The proteins and polypeptides of HHV-8 DL-B can be expressed according to any method known in the art. They can be expressed in bacteria, using bacterial expression cloning systems. They can be expressed in in vitro translation systems using HHV-8 mRNA as a template, or in coupled transcription/translation systems, using HHV-8 DNA as a template. The DL-B genes can also be expressed in mammalian cells, either in transiently transfected cells or in stable transfectants, such as in CHO cells. Methods for such expression are known in the art. Using such expression systems it has been found that the viral DHFR confers methotrexate sensitivity on mammalian cells, and the thymidylate synthase confers 5-fluorouracil senstivity on *E. coli* cells. Moreover, using such expression systems it has been demonstrated that the viral homologues of cellular cytokine proteins have similar or overlapping biological function as the cellular proteins.

The thymidylate synthetase (TS)-like gene fragment amplified from the BCBL DNA sample was found to encode part of a protein that had 70% amino acid identity to both human TS and to the ORF70 proteins of HVS and EHV-2 and was slightly further diverged from the varicella zoster virus (VZV) version. Since EBV does not possess a TS gene and the mammalian versions are spliced, we interpreted that this probably represented an HHV-8 gene. This conclusion was confirmed by the isolation of a phage lambda clone from a BCBL genomic DNA library that also contained diverged homologues of other gamma herpesvirus genes such as ORF6 and ORF10. The HHV-8 TS fragment was found to be present consistently in all samples of KS or BCBL DNA tested from twelve different patients, but was not found in any non-KS or BCBL control samples. Based on this locus as a probe, a set of overlapping phage lambda clones were identified from the BCBL-R library that linked up into a contiguous 48-kb segment, encompassing the equivalent of HVS ORF6 to 31 and overlapped with the left-hand end of the previously described 20-kb ORF20 to ORF35 segment of KS HHV-8 (46). We focused our attention only on a region surrounding the TS gene of HHV-8 with the anticipation that it would represent the equivalent of the gamma herpesvirus divergent locus DL-B, which we hoped would reveal additional clues about the evolutionary relationship of HHV-8 to other gamma herpesviruses.

Combined physical mapping and DNA sequence analysis has revealed that HHV-8 contains an expanded region of nearly 18-kb of DNA within the DL-B region between homologues of HVS ORF9 and ORF17, compared to only 7-kb in this region in HVS (FIG. 4). Furthermore, HHV-8 encodes at least nine genes whose products have homology to cellular proteins or motifs within this region, including ORFs representing the TS, DHFR, BCK-like, and two PHD/LAP zinc-finger class proteins described here, as well as vIL6 and two vMIP-1 homologues (50) and a highly diverged but positionally conserved version of HVS Bcl-2 (21). At least five of these genes produced distinct lytic cycle transcripts at 12 h after butyrate induction in both EBV positive and EBV negative BCBL cell lines that carry apparently latent HHV-8 plasmid genomes. Note that only Bcl-2 and one PHD/LAP zinc finger protein are also found at this equivalent location in the prototype gamma-2 herpesvirus genome of HVS, together with vIL17 (ORF13), the IE-G (ORF14) protein and a CD59 homologue (ORF15); (4). However, HVS and EHV-2 both contain homologues of the TS gene (referred to as ORF70) near the right-hand-end of the unique segments of their genomes. Furthermore, only HVS also contains a DHFR gene, although this is designated ORF2 and lies near the extreme left-hand end of the genome. None of the other eight genes are present in the EHV-2 genome.

Based on their very different genomic locations, and the fact that the HHV-8 version of the DHFR protein is much farther diverged from the HVS version than the HVS version is from human DHFR (48% identity compared to 84% identity), we conclude that the two gamma herpesvirus DHFR genes were probably acquired from their hosts as separate events at different time periods in gamma herpesvirus evolution. Assuming that the two DHFR genes did not evolve at different rates, capture by the HHV-8 progenitor must have occurred long before that in a common progenitor of HVS and EHV-2. The TS genes may also have had different evolutionary origins, although based on their equivalent degrees of homology and divergence from the human version (66% for HHV-8 and 69% for HVS) we cannot exclude the possibility of a secondary translocation in this case. Varicella-zoster virus (VZV) is unique amongst alpha herpesviruses in also containing a TS gene (63% identity), which again is positioned at a different genomic location than are either of the two gamma virus TS loci. Furthermore, there is also the precedent from the Bcl-2 homologues in EBV and HVS, and the vIL10 homologues in EBV and EHV-2, which also both represent acquired cellular cDNA genes that occupy different positions in their respective genomes. The apparent duplication of vMIP-1and IE1 genes and the acquisition of three distinct types of cytokines within the same divergent locus by HHV-8, but the presence of vIL17 instead at this locus in HVS, also attests to the relative frequency of these recombinational events and the high genomic fluidity at this site.

Finally another gamma herpesvirus, BHV-4, possesses apparent evolutionary homologues of the two HHV-8 zinc-finger proteins described here, but neither EBV or EHV-2 do so. In this case, the BHV-4 IE1 gene maps at the equivalent location and in the same orientation as the HHV-8 genes (i.e. leftwards within DL-B). We have also identified HVS ORF12 as another positionally equivalent member of this family. The two HHV-8 versions are much more closely related to each other than to those in the other two viruses (FIG. 6A) and, although direct homology between the HHV-8, BHV-4 and HVS versions of these proteins does not extend beyond the N-terminal zinc-binding motifs, they all resemble each other to the extent of having several internal hydrophobic domains. Only one of the BHV-4 motifs was recognized originally (64) and it was suggested then to be closely related to the zinc finger motif in the HSV ICP0 (or IE110) transactivator protein. However, our analysis has revealed that within the single IE1 transcription unit of BHV-4 both exons 4 and 5 contain a $C_4HC_3$ type of zinc-finger motif which is distinct from the $C_3HC_4$ motif in ICP0. In fact, the gamma-2 herpesvirus motifs all closely resemble a subset of $C_4HC_3$ zinc finger motifs within the PHD/LAP class found only in the C7 protein encoded by swine pox virus (40) or in the ZYS1A/B proteins of Chlamydomonas and in several *S. cerevisiae* and *C. elegans* proteins, but otherwise they differ significantly from most other $C_4HC_3$ PHD/LAP class motifs, and from the better known $C_3HC_4$ and $C_2HC_5$ classes of RING and LIM zinc-finger motifs (FIG. 7). The zinc-binding motif in the HSV ICP0 nuclear regulatory protein and its alpha herpesvirus relatives is of the RING-finger class, and there is no obvious resemblance otherwise to the gamma-2 herpesvirus IE1 zinc finger proteins, which appear likely to be membrane proteins.

The overall similarity amongst the two PHD/LAP zinc-finger containing proteins in HHV-8, the two IE1 exons in BHV-4 and ORF12 in HVS, is sufficient to conclude that these proteins in the three viruses have a common evolutionary origin and presumably are likely to have related functions. Therefore, we have provisionally designated the HHV-8 versions as IE-1A and IE-1B based on previous evidence that at least one of the BHV-4 versions (exon-4) is expressed as a classical lytic cycle IE class mRNA after infection of permissive cells with BHV-4 virions (64). The ability of CHX to block HHV-8 IE-1A and IE-1B transcription after butyrate induction in BCBL cell lines is not necessarily relevant to the question of IE characteristics after primary infection. The RING class zinc finger domains in HSV ICP0 are known to have an unusual cross-braced zinc coordination pattern creating distinctive alpha helical and β sheet structures that are believed to be protein:protein interaction domains (27, 28); however, the PHD/LAP motif is structurally sufficiently different that no predictions about function can yet be made. Interestingly, at least three human members (AF10, MLLT6 and MLLa) of the leukemia associated protein domain (LAP) family with similar $C_4HC_3$ zinc finger motifs are disrupted in acute myeloid leukemias (55).

We conclude that gamma herpesviruses are likely to have both captured and lost cellular cDNA genes such as Bcl-2, IL10, TS and DHFR on multiple occasions during their evolution, and that in similarly acquiring both multiple cytokine and cytokine receptor genes etc, they have undergone rather dynamic additions and subtractions to their genome content, especially within the divergent loci. Presumably, separate independent acquisitions of the same gene may reflect some selective advantage to encoding these proteins. The whole process of gaining, losing or rearranging genes at divergent region recombination "hot spots" may be a relatively modern reflection of the ongoing long-term evolutionary events that also generated the more stable subclass-specific segments of alpha, beta and gamma herpesvirus genomes seen now, and perhaps even those events that originally incorporated the common replication enzyme genes of all of these viruses.

With regard to the overall relationship of HHV-8 to other gamma herpesviruses, the amino acid comparisons of the stable conserved MCP proteins presented by Moore et al (46) clearly support a slightly closer evolutionary history to HVS than to EHV-2 and much further divergence from EBV. The patterns of gene conservation within DL-B and DL-E also reveal more similarity between HHV-8 and HVS than to EHV-2 with regard to the presence of the conserved ORF10, ORF11, ORF12 (IE1), ORF16 (Bcl-2), and ORF72 (cyclin-D) (20) genes. However, HVS and EHV-2 are more similar to each other than to HHV-8 in possessing a common ORF70 TS gene locus, whereas all three of them possess an ORF74 (GCR) gene (33). Furthermore, HHV-8 appears more similar to BHV-4 than to either of the others with regard to the conservation of two IE1 zinc finger motif proteins or exons, but BHV-4 apparently lacks any DHFR, TS, cyclin-D, GCR, IL10, Bcl-2 or cytokine genes (39). Obviously, the potential of the HHV-8 encoded TS and DHFR proteins as novel targets for antiviral therapy, the expectation that at least one of the IE1-like zinc-finger protein(s) may serve as an IE class lytic cycle regulator for this virus, and the likely biologically intriguing consequences of expressing viral encoded inflammatory cytokines will lead to further more extensive studies of the function and expression of these genes.

The above disclosure generally describes the present invention. A more complete understanding can be obtained by reference to the following specific examples which are provided herein for purposes of illustration only, and are not intended to limit the scope of the invention.

EXAMPLE 1
Use of Redundant PCR Primers to Detect Gamma Herpesvirus Genes

Figure 1B:
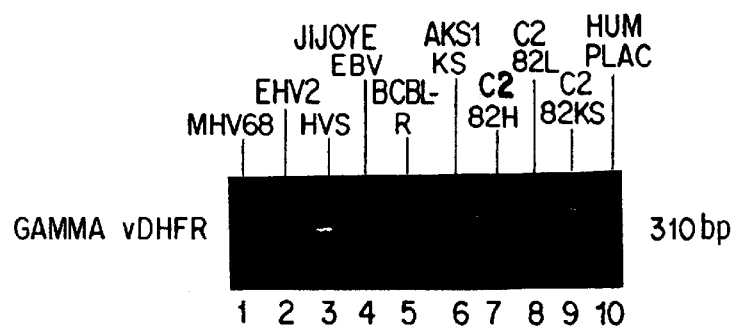
Figure 1C:
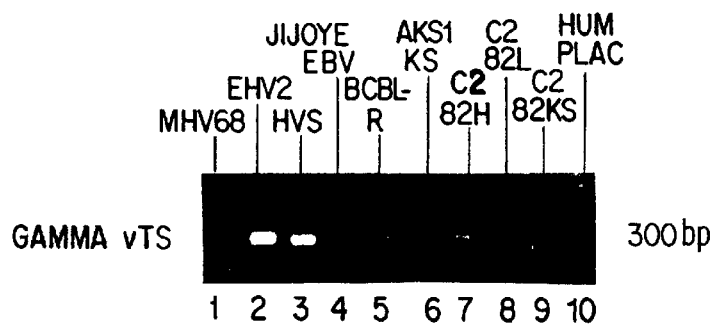

Pairs of redundant PCR primers encoding short well-conserved amino acid blocks common to known gamma herpesvirus versions of the uracil DNA glycosylase (UDG), thymidylate synthase (TS), interleukin-ten (IL10) and dihydrofolate reductase (DHFR) genes were synthesized and tested for amplification of DNA products at low stringency on six different species of gamma herpesvirus DNA preparations. These samples included human EBV (present in the Jijoye or Raji B-lymphoblast cell lines), baboon and orangutang gamma-1 herpesviruses (*H.papio* and *H.pongo*) in B-lymphoblast cell lines, squirrel monkey gamma-2 (HVS) DNA from infected Vero cells, purified equine gamma-2 (EHV-2) virion DNA and mouse gamma-2-like (MHV68) virion DNA. Note that the spliced cellular versions of these genes are not expected to be detected because of their larger size, whereas the introns are missing in the viral versions. The IL10 PCR primers proved to detect a vIL10 gene in EBV, *H.pongo*, *H.papio* and EHV-2, but not in any of other samples (not shown), whereas the UDG probes detected viral UDG genes in all six gamma herpesvirus DNA samples tested (not shown). The DHFR primers, which were designed based on blocks of homology between the HVS version and human and mouse DHFR, failed to detect a DHFR gene in any sample other than the HVS DNA (FIG. 1B, lane 3). As expected, the TS primers detected TS genes in both EHV-2 and HVS (FIG. 1C, lanes 2 & 3), but not in EBV, MHV68 or the two non-human primate gamma-1 DNAs (FIG. 1B, lanes 1 & 4).

Detection of a Viral TS Gene in BCBL and KS DNA by the Redundant PCR Approach

Figure 1D:
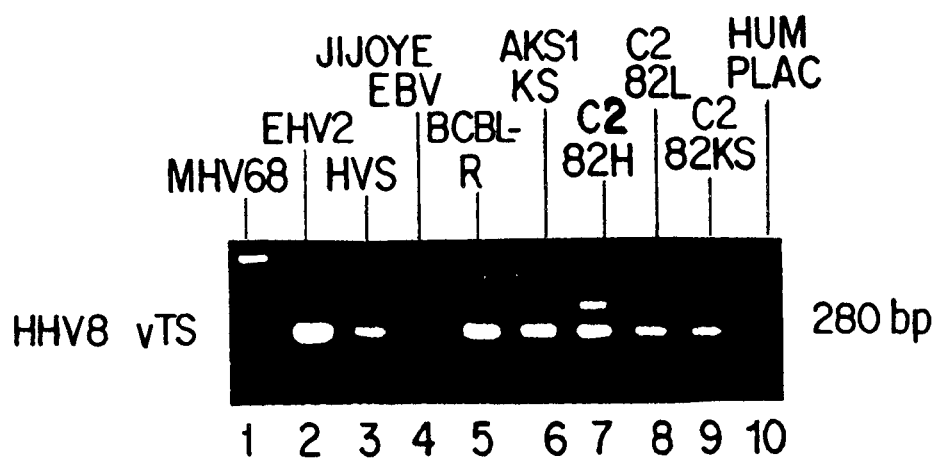
Figure 1E:
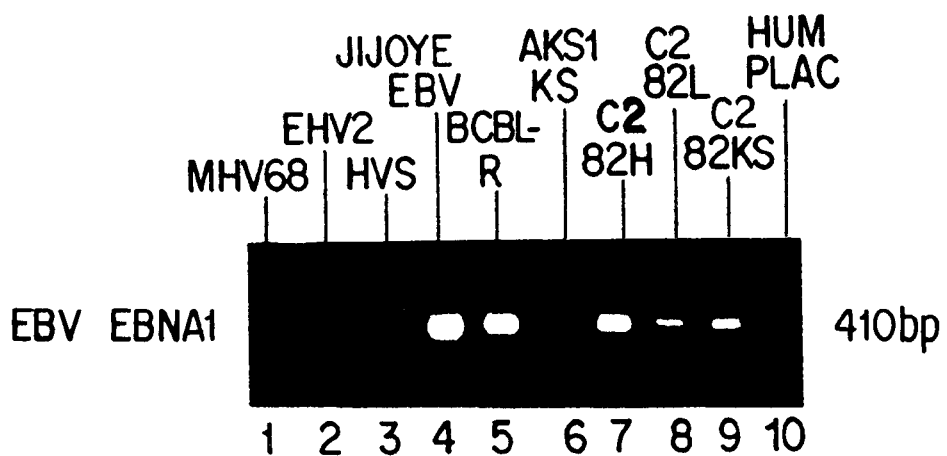

Amongst the four redundant gamma class PCR primers described above only one, the TS pair, proved to detect an apparent HHV-8 homologue. In the initial studies, three potential HHV-8 positive DNA samples were tested for direct ethidium bromide stained PCR products, including an AIDS-associated body cavity based lymphoma tumor (BCBL-R), a biopsied KS lesion (AKS1) and KS autopsy sample (C282). Analysis of these DNA samples for direct ethidium bromide stained PCR products with a sensitive HHV-8 ORF75 primer pair revealed considerably more HHV-8 DNA in the BCBL-R sample (FIG. 1A, lane 5) than in either of the two KS lesions (FIG. 1A, lanes 6 & 9). This primer pair proved to be highly specific for HHV-8 and failed to detect homologous sequences in MHV68, EHV-2, HVS, Jijoye (EBV) or human placental DNA samples (FIG. 1A, lanes 1 to 4 & 10). However, the BCBL-R and C282 samples were also strongly positive for EBV and the AKS1 sample was weakly positive for EBV as detected with an EBNA-1 specific PCR primer pair (FIG. 1E, lanes 5, 6 & 9). As expected, both EBV and HHV-8 DNAs were enriched in the C282 KS sample by banding in a CsCl density gradient to partially separate (G+C) rich viral DNA (FIG. 1A and E, lane 7; C282H) from the cellular DNA fraction of lower G+C content (lane 8, C282L).

The vIL10, UDG and TS primers were also all positive with the BCBL-R and C282 KS samples, but not surprisingly, sequencing of the products revealed that the vIL10 and UDG products obtained were derived from a subtype A EBV genome. However, EBV lacks a TS gene and the sequence of the TS PCR product obtained from the BCBL-R sample (FIG. 1C, lane 5) revealed the presence of a novel fragment of a TS gene closely related to that in HVS. The 300-bp PCR product contained a partial ORF with 67% identity to HVS and *H.ateles* TS and 63% to the human version. This TS fragment was not detectable directly with the redundant primer in either the AKS1 or C282 KS DNA samples (FIG. 1C, lanes 6 & 9), but it was detected within the high (G+C) content fraction in the viral DNA enriched sample after banding in CsCl (C282H; lane 7). Furthermore, the DNA sequence of the C282 KS TS fragment proved to be identical to that from the BCBL-R fragment. Based on these sequences, a new HHV-8 vTS specific primer pair was designed, which now detected a 280-bp TS gene fragment directly in all three of the HHV-8 positive samples (FIG. 1D, lanes 5, 6 & 9) as well as in EHV-2 and HVS (at low stringency, 48°), but not in MHV68 or Jijoye EBV, nor in the human placental DNA control (FIG. 1D, lanes 1, 4 & 10).

Sources of KS and BCBL DNA and Gammaherpesvirus DNA Samples

A variety of discarded KS-related autopsy and biopsy samples were accumulated from both AIDS and non-AIDS patients at Memorial Hospital Sloan-Kettering Institute (New York) and from Zaire in 1983 and 1984 (5), as well as a variety of additional specimens from Johns Hopkins Hospital and the National Institutes of Health in 1995. These included AIDS KS autopsy samples labelled C282 and ASM70 to 80 (New York, 1984), endemic African KS DNA samples 431KAP and 431NSC (from Zaire, 1984), AIDS-associated female KS DNA samples ST1, ST2 and ST3 (from Uganda, 1995), fresh frozen AIDS associated AKS1 and non-AIDS associated EKS1 lesion samples (from Baltimore, 1995), an AIDS KS lesion DNA sample referred to as AKS2 (from NIH, 1995) and a paraffin-embedded AIDS-associated KS lesion AKS4 (from Baltimore, 1995). Other HHV-8 positive samples included the original BCBL tumor DNA (BCBL-R) used to prepare the phage lambda library (from NIH, 1995) and DNA from the HHV-8 plus EBV positive HBL6 cell line derived from the BC1 cell line (16). DNA samples from all tumor, biopsy and tissue or cell culture sources were extracted with pronase and phenol followed by ethanol precipitation and dialysis against Chelex. DNA concentrations were measured by UV absorption.

Total cell DNA from cultured human Raji and Jijoye B-lymphoblasts carrying latent state EBV genomes was prepared by pronase and phenol extraction followed by ethanol precipitation. Similar procedures were used to extract DNA from HVS lytically-infected Vero cells, MHV68 infected MEF cells and both the H. papio infected baboon B-lymphoblast cell line (BA34) and a newly isolated H.pongo infected orangutang B-lymphoblast cell line. Purified EHV-2 virion DNA was obtained from Dennis J. O'Callaghan (Univ. of Louisiana, Shreveport).

Redundant Primers and PCR Analysis

The redundant PCR primers originally used to detect a 300-bp gamma 2 TS band were 5'-GGRCCYGTSTAYGGRTTYCAGTGG-3' (LGH1967) (SEQ ID NO:10) and 5'-CTGGC(Y/G)ATGTTGAARGGRAC(Y/G)CC-3' (LGH1968) (SEQ ID NO:11). The second generation HHV-8 specific TS PCR primers used to detect a 280-bp band were 5'-GGGTTCCAGTGGAGGCAC-3' (LGH2018) (SEQ ID NO:12) and 5'-ACGTGGATCCCTCTGACAACC-3' (LGH2019) (SEQ ID NO:13). The HHV-8 ORF26 PCR primers used to obtain 330-bp bands, namely 5'-GGAT GGATCCCTCTGACAACC-3' (LGH1701) (SEQ ID NO:14) and 5'-ACGTGGATCCGTGTTGTCTACG-3' (LGH1702) (SEQ ID NO: 15), were based on the sequence of the KS330Bam fragment of Chang et al (19). The ORF75 PCR primers used to obtain 530 bp amplified bands, namely 5'-CTAGAGATCTGTTTAGTCCGGAG-3' (LGH1984) (SEQ ID NO:16) and 5'-GTAC GGATCCACGGAGCATAC-3' (LGH1704) (SEQ ID NO:17), were derived from the KS631Bam DNA sequence of Chang et al (19). The UPS75 PCR primers used were 5'-CAGTTACATGTAGCCATG-3'(LGH2024) (SEQ ID NO:18) and 5'-CTGCATCAGTACACTATTC-3' (LGH2025) (SEQ ID NO:19), which were derived from DNA sequence analysis at the left-hand end of a BCBL-R phage lambda DNA clone (λB5-1) identified by hybridization with the KS631Bam ORF75 probe. The EBNA-1 primer pair used to obtain 410-bp bands were as follows: 5'-TGTAGGGGAAGCCGAT-3' (LGH606) (SEQ ID NO:20) and 5'-CAATGGTGTAAGACGAGATTG-3' (LGH242) (SEQ ID NO:21).

PCR amplification was carried out with Taq DNA polymerase (Boerhinger-Mannheim) at 94° for 1 min, 48° or 54° for 1 min and 72° for 2 min over 35 cycles in a Techne-PHC3 Thermal Cycler. In most cases with cellular DNA 100 μg of template was used and 10% of the product was analysed by electrophoresis on 2.25% Nu-Sieve agarose gels (FMC, Rockland, Me.) followed by direct ethidium bromide staining and UV-photography. Nested PCR procedures were avoided to reduce the potential for contamination complications. For PCR sequencing, the size selected DNA product was recovered from the gel slice in 2.5M NaCl in TE by melting at 65° for 5 min, followed by phenol/chloroform phase extraction and precipitation with 40% isopropanol, 0.4M $NaClO_4$ and 40 μg/ml glycogen at 20° C., washing the pellet with 70% ethanol, drying and dissolving in 1×TE. The double-stranded DNA cycle sequencing system (G1BCO-BRL Life Technologies) was employed with [$^{32}$P] γ ATP-labeled primers using T4 polynucleotide kinase and analysis on 6% polyacrylamide/7M Urea gels and autoradiography.

EXAMPLE 2

Phage Lambda Library Preparation

An EMBL3A phage lambda genomic DNA library was generated directly from a Sau3A partially digested preparation of cellular DNA from an EBV plus HHV-8 positive BCBL-R tumor DNA sample after size fractionation into 15 to 20-kb segments by sedimentation in a sucrose density gradient. A second genomic library in the lambda DASHII vector was also generated from the same BCBL-R DNA sample. Two initial clones, referred to as λA12-1 and λD3-80 were detected and isolated after multiple rounds of plaque lift blot hybridization with [$^{32}$P]-labeled DNA products representing the ORF26 KS330Bam fragments described by Chang et al (19) or from a plasmid containing the TS300 PCR fragment described in the text. Four additional overlapping clones, λC2-1, λC7-1, λVR3a and λVR4a, were then selected by chromosome walking procedures. The physical maps and orientations of these clones, which contain inserts of approximately 18-kb for the λEMBL3 versions, and 12-kb for the λDASH versions were established by restriction enzyme digestion patterns and direct double-stranded primer-based DNA sequencing of the insert termini.

Subcloning and DNA Sequence Analysis

Three plasmid subclones containing adjacent 1.2 kb XhoI to EcoRI, 2.5 kb EcoRI to Eco-RI and 2.4 kb EcoRI to EcoRI fragments surrounding the TS gene locus from phage λD3-80 DNA and an adjacent 2.5 kb EcoRI to BamHI fragment plus a 6.7 kb BamHI to BamHI fragment encompassing the Bcl-2 homologue from phage λC7-1 DNA were subcloned in Bluescript plasmids and then randomly sheared and inserted into M13 for standard shotgun manual dideoxy-nucleotide sequencing analysis as described previously (47, 49). Extensions of each sequence block inwards towards a high (G+C) content heterogenous region between the BCK and IE-1B genes was carried out by direct cycle sequencing and primer walking procedures on λD3-80 and λC7-1 DNA.

DNA and protein sequence data for the HHV-8 BCBL-R genes encoding vIL-6 (U67774) (SEQ ID NO:4), DHFR (U83347) (SEQ ID NO:2), IE-1B (U83350) (SEQ ID NO:9), TS (U83348) (SEQ ID NO:1), vMIP-1B (U67775) (SEQ ID NO:6), BCK (U83351) (SEQ ID NO:7), IE-1A (U83349)

(SEQ ID NO:8), vMIP-1A (U74585) (SEQ ID NO:5) and Bcl-2 (U67773) (SEQ ID NO:3) have been filed with Genbank and are available under the listed accession numbers.

EXAMPLE 3

Detection of a Viral TS Gene in All HHV-8 Positive KS Specimens

Figure 2A:
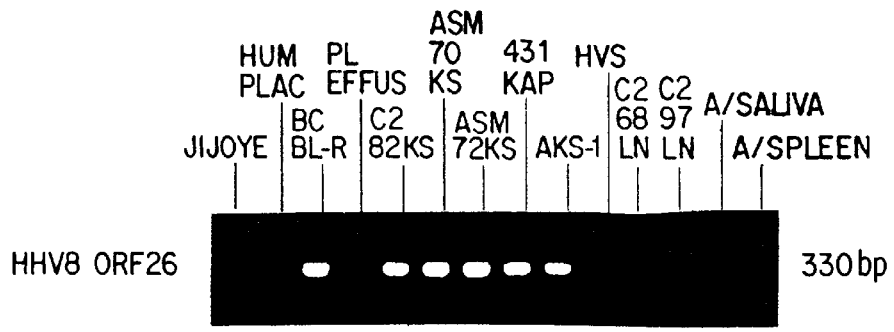
FIG. 2: Universal Presence of the HHV-8 TS Gene in Kaposi's Sarcoma DNA Samples as Detected by Direct PCR Analysis. The diagram shows ethidium bromide stained PCR product DNA bands in the appropriate selected size range after fractionation of each set of products on parallel agarose gels (panels A to F). Each reaction mixture received 100 ng of template DNA (except the BCBL-R sample) and 10% of the product DNA was applied to the gel. Samples C282, ASM70, ASM72, 431KAP and AKS1 represent KS lesions (lanes 5 to 9), samples PL/EFFUS, C268 LN, C297 LN, A/SALIVA, and A/SPLEEN represent lymph node biopsy and other control DNAs from AIDS patients (lanes 4 & 11 to 14). UPS75 (panel E) represents a primer pair from upstream of the HHV-8 ORF75 gene from BCBL-R (mapping at a position 1200 to 1500-bp to the right of the Chang 630-bp PCR region). This locus is deleted in some HHV-8 genomes including ASM70 and ASM72 (as well as in HBL6; not shown).
Figure 2B:
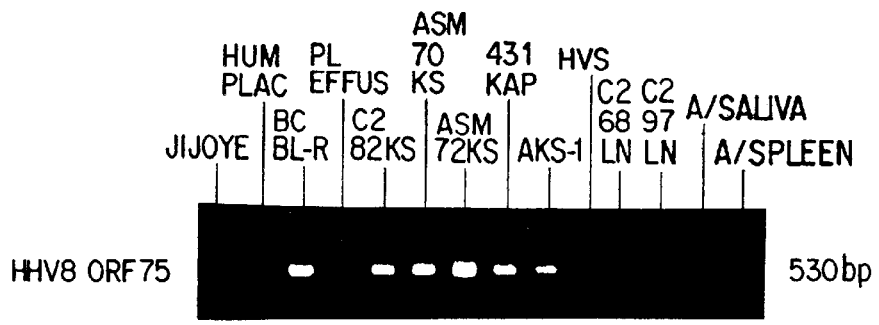
Figure 2C:
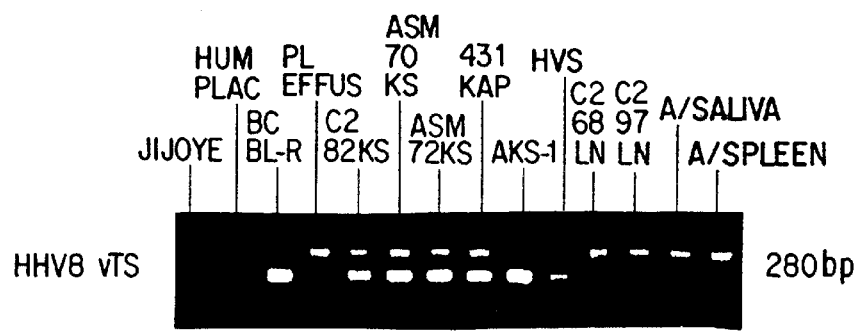
Figure 2D:
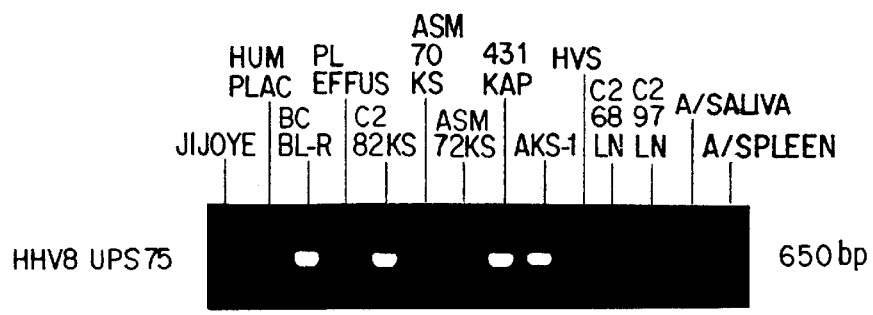
Figure 2E:
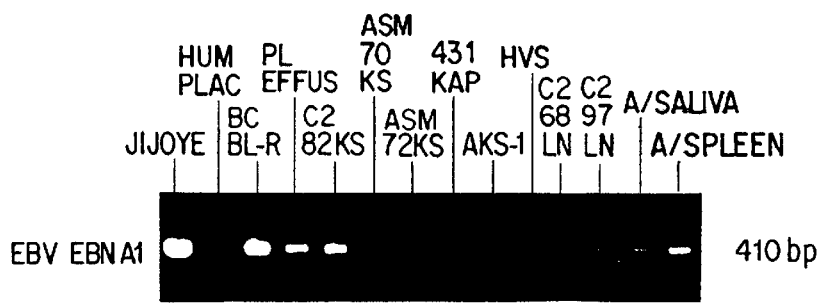
Figure 2F:
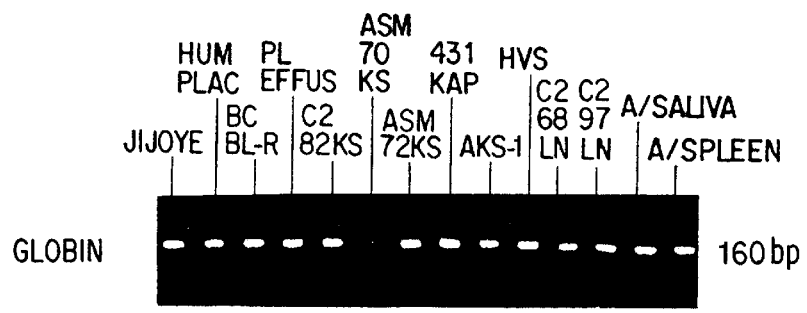

As a further test of the validity of our TS fragment as an authentic HHV-8 gene, we examined 100 ng samples of three additional known HHV-8 positive KS DNA specimens (ASM 70, ASM72, 431KAP) and a selection of negative control DNA specimens, including two lymph node biopsies from HIV positive patients with lymphadenopathy, plus human pleural effusion cell, saliva and spleen DNA from AIDS patients. Even when used at higher stringency (54° compared to the earlier 48°), which reduced the cross-over signal from HVS DNA, the HHV-8 specific TS primers (FIG. 2C) produced exactly matching 280-bp band patterns to those of both the HHV-8 ORF26 and ORF75 primers (FIGS. 2A and B) for all six positive and eight negative DNA samples tested. In comparison, the EBV EBNA-1 primers were strongly positive with Jijoye EBV, BCBL-R, C282 and one non-KS control sample and weakly positive with ASM70, whereas the other three KS samples (ASM72, 431KAP and AKS1) were negative for EBV at this level of sensitivity (FIG. 2E). All of the negative samples produced amplified globin PCR products (FIG. 2F).

Figure 3A:
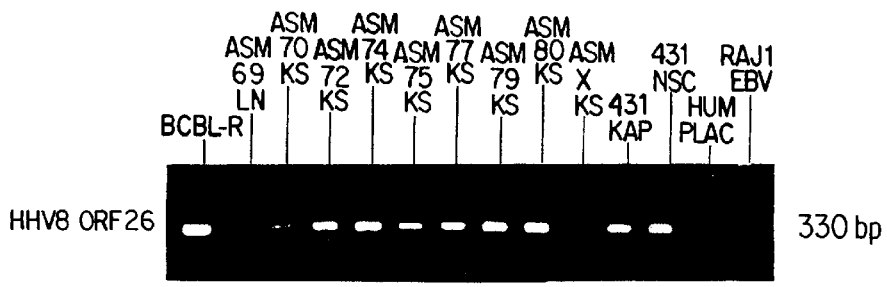
FIG. 3: Consistent Patterns of HHV-8, but not EBV Gene Fragments Detected by PCR in Multiple Disseminated KS Lesions from a Single Patient. The diagram shows direct ethidium bromide stained PCR DNA bands in the appropriate selected size range after fractionation of each set of products by electrophoresis through agarose gels (panels A to D). Samples ASM70 to ASM80 represent DNA from multiple KS lesions obtained at autopsy from lung, skin and hilar lymph node sites of a single homosexual AIDS patient in New York in 1984. Samples ASM69 and ASMX were from lymph node biopsies of other AIDS patients with lymphadenopathy in 1984. Samples 431KAP and 431NSL were obtained as skin KS and adjacent normal skin biopsies from a non-HIV associated endemic KS patient from Zaire in 1984.
Figure 3B:
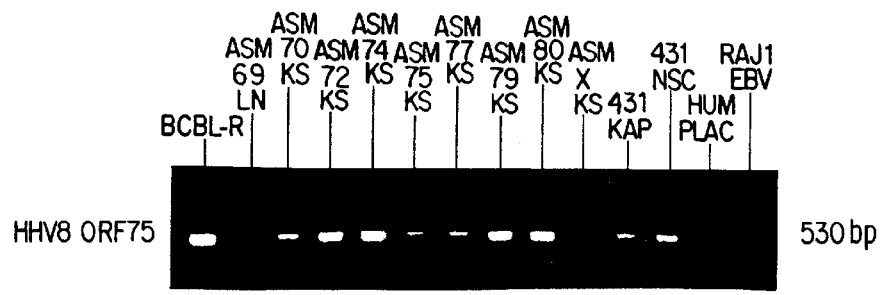
Figure 3C:
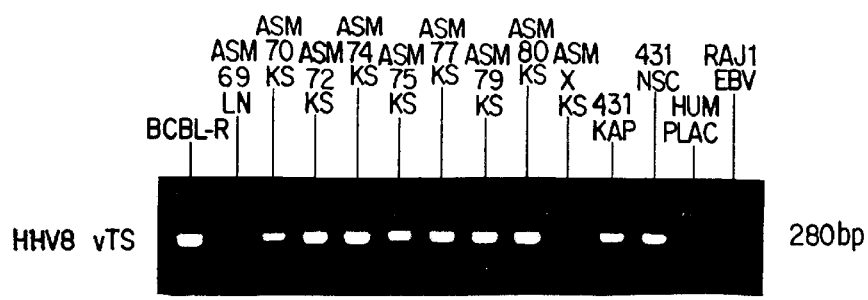
Figure 3D:
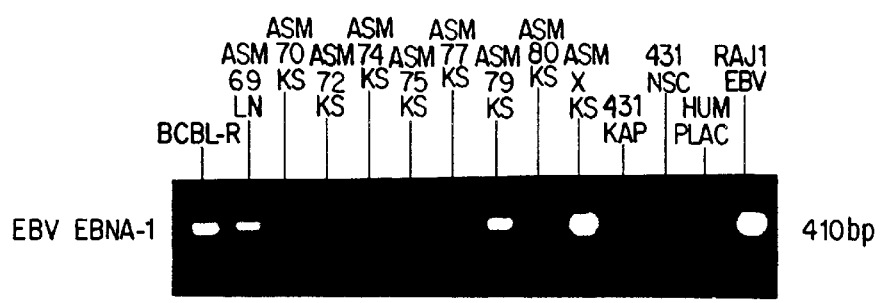

In a second comparison of this type, we screened a collection of autopsy samples from seven distinct KS lesion sites (including skin, lung and hilar lymph node) from a 1984 New York homosexual AIDS patient with aggressive disseminated disease (ASM 70 to 80). Again, all three HHV-8 PCR primers (ORF26, ORF75 and vTS) produced virtually identical patterns of positive signals in ten DNA samples, and negative results in four samples (FIGS. 3A, B & C). Amongst the seven KS lesions from the same ASM patient, four were positive for EBV EBNA-1, one strongly so (FIG. 3D, lane 8, ASM79) and three were negative. In addition, two more lymphadenopathy biopsy samples from patients later recognized to be in early stages of AIDS, were strongly positive for EBV, but were negative for HHV-8 (FIG. 3, lanes 2 & 10, ASM69, ASMX). The two other HHV-8 positive samples shown came from a Zaire non-HIV associated endemic KS lesion biopsy (431KAP), and an adjacent non-KS skin sample (431NSC) from the same patient, which were also both EBV negative (FIG. 3, lanes 11 and 12).

Overall, we have similarly detected the putative HHV-8 TS DNA fragment by direct PCR amplification in BCBL or KS DNA samples from 12/12 different patients and 22/22 distinct lesions in samples that were also positive for HHV-8 ORF26 and ORF75, but never in DNA samples that were negative for HHV-8 with the other two primer pairs. Furthermore, a second primer pair based on the original BCBL-R TS sequence gave the same results and the latter 280 bp TS PCR products also all proved to be identical by DNA sequencing in KS or BCBL samples from six different patients (not shown).

The ASM70 and ASM72 KS samples proved to be unique in that in contrast to the other KS samples tested they were both negative for amplification of the UPS75 primer pair (FIG. 2D, lanes 6 & 7), which represents a region from −860 to −210 upstream from the first ATG in the HHV-8 ORF75 coding region. We have found this region to be deleted in a subset of HHV-8 genomes, which we refer to as the C subgroup, that includes the ASM70 KS sample and the HBL6 cell line. A comparison of strain variability amongst the DNA sequences over a total of 2500-bp within the ORF26, ORF75 and UPS75 regions of each of the twelve distinct HHV-8 genomes described here is presented in the report by Zong et al (70).

EXAMPLE 4

Figure 4:
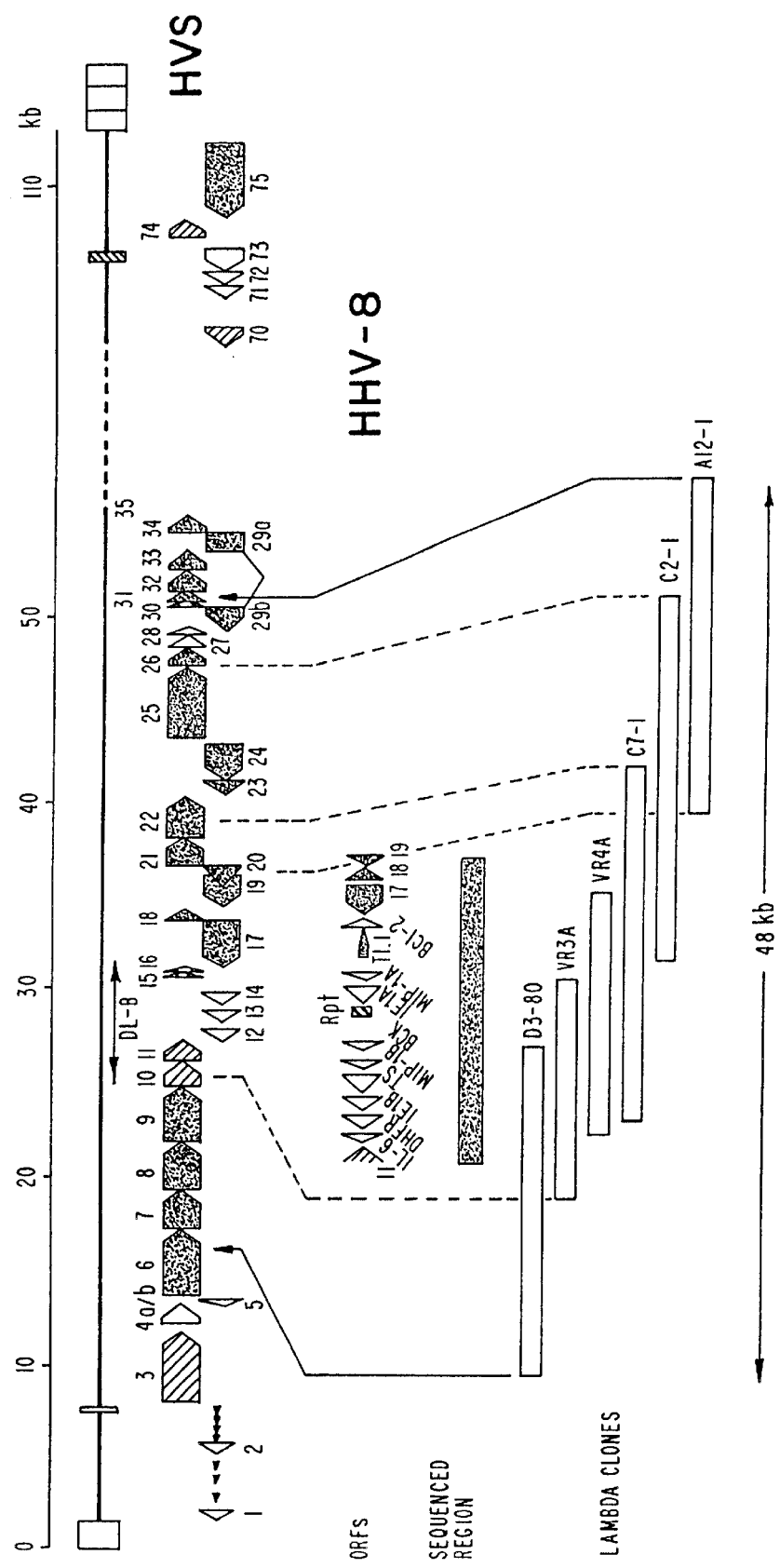
FIG. 4: Relative Map Locations Within the HHV-8 DL-B Region of the TS, DHFR, IE-1A, IE-1B and BCK-Like Genes in Comparison to other Known HHV-8 Genes and the Equivalent Locus in the HVS Genome. The upper portion (A) of the diagram illustrates the arrangement of ORFs in a contiguous 55-kb block at the left-hand end of the gamma-2 class herpesvirus saimiri genome (HVS). Solid bars refer to ORFs that are common to all known gamma herpesviruses, shaded bars indicate ORFs that are found in several gamma 2 viruses and open bars denote ORFs that are unique to HVS. The lower portion of the diagram (C) shows the relative genomic locations of six overlapping phage lambda DNA clones (λD3-80, λVR3a, λVR3b, λC7-1, λ2-1 and λA12-1) containing inserts encompassing a 48-kb segment towards the predicted left-hand end of the HHV-8 genome from the BCBL-R tumor. The sequenced DL-B block totalling 17.4 kb is shown by solid bar. The central portion of the diagram (B) details the relative positions and sizes of all of the currently recognized genes e.g. ORF10, ORF11, vIL-6, DHFR, IE-1B, TS, vMIP-1B, BCK, IE-1A, vMIP-1A, T1.1, Bcl-2 (ORF16), ORF17, ORF18 and ORF19 that map within the region encompassing divergent locus-B (DL-B) of HHV-8. IE-1A and vMIP-1A map in the same orientation as IE-1B and vMIP-1B, but both lie upstream and several kb to the right on the other side of an unstable (G+C)-rich tandem repeat region [Rpt] within λC7-1. The HVS equivalents of DHFR (ORF2) and TS (ORF70) map towards the extreme left-hand and right-hand ends of HVS, respectively. HVS ORF12 also appears to encode a PHD/LAP class zinc finger protein, and both it and the BHV-4 IE1 gene, which contains two exons with PHD/LAP finger motifs of a similar subclass, map in the same orientation as HHV-8 IE-1A and IE-1B within DL-B of those viruses.

Isolation and Sequence of Complete Genes for HHV-8 TS and DHF from a BCBL-R Genomic Phage Lambda Library A phage lambda EMBL library of size-selected partial Sau3A cleavage fragments from the same BCBL-R DNA sample described above was generated and screened for the presence of clones that hybridized with a labelled probe DNA representing a plasmid cloned sample of the original 270-bp TS PCR product. The first positive clone isolated (λD3-80) proved to contain a DNA sequence at the left-hand end that showed considerable homology to the ORF6 single-stranded DNA-binding protein genes of HVS (60% amino acid identity over positions 749 to 808 in the HVS version) and less to EHV-2 and EBV (47% and 48% amino acid identity over the same region). The 18-kb insert of this clone overlaps on the right-hand side with the left-hand end of another lambda clone (λC7-1) which also hybridized with the TS probe. This second phage clone contains a homologue of the HVS ORF22 (glycoprotein H) gene at its right-hand end and was originally selected because of overlap with two more lambda clones (λC2-1 and λA12-1) extending further to the right covering the region between ORF20 and ORF31. Overall, we generated a set of six overlapping λ clones containing a contiguous 48-kb section of the HHV-8 genome extending from ORF6 to ORF31 on the left-hand side of the genome based on the nomenclature system used for HVS (FIG. 4). Restriction enzyme mapping and end-sequence analysis of two λDASH clones λVR3A and λVR4A covering the overlap between λD3-80 and λC7-1 revealed the presence of homologues of HVS ORF10 and ORF17 and permitted us to concentrate on the predicted DL-B region.

Initial DNA sequence analysis by the M13 dideoxy shot-gun approach of a 2.5 kb EcoRI subcloned plasmid from near the right hand side of λD3-80 revealed an ORF encoding a potential 337 amino acid TS protein with homology throughout its length to previously identified viral and cellular TS enzymes (FIG. 5A). An amino acid alignment of the HHV-8 TS protein with those from HVS (12), H.ateles (HVA) (53), EHV-2 (61), varicella zoster virus (VZV) (24) and human DNA (59) revealed the closest relationship to the EHV-2 version (71% identity), slightly more divergence from the human and HVS TS proteins, and further divergence from the VZV TS protein (Table 1). Only the HVS and HVA versions are more closely related to each other.

TABLE 1

Comparison of the Overall Degree of Conservation between TS and DHFR of HHV-8 with Several Homologous Proteins

| | HVS | HVA | EHV-2 | VZV | HUMAN |
|---|---|---|---|---|---|
| (A) Thymidylate Synthetase (TS) | | | | | |
| HHV-8 | 66.4/79.5 | 65.4/78.2 | 71.6/82.7 | 61.8/78.1 | 67.3/79.2 |
| HVS | | 84.4/93.7 | 66.1/80.3 | 66.0/79.6 | 70.4/83.3 |
| HVA | | | 67.1/79.9 | 63.2/70.3 | 68.7/84.7 |
| EHV-2 | | | | 65.1/81.0 | 73.4/83.7 |
| VZV | | | | | 68.7/84.7 |

| | HVS | HUMAN | PIG | DROSOPHILA |
|---|---|---|---|---|
| (B) Dihydrofolate Reductase (DHFR) | | | | |
| HHV-8 | 48.4/65.8 | 50.0/67.0 | 48.9/65.9 | 33.7/61.1 |
| HVS | | 83.3/90.9 | 78.5/90.3 | 43.9/67.2 |
| HUMAN | | | 88.7/95.2 | 44.8/69.1 |
| PIG | | | | 47.5/68.0 |

Values for percent identity (left) and percent similarity (right) of amino acid residues were derived from the output of GAP pairwise alignments with gap and length weights set at 3.0 and 0.1, respectively.

DNA sequence analysis of an adjacent 2.4 kb EcoRI fragment subclone to the left of the TS gene within λD3-80 also revealed an HHV-8 gene encoding a complete 212 amino acid homologue of the HVS (62) and mammalian dihydrofolate reductase (DHFR) proteins (FIG. 5B). However, the HHV-8 DHFR is highly diverged from both the *H.saimiri* and mammalian versions. For example, HVS DHFR is 83% identical at the amino acid level to human DHFR and 78% identical to pig DHFR (59). In comparison, HHV-8 DHFR shows only 49% identity to the HVS, human and pig DHFR proteins, which is about an equivalent level of divergence as between the mammalian and Drosophila versions (Table 1). Furthermore, the residual homology to our original DHFR conserved primers proved to be far too low for the redundant PCR approach to have succeeded.

EXAMPLE 5

HHV-8 and HVS Encode Homologues of the BHV-4 IE1 Zinc Finger Protein

An HHV-8 version of another recognizable gamma class herpesvirus gene was also found within the DNA sequence between the DHFR and TS genes. This ORF potentially encodes a 333 amino acid protein (FIG. 6A) with a zinc-finger motif that resembles the prototype C3HC4 RING class zinc-finger motifs found in the herpes simplex virus IE110 (or ICP0) transactivator protein (27, 28, 51). However, the HHV-8 protein proved to be a variant of the newly recognized $C_4HC_3$ PHD/LAP class of zinc-finger motif (1, 55), which is most closely related to similar motifs in the IE1 protein of the bovine gamma-2 class herpesyims BHV-4 (64). The BHV-4 major IE1 protein gene lies in the same orientation within the DL-B region of that virus and is encoded by a spliced four exon mRNA (64).

Subsequently, we also detected another upstream HHV-8 ORF mapping several kilobases to the right, but still within DL-B of λC7-1 that is predicted to encode a 256 amino acid protein (FIG. 6A) with a second diverged copy of this same PHD/LAP subclass of zinc-finger motif Further analysis revealed that BHV-4 also has a second duplicated but diverged copy of a PHD/LAP zinc finger motif in a potential downstream fifth exon of the IE1 gene, and that the positionally analogous 169 amino acid ORF12 protein of HVS also contains a closely related PHD/LAP class zinc finger motif. By analogy with BHV-4, we refer to these two HHV-8 ORFs as IE-1B and IE-1A. Both of the HHV-8 IE1-like genes contain intact ORFs with associated ATG codons towards their 5'-ends, but the presence of excellent consensus splice acceptor motifs just upstream of their ATGs suggest that each may also be a component of a larger complex spliced transcript with upstream exons. A comparison alignment of the predicted IE-A and IE-B proteins revealed approximately 40% amino acid identity between the two (FIG. 6A). Sequencing of PCR products obtained from HBL6, C282, 431KAP and AKS1 DNA confirmed the presence of virtually identical IE-1B regions in all five HHV-8 positive samples tested from both BCBL and KS sources.

Alignments of both PHD/LAP1 zinc-finger motifs from HHV-8 with the two BHV-4 IE1 and the HVS ORF12 motifs, and a comparison with six other known motifs of this type including one from *S. cerevesiae* yeast (SMM4) and three from *C.elegans*, together with those in the C7 protein in swine pox virus (40) and the ZYS-1A and ZYS-1B proteins of Chiamydomonas (63) are shown in FIG. 7A. In all eleven of these proteins the LAP zinc finger motif is located close to the N-terminus, and we have tentatively placed them into a distinct subclass of LAP finger motifs with a central $CXCX_{4-7}H$ structure between C-3 and H-5 positions, compared to representatives of the majority of the PHD/LAP motifs, exemplified by HUMAF10 and HUM-MLLa (55), which have $CX_{2-4}CX_4H$ in this region (FIG. 7B). The RING zinc finger motifs of HSV ICP0, and the cellular RAG-1 protein and the PML and BRCA-1 proto-oncogene proteins are also shown for comparison (FIG. 7C). All five of the gamma-2 herpesvirus IE1-like ORFs also contain at least three internal hydrophobic domains, suggesting that they may be membrane proteins rather than typical hydrophilic IE class nuclear transactivators.

EXAMPLE 6

A Fourth Potential Cytokine Gene and the T1.1 Nuclear RNA also Map Within DL-B

Virtually complete DNA sequence analysis of a 17-kb block encompassing the whole of the DL-B region of HHV-8 revealed fourteen ORFs with clearly recognizable features. The flanking sections contained well-conserved homologues of HVS ORF10 and ORF11 on the left hand side and of ORF17, ORF18 and ORF19 on the right hand side. ORF6 to ORF9 and ORF17 to ORF19 are found at equivalent locations in all gamma herpesviruses, whereas ORF10 and ORF11 are present in HVS and in EHV-2, but are absent in EBV. As described elsewhere (21), a rightwards oriented but highly diverged HHV-8 homologue of HVS ORF16 proved to contain motifs characteristic of the human Bcl-2 family of anti-apoptosis proteins. Furthermore, despite showing only 15 to 20% overall amino acid identity to several cellular members of the Bcl-2 family, as well as to EBV BHRF1 and HVS ORF16, the HHV-8 homologue of Bcl-2 proved to be functionally active in blocking apoptosis induced by Sindbis virus infection (21).

Amongst the eight other recognizable homologues of cellular genes in HHV8 DL-B (six of which are either not encoded by or are not present at this location in the HVS genome), all mapped in the leftward orientation between ORF11 and ORF16 (Bcl-2), in the following order from left to right: vIL6, DHFR, IE-1B, TS, vMIP-1B, BCK (β-chemokine-like), IE-1A and vMIP-1A (FIG. 4). Identification of the vIL-6, vMIP-1A and vMIP-1B genes, which potentially encode proteins with between 25 and 40% identity to human IL-6 and MIP-1α or MIP-1β respectively, and evidence for functional activity of vIL-6 has been presented elsewhere (50). The predicted BCK-like protein of 114 amino acids (FIG. 6B) represents a third potential HHV-8 encoded β-chemokine with a fairly typical $CCX_{15}CX_{22}C$ cysteine bridge pattern (8) and a probable hydrophobic N-terminal signal peptide region, but unlike the two vMIP-1 proteins, it shows only low level homology to several of the closest known cellular members of this family (such as MIP-1α, RANTES, TAC-2, MCP-1, and CC; FIG. 6B). Conservation of the cysteine bridge pattern between HHV-8 encoded vIL-6 and human IL-6 is also illustrated in FIG. 6C. The 2.7-kb divergent region between vMIP-1A and Bcl-2 (FIG. 4) appears to contain multiple transcriptional control elements, which are in the process of being characterized (Chiou, C.-J. and Hayward, G. S., unpublished data), as well as a rightwards-oriented gene lying just upstream from the Bcl-2 homologue that encodes the abundant 1.1-kb lytic cycle nuclear RNA (T1.1) described by Zhong et al (69). Finally, a central approximately 3.4-kb region between BCK and IE-1A contains another complex region with multiple binding motifs and two sets of 20-bp and 30-bp high (G+C) repeats totalling up to 630-bp that tend to delete in λ clones (denoted by Rpt in FIG. 4).

Figures 8A, 8B:
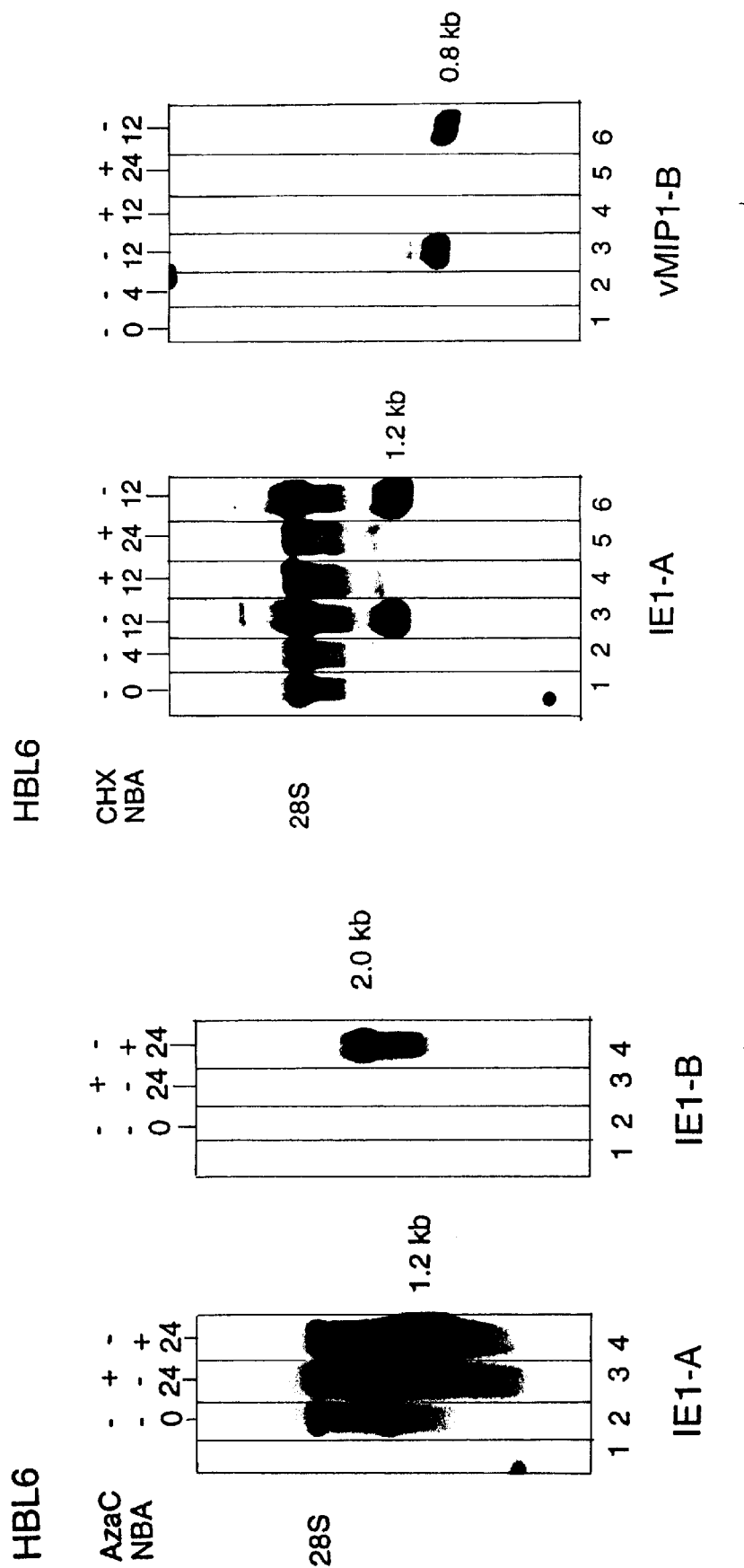
FIG. 8: Detection of HHV-8 IE-1A, IE-1B and vMIP-1B mRNA Transcripts in a Butyrate Induced BCBL Cell Line. The autoradiographs show the results of Northern blot hybridization analysis of whole cell RNA samples from HBL6 cells using antisense riboprobes generated against the coding regions of HHV-8 IE-1A, IE-1B and vMIP-1B. (A) Induction of both IE-1A and IE-1B mRNA with butyrate (NBA) but not with 5-azacytidine (aza-C). LHS panel. IE-1A riboprobe. RHS panel. IE-B riboprobe. Lane 1, No RNA; 2, uninduced HBL6 RNA; 3, 5-Azacytidine treatment for 24 h; 4, NBA treatment for 24 h. Note that the IE-1A probe showed some cross-reaction with the 28S ribosomal RNA band in these experiments. (B) Induction of both IE-1A and vMIP-1B mRNA by NBA treatment is blocked in the presence of cycloheximide (CHX). LHS panel, IE-1A riboprobe. RHS panel vMIP-1B riboprobe. Lane 1, uninduced HBL6 RNA; 2, NBA induction for 4 h; 3 NBA induction for 12 h; 4 , NBA induction for 12 h plus CHX; 5, Butyrate induction for 24 h plus CHX; 6, NBA induction for 12 h (duplicate RNA sample).

EXAMPLE 7
Identification and Expression of mRNAs in Butyrate Induced BCBL Cells Although KS-derived spindle cell lines do not contain HHV-8 DNA (38), several cell lines from BCBL tumors that do stably maintain both HHV-8 and EBV DNA have been described (16, 17, 45). We have used the HBL6 subline of BC-1 cells to examine whether or not transcripts for some of the genes described here could be detected. Anti-sense riboprobes for IE-1A, IE-1B, vMIP-1B and DHFR were generated and used for Northern blot hybridization with total cell RNA prepared from HBL6 cells both before and after attempts to induce the lytic cycle with agents that are effective with some EBV cell lines. Initial experiments revealed that an abundant IE-1A mRNA species of 1.2-kb, and a less intense IE-1B mRNA species of 2.0-kb were expressed after treatment with butyrate, but not with TPA or 5-azacytidine and not in untreated cells (FIG. 8A). Others have also reported that TPA fails to induce HHV-8 lytic cycle expression in BC-1 cells, but that butyrate does do so (44, 45). We also found a single transcript of 0.8-kb for MIP-1B in HBL6 cells at 12 h after butyrate induction, but not in uninduced cells. Both the IE-1A and vMIP-1B mRNAs were absent at 4-h after butyrate treatment and their synthesis was blocked in the presence of cyclohexirnide for either 12 or 24 h (FIG. 8B, lanes 3 and 6). Single transcripts of 1.1-kb corresponding to HHV-8 DHFR mRNA (FIG. 9B) and of 1.0-kb corresponding to vIL-6 mRNA (50) were also detected after butyrate induction. A time course experiment showed that neither the IE-1A nor DHFR transcript was detectable at 4 or 8 h after butyrate addition, but that they both peaked at 12 h and declined considerably by 24 h and 48 h after induction (FIGS. 9A and 9B). Again, addition of cycloheximide also completely blocked expression of DHFR mRNA in 12 h butyrate-induced cells (not shown). Exactly analogous results have also been obtained with RNA after butyrate induction of the HHV-8 positive, but EBV negative, BCBL-1 cell line (FIG. 9C). Therefore, each of the genes tested gives rise to a distinct transcript and they all appear to represent primarily lytic cycle rather than latently expressed genes.

Northern Blot mRNA Analysis

The HBL6 subclone of BC-1 cells derived from a human BCBL/PEL tumor containing both HHV-8 and EBV genomes (16) was grown in RPMI medium plus 20% fetal calf serum. Induction treatments involved addition of either 4 mM sodium butyrate or 5 $\mu$M 5-azacytidine at the 0 h time point. In some cultures, cycloheximide was added at 50 $\mu$g/ml at the time of induction to block protein synthesis. Cells were harvested at various time points and total cell RNA was extracted with Trizol (BRL, Bethesda). RNA samples (5 $\mu$g/well) were subjected to electrophoresis on 2% formaldehydel/0.9% agarose gels in MOPS buffer (20 mM MOPS, pH7.0, 10 mM NaOAc, 2 mM EDTA) and transferred to nylon membranes (S and S Nytran) by capillary transfer. Hybridization was carried out at 68° overnight in 6×SSC, Denhardts and 0.1% SDS with $10^6$ cts/min/ml of [$^{32}$P]-labeled riboprobes generated by in vitro synthesis with T7 or SP6 RNA polymerase from appropriate plasmid DNA templates. All four intact ORF riboprobe template plasmids represented PCR DNA products derived from λD3-80 or λC7-1 subcloned into the pGEM (IE-1A and IE-1B, SP6), Bluescript KS (vMIP-1B, T7) or pSG5 (DHFR, T7) vectors.

EXAMPLE 8
Biological Activity of vIL-6

To examine whether vIL-6 specifies a functional gene product with properties analogous to those of human IL-6, we utilized the murine hybndoma cell line B9 that has been shown previously to be dependent on IL-6 for growth. Both murine and human IL-6 are effective in supporting B9 growth. Rat embryo fibroblast (REF) cells were transfected with expression plasmids containing vII-6 ORF sequences in the positive (pvIL6) or negative (pvIL-6neg) orientations relative to the human cytomegalovirus promoter-enhancer, and supernatants were harvested between 2 and 4 days posttransfection. Various dilutions of the extracts were made and assayed for IL-6 activity relative to recombinant human IL-6 (rhIL-6). The results shown in FIG. 10 indicate that the vIL-6 gene product is capable of supporting the growth of B9 cells and therefore that it displays functional activity analogous to human and murine IL-6. The receptor for human IL-6 has been identified as an 80 kD protein (IL-6R) that, when bound to IL-6, associates with a transmembrane protein, gp130, thought to represent the signal transducer. Utilizing a functionally neutralizing monoclonal antibody directed against the murine IL-6R (D7715A7, Pharmigen), we repeated the B9 assays in the presence or absence of the antibody to determine if IL-6R played a role in mediating the observed vIL-6 activity. The results (Table 2) show that the anti-IL-6R antibody inhibited both vIL-6 and rhIL-6 activity in the B9 assay, indicating that this function is mediated through the same signal transduction pathay utilized by endogenous IL-6. A monoclonal antibody directed against murine IL-2 (S4B6, Pharmigen) had no effect on vIL-6 function in parallel assays (Table 2).

Figure 10A:
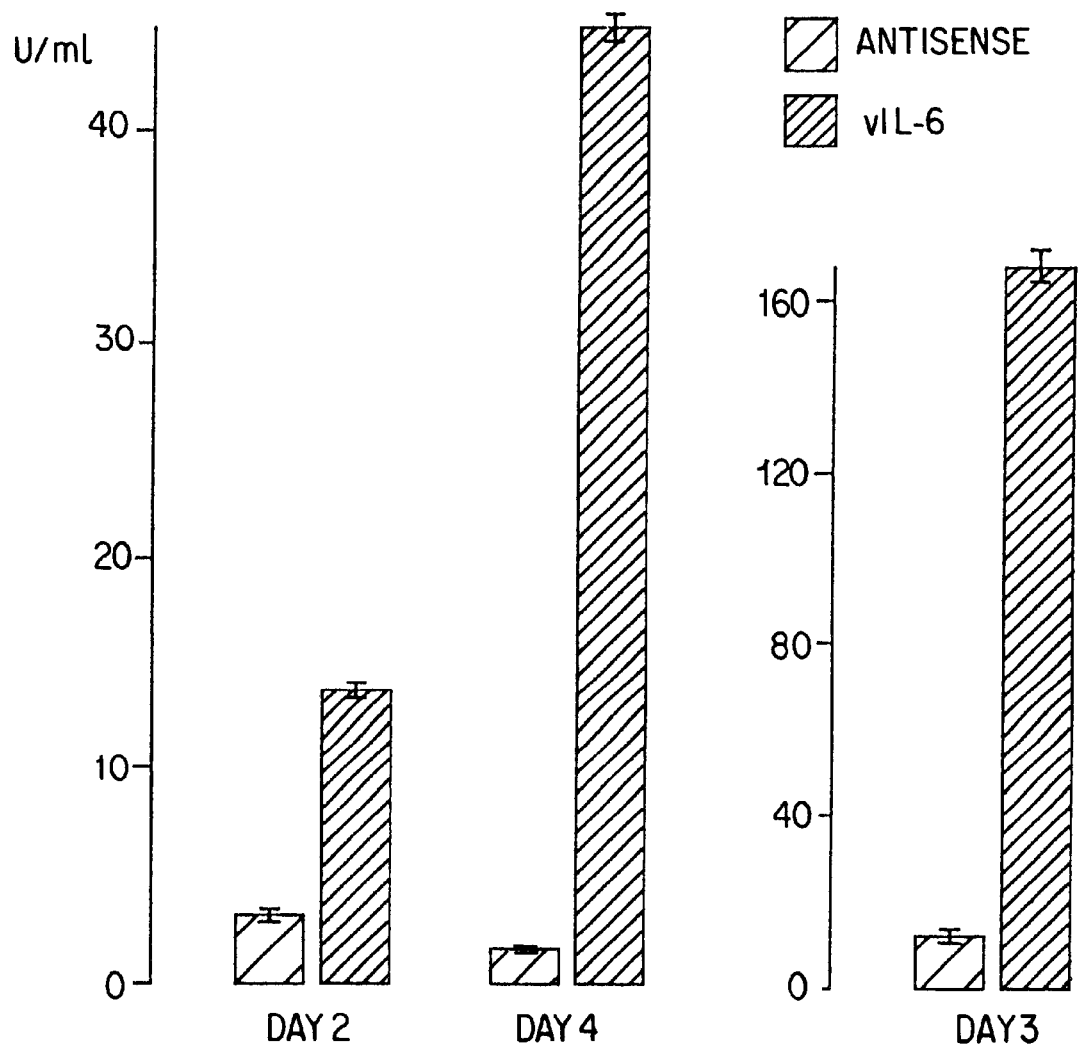
FIG. 10: Assays for biological activity of HHV-8 encoded vIL-6. (A) Diluted culture medium from REF cells transfected with the vIL-6 expression plasmid pvIL-6, or with a negative control plasmid containing the vIL-6 ORF in the antisense orientation relative to the CMV promoter-enhancer in the pcDNA3 vector (pvIL-6neg), were assayed for IL-6 activity in promoting the growth of B9 cells as described in Materials & Methods. Recombinant human IL-6 (rhIL-6) was used as a positive control (data not shown) and to enable the calculation of the activity (U/ml) of vIL-6. Transfected REF cell medium containing vIL-6 was harvested either at 2 and 4 days posttransfection (experiment 1, left) or at 3 days posttransfection (experiment 2, right). For each supernatant dilution used, the assays were performed in quadruplicate. (B) Hep3B cells were grown in 25 cm$^2$ flasks and transfected with 10 μg of pSG5 (empty vector), pSVvIL-6 (vIL-6 expression vector), pvIL-6, or pvIL-6neg. Other Hep3B cells were either untreated ("medium") or treated with 500U/ml rhIL-6 (Gibco-BRL). After 48 h, the cells were harvested, 5 μg total cell RNA per sample was size fractionated for northern blot analysis, and membranes were hybridized with $^{32}$P-radiolabelled $\alpha_1$-acid glycoprotein (AGP) probe DNA sequences. The positions of 28S and 18S ribosomal markers and the estimated size of the detected AGP transcripts are indicated.
Figure 10B:
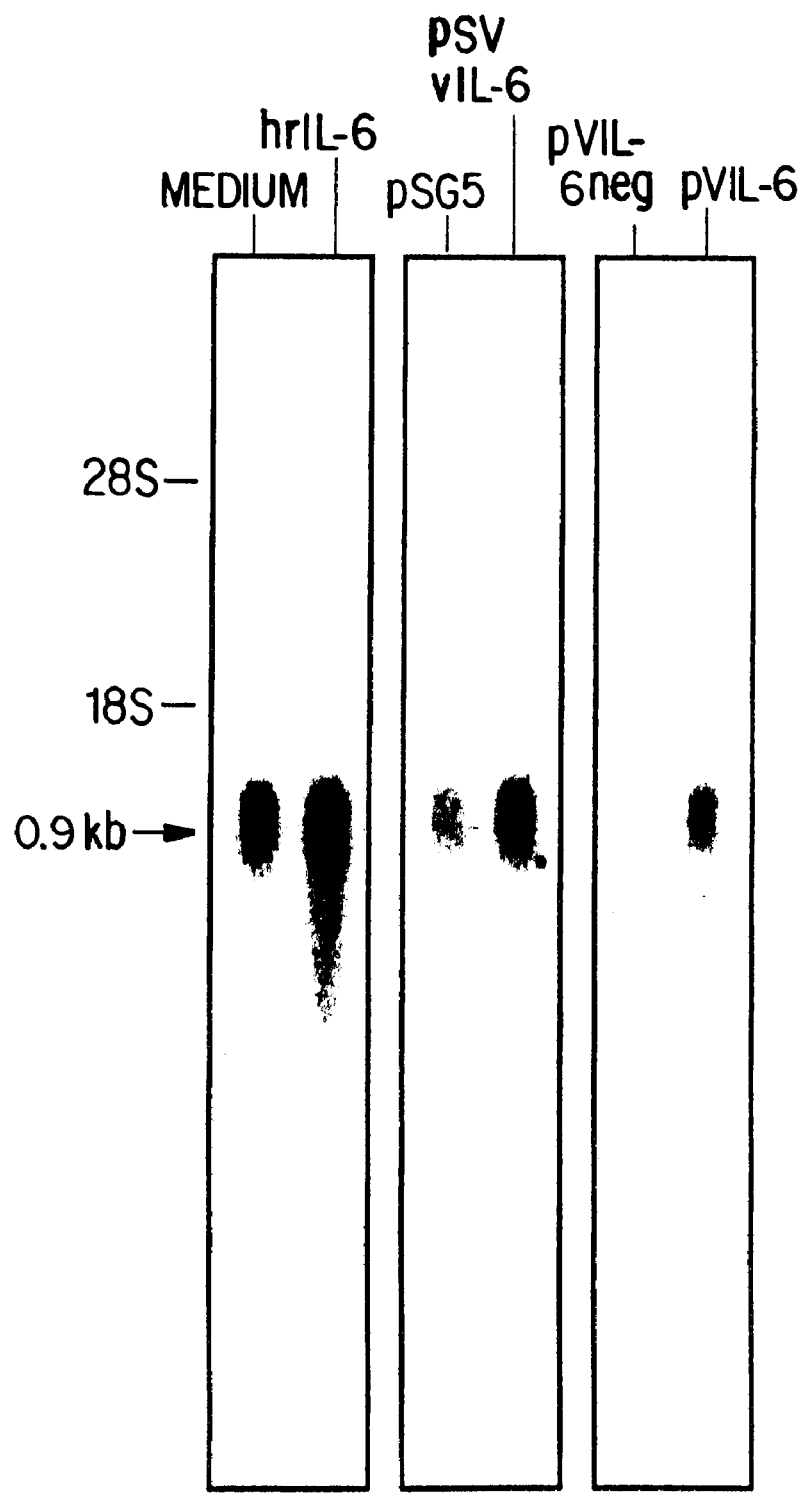

To demonstrate further the functional equivalence of vIL-6 to endogenous IL-6, we also examined the ability of vIL-6 to induce the expression of a representative acute-phase gene, $\alpha_1$-acid glycoprotein (AGP), in the hepatoma cell line Hep3B. Human IL-6 is known to mediate the induction of acute-phase mRNA and protein synthesis in hepatocytes, and this effect is mediated in part through the activation of a nuclear factor that binds to common promoter elements of these genes. To determine whether vIL-6 also displays this property, we transfected Hep3B cells with either of two vIL-6 expression vectors (pvIL-6 or pSVvIL-6), or with appropriate negative control plasmids, and harvested the cells for RNA 48 h posttransfection. RNA was also harvested from untreated or rhIL6-treated Hep3B cells for comparison. Northern blot hybridization analysis was undertaken to determine the relative levels of AGP mRNA present in the cells (FIG. 10). The results revealed that AGP mRNA levels were induced in response to vIL-6 as well as by rhIL-6, demonstrating the functional equivalence of the viral and endogenous human IL-6 cytokines for this activity.

We have demonstrated here that HHV-8 encoded vIL-6 is functionally equivalent to human IL-6 in supporting B9 cell growth and activating acute-phase gene expression in vitro. It is also possible that vIL-6 specifies other, in vivo functions analogous to endogenous IL-6, and that it could be involved in KS, Castleman's disease, and other malignancies. The potential role of vIL-6 in KS in particular, could in principle be mediated through expression of this protein during either latent or lytic infection in affected tissues.

vMIP-1 (A and/or B) could also play a role in HHV-8-associated disease, perhaps cooperatively with hIL-6/vIL-6, by effecting local increases in cytokine levels by recruitment of cytokine-producing cells into infected tissues. It can also be postulated that the vMIP-1 proteins may have a more direct role in effecting cellular proliferation by acting as mitogens, since MIP-1α transcripts have been detected at high levels in human leukemic cells, suggesting a potential involvement of this cytokine in neoplastic transformation. Therefore, the presence of vIL-6 and vMIP-1 genes in HHV-8 may be directly relevant to cellular transformation and the proliferation characteristics of the cells with which the virus is associated. Furthermore, since human MIP-1α, MIP-1β and RANTES all compete with HIV gp120 for binding to T-cells, and each can both block HIV entry into T-cells as well as stimulating HIV growth in macrophages, there appears to be great potential here for reciprocal interactions between HIV and HHV-8 that could influence the progression of AIDS in patients infected with both viruses.

Cloning and Expression of vIL-6

The coding region of vIL-6 was obtained by PCR amplification of appropriate sequences from the lambda phage clone D3-80 using oligonucleotide primers directed to the 5' and 3' ends of the vIL-6 ORF and containing BamHI sites within 5' non-complementary sequences. The vIL-6 ORF was cloned as a BamHI fragment into the BamHI site of the eukaryotic expression vectors pcDNA.3 and pSG5 (Stratagene, Inc.). Plasmids containing vIL-6 coding sequences in the correct (pvIL-6) and negative (pvIL-6neg) orientations relative to the HCMV promoter-enhancer and 3' processing/polyadenylation signals in pcDNA.3 were obtained. The plasmid pSVvIL-6 contains the vIL-6 ORF expressed under the control of the SV40 promoter in the vector pSG5. Rat embryo fibroblast cells (REF) were grown MEM containing 10% fetal calf serum (PCS), and transfected with 5 μg of either pvIL-6 or pvIL-6neg by calcium phosphate coprecipitation. Supernatants were harvested 2 to 4 days posttransfection for IL-6 functional assays using IL-6 dependent B9 cells. Hep3B cells grown in MEM/10% FCS and were transfected with 10 μg of pvIL-6, pvIL-6neg, pSVvIL-6, or pSG5 and harvested 48 h posttransfection in assays to measure AGP induction as a function of vIL-6.

Assay for IL-6 Function

The IL-6 dependent murine cell line B94 was obtained from L. Aarden and was maintained in RPMI supplemented with 10% fetal calf serum and 100 U/ml IL-6. Supernatants from vIL-6-transfected cultures were diluted in RPMI/10% FCS and 100 μl containing 2×10$^5$ B9 cells in log phase growth added in quadruplicate to 96 well plates. After 72 h at 37° C., 20 μl of 5 mg/ml MTT was added to each well and the cultures incubated for a further 4 h. 75 μl of a solution containing 20% SDS, 50% DMF (pH4.7) was then added to each well and the plates incubated in the dark overnight at room temperature to dissolve the crystals. O.D.$_{570}$ readings were taken. Values in units were obtained by selecting dilutions of culture supernatants giving linear results and interpolating on a linear portion of a standard curve. Assays in which antisera to IL-6R or gp130 were used were carried out similarly and were performed in duplicate. Rat monoclonal antibodies to murine IL-6R (IgG$_{2b}$) and murine IL-2 (IgG$_{2a}$) were obtained from Pharmingen (cat# 18400D and 18000D, respectively).

TABLE 2

Inhibition of vIL-6 activity by anti-IL-6R monoclonal antibody.

| 10 pg/ml hIL-6 | Absorbance$_{570}$ | % Inhibition | 10 pg/ml hIL-6 | Absorbance$_{570}$ | % Inhibition |
|---|---|---|---|---|---|
| (a) hIL-6 | | | | | |
| 0.0 μg/ml αIL6R | 0.453 ± 0.034 | — | 0.0 μg/ml αIL2 | 0.453 ± 0.034 | — |
| 2.5 μg/ml αIL6R | 0.182 ± 0.023 | 59.2 | 2.5 μg/ml αIL2 | 0.371 ± 0.011 | 17.5 |
| 5.0 μg/ml αIL6R | 0.139 ± 0.021 | 68.7 | 5.0 μg/ml αIL2 | 0.371 ± 0.022 | 17.3 |
| 10.0 μg/ml αIL6R | 0.089 ± 0.014 | 80.0 | 10.0 μg/ml αIL2 | 0.342 ± 0.043 | 23.4 |
| (b) vIL-6 | | | | | |
| 0.0 μg/ml αIL6R | 0.420 ± 0.030 | — | 0.0 μg/ml αIL2 | 0.420 ± 0.030 | — |
| 2.5 μg/ml αIL6R | 0.277 ± 0.005 | 33.7 | 2.5 μg/ml αIL2 | 0.380 ± 0.016 | 9.5 |
| 5.0 μg/ml αIL6R | 0.229 ± 0.003 | 45.2 | 5.0 μg/ml αIL2 | 0.398 ± 0.022 | 8.2 |
| 10.0 μg/ml αIL6R | 0.193 ± 0.001 | 53.8 | 10.0 μg/ml αIL2 | 0.364 ± 0.009 | 12.8 |

Note: The table header uses "1:40 vIL-6 sup" in the continued portion.

B9 cell proliferation assays were carried out essentially as described in the legend to FIG. 10 either in the absence or presence of added monoclonal B9 cell proliferation assays were carried out essentially as described in the legend to FIG. 10 either in the absence or presence of added monoclonal antibody (2.5 to 10.0 μg/ml) to the murine IL-6 receptor or murine IL-2 (negative control). Data are derived from MTT assays performed in triplicate for each sample and are presented with B9 proliferation set at 100% in the absence of antibody and 0% is the value obtained when medium lacked the addition of reference IL-6 (rhML-6) or transfected cell supernatant (vIL-6). Activities of rhIL-6 and vIL-6 used in these assays were comparable to those obtained previously (FIG. 10).

EXAMPLE 9

Overexpression of KSbcl-2 Inhibits Sindbis Virus-Induced Apoptosis

Sindbis virus, an alphavirus, has been shown to induce typical apoptosis. We have established a Sindbis virus vector system to test the ability of candidate death-regulatory genes to delay or accelerate Sindbis virus-induced apoptosis. The putative KSbcl-2 coding sequence with a N-terminal HA-tag was cloned into the Sindbis virus vector. KSbcl-2 provided to be equivalent to Bcl-2, Bcl-x$_L$ and BHRF1 in its ability to inhibit Sindbis virus-induced apoptosis as indicated by approximately 50% cell viabilities at 48 hours post-infection compared to 2–3% with an irrelevant gene (CAT) or with KSbcl-2 in the reverse orientation. We and other have shown that the HA-tag has no effect on the anti-apoptotic activity of Bcl-2 homologs. To verify the expression of KSbcl-2 protein, infected cell lysates were analyzed by immunoblotting with anti-HA antibodies. A protein of 24 kD) was observed only in cells infected with the recombinant virus encoding KSbcl-2. To assess the role of the BH3 domain in the death-suppressor activity of Bcl-x$_L$, amino acid substitutions were introduced into the Bh3 domain of Bcl-x$_L$ (Glu to Gin change at residue 92, Asp to Ala change at residue 95 and Glu to Asp change at residue 96) and the anti-death function was assayed using the Sindbis virus vector system. The BH3 mutant was as efficient as wild-type Bcl-x$_L$ at inhibiting apoptosis, indicating that BH3 may not be directly involved in the death-suppressor activity of Bcl-x$_L$.

Production of Recombinant Sindbis Virus dsSV vectors containing KSbcl-2 in both orientations, chloramphenicol acetyltransferase (CAT), bcl-2, bcl-x$_L$, BHRF1, or the BH3 mutant of bcl-x$_L$ were each linearized with Xho 1 and in vitro transcribed using SP6 RNA polymerase. Stocks of recombinant viruses were generated by transfecting the infectious RNA into BHK (baby hamster kidney) cells and collecting the supernatant at 24 h post transfection. Virus titers were determined by standard plaque assays.

Cell Viability and Immunoblotting

BHK cells were infected with different recombinant dsSV viruses at a multiplicity of infection (MOI) of 5 plaque forming units per cell, and cell viability was determined by the trypan blue exclusion method at 48 h post-infection. At 16 h post-infection cell lysates were prepared from BHK cells infected with recombinant viruses at a MOI of 5 and were immunoblotted with 12CA5 anti-HA antibody (Berkeley) and detected by ECL (Amersham).

REFERENCES

1. Aasland, R., T. J. Gibson, and A. F. Stewart. 1995. The PHD finger: implications for chromatin-mediated transcriptional regulation. Trends Biochem. Sci. 20:56–59.
2. Albini, A., G. Bariliari, R. Benelli, R. C. Gallo, and B. Ensoli. 1995. Angiogenic properties of human immunodeficiency virus type 1 Tat protein. Proc. Natl. Acad. Sci. USA. 92:4838–4842.
3. Albrecht, J.-C., and B. Fleckenstein. 1990. Structural organization of the conserved gene block of herpesvirus saimiri coding for DNA polymerase, glycoprotein B, and major DNA binding protein. Virology. 174:533–542.
4. Albrecht, J.-C., J. Nicholas, D. Biller, K. R. Cameron, B. Biesinger, C. Newman, S. Wittmann, M. A. Craxton, H. Coleman, B. Fleckenstein, and R. W. Honess. 1992. Primary structure of the herpesvirus Saimiri genome. J. Virol. 66:5047–5058.
5. Ambinder, R. F., C. Newman, G. S. Hayward, R. Biggar, M. Melbye, L. Kestens, E. Van Marck, P. Piot, P. Gigase, P. B. Wright, and T. C. Quinn. 1987. Lack of association of cytomegalovirus with Endemic African Kaposi's Sarcoma. J. Infect. Dis. 156:193–197.
6. Ambrozia, J. A., D. J. Blackbourn, B. G. Herndier, R. G. Glogan, J. H. Gullett, A. R. McDonald, E. T. Lennette, and J. A. Levy. 1995. Herpes-like sequences in HIV-infected and uninfected Kaposi's sarcoma patients. Science. 268:582–583.
7. Baer, R., A. T. Bankier, M. D. Biggin, P. L. Deininger, P. J. Farrell, T. J. Gibson, G. HatfAll, G. S. Hudson, S. C. Satchwell, C. Seguin, P. S. Tufflnell, and B. G. Barreil. 1984. DNA sequence and expression of the B95-8 Epstein-Barr virus genome. Nature (London). 310:207–211.
8. Baggiolini, A, B. Dewald, and B. Moser. 1994. Interleukin-8 and related chemotactic cytokines—CXC and CC chemokines. Advances in Immunology. 55:97–179.
9. Bankier, A. T., W. Dietrich, R. Baer, B. G. Barrell, F. Colbere-Garapin, B. Fleckenstein, and W. Bodemer. 1985. Terminal repetitive sequences in herpesvirus saimiri virion DNA. J. Virol. 55.
10. Beral, V., T. A. Peterman, R. C. Berkelman, and H. W. Jaffe. 1990. Kaposi's sarcoma among persons with AIDS: a sexually transmitted infection? Lancet. 335:123–128.
11. Biesinger, B., I. Muller-Fleckenstein, B. Simmer, G. Lang, S. Wittmann, E. Platzer, R- C. Desrosiers, and B. Fleckenstein. 1992. Stable growth transformation of human T lymphocytes by herpesvirus saimiri. Proc. Natl. Acad. Sci. USA. 89:3116–3119.
12. Bodemer, W., H. H. Niller, N. Nitsche, B. Scholz, and B. Fleckenstein. 1986. Organization of the thymidylate synthase gene of herpesvirus saimiri. J. Virol. 60:114–123.
13. Boshoff, C., S. Talbot, M. Kennedy, J. O'Leary, T. Schulz, and Y. Chang. 1996. HHV8 and skin cancers in immunosuppressed patients. Lancet. 347:338–339.
14. Browning, G. F., and M. J. Studdert. 1989. Physical mapping of a genome of equine herpesvirus 2 (equine cytomegalovirus). Arch. Virol. 104:77–86.
15. Bublot, M., P. Lamonte, A.-S. Lequarre, J.-C. Albrect, J. Nicholas, B. Fleckenstein, P.-P. Pastoret, and E. Thiry. 1992. Genetic relationships between bovine herpesvirus 4 and gammaherpesviruses Epstein-Barr virus and herpesvirus saimiri. Virology. 190:654–665.
16. Cesarnan, E., Y. Chang, P. S. Moore, J. W. Said, and D. M. Knowles. 1995. Kaposi's sarcoma-associated herpesvirus-like DNA sequences in AIDS-related body-cavity-based lymphomas. N. Eng. J. Med. 332:1186–1191.
17. Cesarman, E., P. S. Moore, P. H. Rao, G. Inghirarni, D. M. Knowles, and Y. Chang. 1995b. In vitro establishment and characterization of two AIDS-related lymphoma cell lines containing Kaposi's sarcoma-associated herpesvirus-like (KSHV) DNA sequences. Blood. 86:2708–2714.
18. Chadburn, A, E. Cesarman, J. Jagirdar, M. Subar, R. N. Mir, and D. M. Knowles. 1993. CD30 (Ki-1) positive anaplastic large cell lymphomas in individuals infected with the human immunodeficiency virus. Cancer. 72:3078–3090.
19. Chang, Y., E. Cesarman, M. S. Pessin, F. Lee, J. Culpepper, D. M. Knowles, and P. S. Moore. 1994. Identification of herpesvirus-like DNA sequences in AIDS-associated Kaposi's sarcoma. Science. 266:1865–1869.
20. Chang, Y., P. S. Moore, S. J. Talbot, C. H. Boshoff, T. Zarkowska, D. Godden-Kent, H. Paterson, R. A. Weiss, and S. Mittnacht. 1996. Cyclin encoded by KS herpesvirus. Nature. 382:410.
21. Cheng, E. H.-Y., J. Nicholas, D.S. Bellows, G. S. Hayward, H.-G. Guo, M. S. Reitz, and J. M. Hardwick. 1996. Kaposi's sarcoma-associated virus, HHV8, encodes a Bcl-2 homolog that inhibits apoptosis. Proc. Natl. Acad. Sci. USA. 94:690–694.
22. Colacino, J. M., C. C. Flowers, J. Menna, D. J. O'Callaghan, and J. Staczek. 1989. Physical structure and molecular cloning of equine cytomegalovirus DNA. Virology. 173:566–580.
23. Davison, A. J. 1993. Herpesvirus genes. Rev. Med. Virol. 3:237–244.
24. Davison, A. J., and J. E. Scott. 1986. The complete DNA sequence of varicella-zoster virus. J. Gen. Virol. 67:1759–1816.
25. Efstathiou, S., Y. M. Ho, and A. C. Minson. 1990. Cloning and molecular characterization of the murine herpesvirus 68 genome. J. Gen. Virol. 71:1355–1364.
26. Ensoli, B., G. Barillari, L. Buonagura, and R. C. Gallo. 1991. Molecular mechanisms in the pathogenesis of AIDS-associated Kaposi's sarcoma. Adv. Exp. Med. Biol. 303:27–38.
27. Everett, R, P. O'Hare, D. O'Rourke, P. Barlow, and A. Orr. 1995. Point mutations in the herpes simplex virus type 1 Vmw110 RING finger helix affect activation of gene expression, viral growth, and interaction with PML-containing nuclear structures. J. Virol. 69:7339–7344.
28. Everett, R. D., P. Barlow, A. Milner, B. Luisi, A. Orr, G. Hope, and D. Lyon. 1993. A novel arrangement of zinc-binding residues and secondary structure in the C3HC4 motif of an alpha herpes virus protein family. J. Mol. Biol. 234:1038–1047.
29. Frank, D., E. Cesarnan, Y. F. Liu, R. E. Michier, and D. M. Knowles. 1995. Posttransplantation lymphoproliferative disorders frequently contain type A and not type B Epstein-Barr virus. Blood. 85:1396–1403.

30. Gao, S.-J., L. Kingsley, M. Li, W. Zheng, C. Parravicini, J. Ziegler, R. Newton, C. R. Rinaldo, A. Saah, J. Phair, R. Detels, Y. Chang, and P. S. Moore. 1996. KSHV antibodies among Americans, Italians and Ugandans with and without Kaposi's sarcoma. Nature Med. 2:925–928.

31. Gompels, U. A., M. A. Craxton, and R. W. Honess. 1988. Conservation of gene organization in the lymphotropic herpesviruses saimiri and Epstein-Barr virus. J. Virol. 62:757–767.

32. Gompels, U. A, J. Nicholas, G. Lawrence, M. Jones, B. J. Thomson, M. E. D. Main, S. Efstathiou, M. Craxton, and H. A. Macaulay. 1995. The DNA sequence of human herpesvirus-6: structure, coding content, and genome evolution. Virology. 209:29–51.

33. Guo, H.-G., P. Browning, J. Nicholas, G. S. Hayward, Y. W. Jiang, M. Sadowska, E. Tschachler, M. Raffeld, S. Columbini, R. C. Gallo, and M. Reitz. 1996. Characterization of a chemokine receptor-related gene in human herpesvirus 8 and its expression in Kaposi's sarcoma. Virology. In press.

34. Hayward, G. S. 1993. Immediate-early gene regulation in herpes simplex virus, p. 15–23. In M. Peterlin (ed.), Seminars in Virology, vol. 4. Saunders/Academic Press.

35. Heller, M, and E. Kieff 1981. Colinearity between the DNAs of Epstein-Barr virus and herpesvirus papio. J. Virol. 37:821–826.

36. Honess, R. W., W. Bodenmer, K. R. Cameron, H.-H. Niller, B. Fleckenstein, and R. E. Randall. 1986. The A+T-rich genome of herpesvirus saimiri contains a highly conserved gene for thymidylate synthase. Proc. Natl. Acad. Sci. USA. 83:3604–3608.

37. Kedes, D. H., E. Oberskalski, M. Busch, R. Kohin, J. Flood, and D. Ganem. 1996. The seroepidemiology of human herpesvirus 8 (Kaposi's sarcoma-associated herpesvirus): Distribution of infection in KS risk groups and evidence for sexual transmission. Nature Med. 2:918–924.

38. Levy, J. A. 1995. A new human herpesvirus: KSHV or HHV8? The Lancet. 34:786.

39. Lomonte, P., M. Bublot, V. van Santen, G. M. Keil, P.-P. Pastoret, and E. Thiry. 1995. Analysis of bovine herpesvirus 4 genomic regions located outside the conserved gammaherpesvirus gene blocks. J. Gen. Virol. 76:1835–1843.

40. Massung, R. F., V. Jayarama, and R. W. Moyer. 1993. DNA sequence analysis of conserved and unique regions of swinepox virus: identification of genetic elements supporting phenotypic observations including a novel G protein-coupled receptor homologue. Virology. 197:511–528.

41. McGeoch, D. J., and S. Cook. 1994. Molecular phylogeny of the Alphaherpesvirinae subfamily and a proposed evolutionary timescale. J. Mol. Biol. 238:9–22.

42. McGeoch, D. J., S. Cook, A Dolan, F. E. Jamieson, and E. A. R. Telford. 1995. Molecular phylogeny and evolutionary timescale for the family of mammalian herpesviruses. J. Mol. Biol. 247:443–458.

43. Miller, G., D. Coope, J. Niederman, and J. S. Pagano. 1975. Biological properties of Burkitt lymphoma and mononucleosis derived strains of Epstein-Barr virus released from transformed marmoset cells. J. Virol. 18:1071–1080.

44. Miller, G., M. O. Rigsby, L. Heston, E. Grocan, R. Sun, C. Metroka, J. A. Levy, S.-J. Gao, Y. Chang, and P. Moore. 1996. Antibodies to butyrate-inducible antigens of Kaposi's sarcoma-associated herpesvirus in patients with HIV-1 infection. New Eng. J. Med. 334:1292–1297.

45. Moore, P. S., and Y. Chang. 1995. Detection of herpesvirus-like DNA sequences in Kaposi's sarcoma in patients with and those without HIV infection. N. Eng. J. Med. 332:1182–1185.

46. Moore, P. S., S.-J. Gao, G. Dominguez, E. Cesarman, O. Lungu, D. Knowles, R. Garber, P. E. Pellett, D. J. McGeoch, and Y. Chang. 1996. Primary characterization of a herpesvirus agent associated with Kaposi's sarcoma. J. Virol. 70:549–558.

47. Nicholas, J. 1994. Nucleotide sequence analysis of a 21-kbp region of the genome of human herpesvirus-6 containing homologues of human cytomegalovirus major immediate-early and replication genes. Virology. 204:738–750.

48. Nicholas, J., K. R. Cameron, H. Coleman, C. Newman, and R. W. Honess. 1992. Analysis of nucleotide sequence of the rightmost 43 kbp of herpesvirus saimiri (HVS) L-DNA: general conservation of genetic organization between HVS and Epstein-Barr virus. Virology. 188:296–310.

49. Nicholas, J., and M. E. D. Martin. 1994. Nucleotide sequence analysis of a 38.5-kilobase-pair region of the genome of human herpesvirus 6 encoding human cytomegalovirus immediate-early gene homologs and transactivating functions. J. Virol. 68:597–610.

50. Nicholas, J., V. R. Ruvolo, W. H. Burns, G. Sandford, X. Wan, D. Ciufo, S. Hendrickson, H.-G. Guo, G. S. Hayward, and M. S. Reitz. 1997. Kaposi's sarcoma-associated human herpesvirus-8 homologues of macrophage inflammatory protein-1 and interleukin-6. Nature Med. 3:287–292.

51. Perry, L. J., F. J. Rixon, R. D. Everett, M. C. Frame, and D. J. McGeoch. 1986. Characterization of the IE110 gene of herpes simplex virus type 1. J. gen. Virol. .67:2365–2380.

52. Renne, R., W. Zhong, B. Herndier, M. McGrath, N. Abbey, D. Kedes, and D. Ganem. 1996. Lytic growth of Kaposi's sarcoma-associated herpesvirus (human herpesvirus 8) in culture. Nature Med. 2:342–346.

53. Richter, J., I. Puchtler, and B. Fleckenstein. 1988. Thymidylate synthase gene of herpesvirus ateles. J. Virol. 62:3530–3535.

54. Rode, H.-J., W. Janssen, A Rosen-Wolff, J. J. Bugert, P. Thein, Y. Becker, and G. Darai. 1993. The genome of equine herpesvirus type 2 harbors an interleukin 10 (IL10)-like gene. Virus Genes. 7:111–116.

55. Saha, V., T. Chaplin, A. Gregorini, P. Ayton, and B. D. Young. 1995. The leukemia-associated-protein (LAP) domain, a cystein-rich motif, is present in awide range of proteins, including MLL, AF10, and MLLT6 proteins. Proc. Natl. Acad. Sci. USA. 92:9737–9741.

56. Schirm, S., I. Muller, R. C. Desrosiers, and B. Fleckenstein. 1984. Herpesvirus saimiri DNA in a lymphoid cell line established by in vitro transformation. J. Virol. 49:938–946.

57. Soulier, J., L. Grollet, E. Oksenhendler, P. Cacoub, D. Cazals-Hatem, P. Babinet, M. F. d'Agay, J. P. Clauvel, M. Raphael, L. Degos, and et al. 1995. Kaposi's sarcoma-associated herpesvirus-like DNA sequences in multicentric Castleman's disease. Blood. 86:1276–1280.

58. Stamminger, T., R. W. Honess, D. F. Young, W. Bodemer, E. D. Blair, and B. Fleckenstein. 1987. Organization of terminal reiterations in the virion DNA of herpesvirus saimiri. J. Gen. Virol. 68:1049–1066.

59. Takeishi, K., S. Kaneda, D. Ayusawa, K. Shimizu, O. Gotoh, and T. Seno. 1985. Nucleotide sequence of a functional cDNA for human thymidylate synthase. Nuc. Acids Res. 13:2035–2043.

60. Telford, E., M. J. Studdert, C. T. Agius, M. S. Watson, H. C. Aird, and A. J. Davison. 1993. Equine herpesvirus 2 and 5 are gammaherpesviruses. Virology. 195:492–499.
61. Telford, E. A. R., M. S. Watson, H. C. Aird, J. Perry, and A. J. Davison. 1995. The DNA sequence of equine herpesvirus 2. J. Mol. Biol. 249:520–528.
62. Trimble, J. J., S. C. S. Murthy, A. Bakker, R. Grassmann, and R. C. Desrosiers. 1988. A gene for dihydrofolate reductase in a herpesvirus. Science. 239:1145–1147.
63. Uchida, H., S. Kawano, N. Sato, and T. Kuroiwa. 1993. Isolation and characterization of novel genes which are expressed during the very early stage of zygote formation in chlamydomonas reinhardtii. Curr. Genet. 24:296–300.
64. van Santen, V. L. 1991. Characterization of the Bovine herpesvirus 4 major immediate-early transcript. J. Virol. 65:5211–5224.
65. Vieria, P., R. D. Waal-Maleft, M.-N. Dong, K. E. Johnson, R. Kastelein, D. F. Fiorentino, J. E. D. Vries, M.-G. Roncarolo, T. R. Mosmann, and K. W. Moore. 1991. Isolation and expression of human cytokine synthesis inhibitory factor cDNA clones: homology to Epstein-Barr virus open reading frame BCRF1. Proc. Natl. Acad. Sci. USA. 88:1172–1176.
66. Wang, C. Y., A. L. Schroeter, and W. P. Su. 1995. Acquired immunodeficiency syndrome-related Kaposi's sarcoma. Mayo Clinic Proc. 70:869–879.
67. Wharton, J. H., B. E. Henry, and D. J. O'Callaghan. 1981. Equine cytomegalovirus: cultural characteristics and properties of viral DNA. Virology. 109:106–119.
68. Yao, Z., S. L. Painter, W. C. Fanslow, D. Ulrich, B. M. Macduff, M. K. Springgs, and R. J. Armitage. 1995. Human IL-17: a novel cytokine derived from T cells. J. Immunol. 155:5483–5486.
69. Zhong, W., H. Wang, B. Hemdier, and D. Ganem. 1996. Restricted expression of Kaposi sarcoma-associated herpesvirus (human herpesvirus 8) genes in Kaposi sarcoma. Proc. Natl. Acad. Sci. USA. 93:6641–6646.
70. Zong, J.-C., C. Metroka, M. S. Reitz, J. Nicholas, and G. S. Hayward. 1996. Strain variability amongst Kaposi sarcoma associated herpesvirus (HHV-8) genomes: Evidence that a large cohort of U.S.A. AIDS patients may have been infected by a single common isolate. J. Virol.71:2505–2511.

What is claimed is:

1. A polynucleotide encoding one or more of HHV-8 virally encoded proteins selected from the group consisting of: TS, DHFR, Bcl-2, IL-6, MIP-1A, MIP-1B, BCK, IE-1A, and IE-1B , as shown in SEQ ID NO: 22, 23, 24, 25, 26, 27, 28, 29, and 30, respectively, wherein the polynucleotide does not contain HHV-8 genes which are not in the divergent locus DL-B.

2. The polynucleotide of claim 1, which encodes TS (SEQ ID NO:22).

3. The polynucleotide of claim 1, which encodes DHFR (SEQ ID NO:23).

4. The polynucleotide of claim 1, Which encodes Bcl-2 (SEQ ID NO:24).

5. The polynucleotide of claim 1, which encodes MIP-1A (SEQ ID NO:26).

6. The polynucleotide of claim 1, which encodes MIP-1B (SEQ ID NO:27).

7. The polynucleotide of claim 1, which encodes BCK (SEQ ID NO:28).

8. The polynucleotide of claim 1, which encodes IE-1A (SEQ ID NO:29).

9. The polynucleotide of claim 1, which encodes IE-1B (SEQ ID NO:30).

10. The polynucleotide of claim 1, which encodes IL-6 (SEQ ID NO25).

* * * * *

UNITED STATES PATENT AND TRADEMARK OFFICE
CERTIFICATE OF CORRECTION

PATENT NO.    : 6,264,958 B1
DATED         : July 24, 2001
INVENTOR(S)   : Gary S. Hayward et al.

It is certified that error appears in the above-identified patent and that said Letters Patent is hereby corrected as shown below:

<u>Title page,</u>
Item [57], ABSTRACT,
Delete "Cademan's disease" insert -- Castleman's disease --
Delete "immediatelady" insert -- immediate-early --

Signed and Sealed this

Twenty-second Day of October, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,264,958 B1 Page 1 of 1
APPLICATION NO. : 09/230637
DATED : July 24, 2001
INVENTOR(S) : Gary S. Hayward et al.

It is certified that error appears in the above-identified patent and that said Letters Patent is hereby corrected as shown below:

On the Title Page, Assignee section (73):
    Please add the following Assignee:
--The Government of the United States of America, as represented by the Secretary, Department of Health and Human Services, Washington, DC (US)--

Signed and Sealed this

Twenty-third Day of October, 2007

JON W. DUDAS
*Director of the United States Patent and Trademark Office*

```
                         SEQUENCE LISTING

<160> NUMBER OF SEQ ID NOS: 62

<210> SEQ ID NO: 1
<211> LENGTH: 1014
<212> TYPE: DNA
<213> ORGANISM: Kaposi's sarcoma-associated herpesvirus

<400> SEQUENCE: 1
atgtttccgt ttgtaccttt aagcttgtat gtcgccaaaa agttattccg tgccaggggg      60
tttcgcttct gtcaaaagcc tggcgtcttg gctttggccc ccgaggttga cccttgttcg     120
attcagcatg aggtaactgg ggctgagacg ccccacgagg aacttcagta tctcaggcag     180
ttgagggaaa ttttgtgccg tggcagcgat cgactcgacc gcaccggcat aggcaccctc     240
tctctatttg gcatgcaggc caggtatagt ctgcgggacc actttccctt actaaccaca     300
aagcgggtgt tttggcgagg cgtagtgcaa gagctgcttt ggtttctgaa ggggagtact     360
gactccaggg agctttcaag aacaggagtc aagatatggg acaaaaatgg ctccagggag     420
ttcctggccg ggcgcggcct ggcgcacaga agggaggggg atttgggacc tgtttacggt     480
ttccagtgga ggcactttgg ggcggcgtac gtggacgcgg atgctgacta tacaggccag     540
gggtttgacc aattgtcgta cattgtggat ttaataaaaa ataatccgca cgatagaaga     600
atcattatgt gtgcgtggaa cccggcggac ttgtcgttga tggcgcttcc gccctgtcac     660
ttgttatgtc aattttatgt agctgacggt gagctttcct gtcagctgta tcagaggtcg     720
ggagacatgg gtttgggagt tccttttaac attgccagct attccctctt aacttatatg     780
cttgctcatg ttactggtct tagacccggg gagtttattc acacgttggg agatgcccac     840
atctacaaaa cgcatataga gccactacgg ctgcagctga cgcgcactcc acgtcccttt     900
ccgcgcctgg agatactccg gtctgtttct tccatggaag agtttacacc tgatgatttt     960
agactggtgg actactgccc gcatcctacc attcgtatgg aaatggcagt atag         1014

<210> SEQ ID NO: 2
<211> LENGTH: 633
<212> TYPE: DNA
<213> ORGANISM: Homo sapiens
```

```
<400> SEQUENCE: 2
atggatccta cactttactg tgtagttgcg gttgatacca aactcgggat cggaaaaaac    60
agatgtctcc cgtggcctgc attgcgggga gacatgaggc gttttcgaca gctgactacc   120
gactgtgccc ctggaaaaca aaacatggtt gttatgggc ggcgcacatg ctttcgatt    180 cccgcgggct gtcgaccatt ggcgggtaga atcaatgtgg ttctaagtcg cacgttagaa   240
accccgcccc ctggtgctca cttttggcg agttcgctcg atgccgcgct tgggttggcg    300
agaagcccag agctagcaca gcaaattgac aaggtttggg tcatcggggg tggggacttg   360
taccgggagg cgctcactgg cccctggcca gttaggctat ttttaacccg ggttttacat   420
gactttgcgt gtgacgtgtt tctctcgcat gatagcttgg ctgcgtatgc ccgcgtgaac   480
cccaagcctg gtgagcaaga gagggttttt caagaacgtg gtatcttta catgtttgag    540 acctacataa aagtgactca gagttcggat acgcgttgc ctgatttgga gcggccccga    600
cccgcgaccc cgcccttcag tgagacttcg taa                                633

<210> SEQ ID NO: 3
<211> LENGTH: 528
<212> TYPE: DNA
<213> ORGANISM: Kaposi's sarcoma-associated herpes-like virus

<400> SEQUENCE: 3
atggacgagg acgttttgcc tggagaggtg ttggccattg aagggatatt catggcctgt    60
ggattaaacg aacctgagta cctgtaccat cctttgctca gccctattaa gctatacatc   120
acaggcttaa tgcgagacaa ggagtcttta ttcgaggcca tgttggctaa tgtgagattt   180
cacagcacca ccgtatataaa ccagcttggg ttgagcatgc tgcaggttag cggcgatgga   240
aacatgaact gggggcgagc cctggctata ctgacctttg cagttttgt ggcccagaag    300 ttatccaacg aacctcacct gcgagacttt gctttggccg ttttacctgt atatgcgtat   360
gaagcaatcg accccagtg gtttcgcgct cgcggaggct ggcgaggcct aaggcgtat    420 tgtacacagg tgcttaccag aagaagggga cggagaatga cagcgctatt gggaagcatt   480
gcattattgg ccactatatt ggcagcggtc gcgatgagca ggagataa                 528

<210> SEQ ID NO: 4
<211> LENGTH: 615
<212> TYPE: DNA
<213> ORGANISM: Kaposi's sarcoma-associated herpes-like virus

<400> SEQUENCE: 4
atgtgctggt tcaagttgtg gtctctcttg ctggtcggtt cactgctggt atctggaacg    60
cggggcaagt tgccggacgc ccccgagttt gaaaaggatc ttctcattca gagactcaat   120
tggatgctat gggtgatcga tgaatgcttc cgcgacctct gttaccgtac cggcatctgc   180
aagggtattc tagagcccgc tgctattttt catctgaaac taccagccat caacgatact   240
gatcactgcg ggtaatagg atttaatgag actagctgcc ttaaaaagct cgccgatggc   300
ttttttgaat tcgaggtgtt gtttaagttt ttaacgacgg agtttggaaa atcagtgata   360
aacgtggacg tcatggagct tctgacgaag accttaggat gggacataca ggaagagctc   420
aataagctga ctaagacgca ctacagtcca cccaaatttg accgcggtct attagggagg   480
cttcagggac ttaagtattg ggtgagacac tttgcttcgt tttatgttct gagtgcaatg   540
gaaaagtttg caggtcaagc ggtgcgtgtt ttggactcta tcccagacgt gactcctgac   600
gtccacgata agtaa                                                    615
```

<210> SEQ ID NO: 5
<211> LENGTH: 288
<212> TYPE: DNA
<213> ORGANISM: Kaposi's sarcoma-associated herpes-like virus

<400> SEQUENCE: 5

```
atggccccg tccacgtttt atgctgcgtt agcgtactgc ttgccacgtt ttacctgacg      60
cccacagaaa gcgcgggggtc actcgtgtcg tacacgccta atagctgctg ctacgggttc   120
cagcagcacc caccgcccgt ccaaattcta aaagagtggt atcccacgtc cccagcgtgc   180
ccaaaacccg gagttatttt gctgaccaag cgagggcgtc agatctgcgc agacccttcc   240
aaaaactggg ttaggcagct gatgcagcgg ctgcctgcca tagcttag                288
```

<210> SEQ ID NO: 6
<211> LENGTH: 285
<212> TYPE: DNA
<213> ORGANISM: Kaposi's sarcoma-associated herpes-like virus

<400> SEQUENCE: 6

```
atggacacca aggcatcct gctcgtcgct gtgctgactg ccttgctttg tttgcaatct      60
ggggacacgc tgggagcgtc ctggcataga ccggacaagt gctgtctcgg ttaccagaaa   120
agaccattac acaggtgct tctgtccagc tggtaccca cctcccaact gtgcagcaag     180
ccgggtgtga tattttgac aaagcgtggt cgccaggtgt gtgccgacaa atcgaaagac    240
tgggtgaaga agctgatgca gcaattacca gtcactgctc gctga                   285
```

<210> SEQ ID NO: 7
<211> LENGTH: 345
<212> TYPE: DNA
<213> ORGANISM: Kaposi's sarcoma-associated herpes-like virus

<400> SEQUENCE: 7

```
atgtggagca tgtgctgggt gttgcgcgca catttggggc tgctcttctg ggtggccgtg     60
attgagctat gtgcggccag cggtcctgcc accatcatgg cctcggattg ttgcgagaat   120
tccctgtcca gtgccagatt gccaccggat aagctgatat gcggtggta ctggacgtcc    180
accgtgtatt gtcgccagaa ggcagtcatt tttgtaacgc actcggggcg gaaagtatgc   240
gggtcgcctg cgaagcggcg cacgcgtctt ctgatggaga agcacacgga gatacctctc   300
gcgaagcgcg tagcgcttcg cgccggtaaa gggttatgcc cctag                   345
```

<210> SEQ ID NO: 8
<211> LENGTH: 771
<212> TYPE: DNA
<213> ORGANISM: Kaposi's sarcoma-associated herpes-like virus

<400> SEQUENCE: 8

```
atggcgtcca aggacgtaga agagggtgta gagggaccca tctgctggat atgtagggaa     60
gaggtgggga acgagggcat acacccctgc gcctgtaccg gagagctgga tgtcgtccac   120
ccgcagtgtt taagcacttg gctaacagtg tctcgaaaca cggcctgtca aatgtgtcgc   180
gttatatacc gcacgcgcac gcagtggcgt agtcgcctta acctgtggcc ggagatggag   240
cgccaagaaa ttttttgaact gtttctgctg atgtctgtgg tggtggctgg gcttgtcggc   300
gtggcgttgt gcacctggac gctcctggtc atcctaactg ctcctgcggg aacattctcc   360
cccgggggccg tgctcggttt tctctgcttc tttgggtttt accaaatatt tattgtgttt   420
gcatttggcg gcatatgccg cgtaagtggc actgtgaggg cattatacgc ggcaaataac   480
```

-continued

```
acccgggtga ccgtactgcc ataccgacgg ccgcgccggc caaccgcgaa cgaagataac     540
atcgaattga cggtccttgt cggacccgcg ggcgggacgg acgaggagcc cacggacgag     600
tcatctgaag gagacgtcgc ctctggagac aaagaacgtg acggttcatc cggagacgag     660
ccggacgggg gcccgaacga ccgtgcggga cttagggga cagcgcgtac cgacctatgc      720
gcgcccacaa aaaagccggt gcggaaaaat catccaaaaa acaacggttg a              771
```

<210> SEQ ID NO: 9
<211> LENGTH: 1002
<212> TYPE: DNA
<213> ORGANISM: Kaposi's sarcoma-associated herpes-like virus

<400> SEQUENCE: 9

```
atggaagatg aggatgttcc tgtctgctgg atttgcaacg aggagctcgg aaatgagaga     60
tttagagcct gtggatgcac aggagagctc gagaacgtcc atagaagttg tttaagcacc    120
tggctcacta tctctagaaa cacggcctgt cagatatgtg gcgtcgtata caacacgcgc    180
gtggtctggc gacccttgcg cgaaatgacg ctattgcctc ggctgactta ccaggagggt    240
ctggaactga ttgtttttat tttcattatg acattggggg ccgctggcct tgccgctgcg    300
acgtgggttt ggctatatat agtgggcggt catgacccag atagatca cgtcgctgca     360 gccgcgtact acgtttttttt cgtgttttac caattgtttg tcgttttttgg gttgggtgcg    420 tttttccaca tgatgcgcca cgtggggcgg gcatacgctg ctgtaaacac gcgggttgaa    480
gtgtttccat atagacctcg gccgacatca ccagagtgtg cagtagagga gatcgagctt    540
caggaaattc ttccccgtgg ggataaccag gacgaggagg ggcccgcggg ggcagctcca    600
ggcgaccaaa atggccccgc gggggcagct ccaggcgacc aagatggccc cgcggatggc    660
gctcctgtgc atcgcgactc agaagaatcc gtggatgaag ctgcagggta caaggaagcg    720
ggagaaccaa cacataatga tggacgtgat gacaatgtag agccaaccgc ggttgggtgt    780
gactgtaaca acttgggcgc tgagcggtat agggccactt actgtggcgg ttatgttggt    840
gcccagtcgg gcgatgggc ttatagtgtc tcctgccata ataaggctgg accctcctct    900
ctagttgata tccttccaca gggtttgcct gggggtggct atggttccat gggcgtgatt    960
aggaaacgtt cggctgtttc gtctgcccctt atgtttcatt aa                       1002
```

<210> SEQ ID NO: 10
<211> LENGTH: 24
<212> TYPE: DNA
<213> ORGANISM: Kaposi's sarcoma-associated herpes-like virus

<400> SEQUENCE: 10

```
ggrccygtst ayggrttyca gtgg                                             24
```

<210> SEQ ID NO: 11
<211> LENGTH: 23
<212> TYPE: DNA
<213> ORGANISM: Kaposi's sarcoma-associated herpes-like virus

<400> SEQUENCE: 11

```
ctggcbatgt tgaarggrac bcc                                              23
```

<210> SEQ ID NO: 12
<211> LENGTH: 18
<212> TYPE: DNA
<213> ORGANISM: Kaposi's sarcoma-associated herpes-like virus

```
<400> SEQUENCE: 12
gggttccagt ggaggcac                                              18

<210> SEQ ID NO: 13
<211> LENGTH: 21
<212> TYPE: DNA
<213> ORGANISM: Kaposi's sarcoma-associated herpes-like virus

<400> SEQUENCE: 13
acgtggatcc ctctgacaac c                                          21

<210> SEQ ID NO: 14
<211> LENGTH: 21
<212> TYPE: DNA
<213> ORGANISM: Kaposi's sarcoma-associated herpes-like virus

<400> SEQUENCE: 14
ggatggatcc ctctgacaac c                                          21

<210> SEQ ID NO: 15
<211> LENGTH: 22
<212> TYPE: DNA
<213> ORGANISM: Kaposi's sarcoma-associated herpes-like virus

<400> SEQUENCE: 15
acgtggatcc gtgttgtcta cg                                         22

<210> SEQ ID NO: 16
<211> LENGTH: 23
<212> TYPE: DNA
<213> ORGANISM: Kaposi's sarcoma-associated herpes-like virus

<400> SEQUENCE: 16
ctagagatct gtttagtccg gag                                        23

<210> SEQ ID NO: 17
<211> LENGTH: 21
<212> TYPE: DNA
<213> ORGANISM: Kaposi's sarcoma-associated herpes-like virus

<400> SEQUENCE: 17
gtacggatcc acggagcata c                                          21

<210> SEQ ID NO: 18
<211> LENGTH: 18
<212> TYPE: DNA
<213> ORGANISM: Kaposi's sarcoma-associated herpes-like virus

<400> SEQUENCE: 18
cagttacatg tagccatg                                              18

<210> SEQ ID NO: 19
<211> LENGTH: 19
<212> TYPE: DNA
<213> ORGANISM: Kaposi's sarcoma-associated herpes-like virus

<400> SEQUENCE: 19
ctgcatcagt acactattc                                             19

<210> SEQ ID NO: 20
<211> LENGTH: 16
<212> TYPE: DNA
<213> ORGANISM: Kaposi's sarcoma-associated herpes-like virus
```

```
<400> SEQUENCE: 20
tgtaggggaa gccgat                                                    16

<210> SEQ ID NO: 21
<211> LENGTH: 21
<212> TYPE: DNA
<213> ORGANISM: Kaposi's sarcoma-associated herpes-like virus

<400> SEQUENCE: 21
caatggtgta agacgagatt g                                              21

<210> SEQ ID NO: 22
<211> LENGTH: 337
<212> TYPE: PRT
<213> ORGANISM: Kaposi's sarcoma-associated herpes-like virus

<400> SEQUENCE: 22
```

Met Phe Pro Phe Val Pro Leu Ser Leu Tyr Val Ala Lys Lys Leu Phe
 1               5                  10                  15

Arg Ala Arg Gly Phe Arg Phe Cys Gln Lys Pro Gly Val Leu Ala Leu
            20                  25                  30

Ala Pro Glu Val Asp Pro Cys Ser Ile Gln His Glu Val Thr Gly Ala
        35                  40                  45

Glu Thr Pro His Glu Glu Leu Gln Tyr Leu Arg Gln Leu Arg Glu Ile
    50                  55                  60

Leu Cys Arg Gly Ser Asp Arg Leu Asp Arg Thr Gly Ile Gly Thr Leu
65                  70                  75                  80

Ser Leu Phe Gly Met Gln Ala Arg Tyr Ser Leu Arg Asp His Phe Pro
                85                  90                  95

Leu Leu Thr Thr Lys Arg Val Phe Trp Arg Gly Val Val Gln Glu Leu
            100                 105                 110

Leu Trp Phe Leu Lys Gly Ser Thr Asp Ser Arg Glu Leu Ser Arg Thr
        115                 120                 125

Gly Val Lys Ile Trp Asp Lys Asn Gly Ser Arg Glu Phe Leu Ala Gly
    130                 135                 140

Arg Gly Leu Ala His Arg Arg Glu Gly Asp Leu Gly Pro Val Tyr Gly
145                 150                 155                 160

Phe Gln Trp Arg His Phe Gly Ala Ala Tyr Val Asp Ala Asp Ala Asp
                165                 170                 175

Tyr Thr Gly Gln Gly Phe Asp Gln Leu Ser Tyr Ile Val Asp Leu Ile
            180                 185                 190

Lys Asn Asn Pro His Asp Arg Arg Ile Ile Met Cys Ala Trp Asn Pro
        195                 200                 205

Ala Asp Leu Ser Leu Met Ala Leu Pro Pro Cys His Leu Leu Cys Gln
    210                 215                 220

Phe Tyr Val Ala Asp Gly Glu Leu Ser Cys Gln Leu Tyr Gln Arg Ser
225                 230                 235                 240

Gly Asp Met Gly Leu Gly Val Pro Phe Asn Ile Ala Ser Tyr Ser Leu
                245                 250                 255

Leu Thr Tyr Met Leu Ala His Val Thr Gly Leu Arg Pro Gly Glu Phe
            260                 265                 270

Ile His Thr Leu Gly Asp Ala His Ile Tyr Lys Thr His Ile Glu Pro
        275                 280                 285

Leu Arg Leu Gln Leu Thr Arg Thr Pro Arg Pro Phe Pro Arg Leu Glu
    290                 295                 300

```
Ile Leu Arg Ser Val Ser Ser Met Glu Glu Phe Thr Pro Asp Phe
305                 310                 315                 320

Arg Leu Val Asp Tyr Cys Pro His Pro Thr Ile Arg Met Glu Met Ala
                325                 330                 335

Val
```

<210> SEQ ID NO: 23
<211> LENGTH: 210
<212> TYPE: PRT
<213> ORGANISM: Kaposi's sarcoma-associated herpes-like virus

<400> SEQUENCE: 23

```
Met Asp Pro Thr Leu Tyr Cys Val Val Ala Val Asp Thr Lys Leu Gly
1               5                   10                  15

Ile Gly Lys Asn Arg Cys Leu Pro Trp Pro Ala Leu Arg Gly Asp Met
                20                  25                  30

Arg Arg Phe Arg Gln Leu Thr Thr Asp Cys Ala Pro Gly Lys Gln Asn
            35                  40                  45

Met Val Val Met Gly Arg Arg Thr Trp Leu Ser Ile Pro Ala Gly Cys
50                  55                  60

Arg Pro Leu Ala Gly Arg Ile Asn Val Val Leu Ser Arg Thr Leu Glu
65                  70                  75                  80

Thr Pro Pro Pro Gly Ala His Phe Leu Ala Ser Ser Leu Asp Ala Ala
                85                  90                  95

Leu Gly Leu Ala Arg Ser Pro Glu Leu Ala Gln Gln Ile Asp Lys Val
            100                 105                 110

Trp Val Ile Gly Gly Gly Asp Leu Tyr Arg Glu Ala Leu Thr Gly Pro
        115                 120                 125

Trp Pro Val Arg Leu Phe Leu Thr Arg Val Leu His Asp Phe Ala Cys
130                 135                 140

Asp Val Phe Leu Ser His Asp Ser Leu Ala Ala Tyr Ala Arg Val Asn
145                 150                 155                 160

Pro Lys Pro Gly Glu Gln Glu Arg Val Phe Gln Glu Arg Gly Ile Phe
                165                 170                 175

Tyr Met Phe Glu Thr Tyr Ile Lys Val Thr Gln Ser Ser Asp Thr Ala
            180                 185                 190

Leu Pro Asp Leu Glu Arg Pro Arg Pro Ala Thr Pro Pro Phe Ser Glu
        195                 200                 205

Thr Ser
    210
```

<210> SEQ ID NO: 24
<211> LENGTH: 175
<212> TYPE: PRT
<213> ORGANISM: Kaposi's sarcoma-associated herpes-like virus

<400> SEQUENCE: 24

```
Met Asp Glu Asp Val Leu Pro Gly Glu Val Leu Ala Ile Glu Gly Ile
1               5                   10                  15

Phe Met Ala Cys Gly Leu Asn Glu Pro Glu Tyr Leu Tyr His Pro Leu
                20                  25                  30

Leu Ser Pro Ile Lys Leu Tyr Ile Thr Gly Leu Met Arg Asp Lys Glu
            35                  40                  45

Ser Leu Phe Glu Ala Met Leu Ala Asn Val Arg Phe His Ser Thr Thr
50                  55                  60
```

```
Gly Ile Asn Gln Leu Gly Leu Ser Met Leu Gln Val Ser Gly Asp Gly
 65                  70                  75                  80

Asn Met Asn Trp Gly Arg Ala Leu Ala Ile Leu Thr Phe Gly Ser Phe
                 85                  90                  95

Val Ala Gln Lys Leu Ser Asn Glu Pro His Leu Arg Asp Phe Ala Leu
            100                 105                 110

Ala Val Leu Pro Val Tyr Ala Tyr Glu Ala Ile Gly Pro Gln Trp Phe
            115                 120                 125

Arg Ala Arg Gly Gly Trp Arg Gly Leu Lys Ala Tyr Cys Thr Gln Val
            130                 135                 140

Leu Thr Arg Arg Gly Arg Arg Met Thr Ala Leu Leu Gly Ser Ile
145                 150                 155                 160

Ala Leu Leu Ala Thr Ile Leu Ala Ala Val Ala Met Ser Arg Arg
                165                 170                 175
```

<210> SEQ ID NO: 25
<211> LENGTH: 204
<212> TYPE: PRT
<213> ORGANISM: Kaposi's sarcoma-associated herpes-like virus

<400> SEQUENCE: 25

```
Met Cys Trp Phe Lys Leu Trp Ser Leu Leu Val Gly Ser Leu Leu
 1               5                  10                  15

Val Ser Gly Thr Arg Gly Lys Leu Pro Asp Ala Pro Glu Phe Glu Lys
                20                  25                  30

Asp Leu Leu Ile Gln Arg Leu Asn Trp Met Leu Trp Val Ile Asp Glu
             35                  40                  45

Cys Phe Arg Asp Leu Cys Tyr Arg Thr Gly Ile Cys Lys Gly Ile Leu
 50                  55                  60

Glu Pro Ala Ala Ile Phe His Leu Lys Leu Pro Ala Ile Asn Asp Thr
 65                  70                  75                  80

Asp His Cys Gly Leu Ile Gly Phe Asn Glu Thr Ser Cys Leu Lys Lys
                 85                  90                  95

Leu Ala Asp Gly Phe Phe Glu Phe Glu Val Leu Phe Lys Phe Leu Thr
            100                 105                 110

Thr Glu Phe Gly Lys Ser Val Ile Asn Val Asp Val Met Glu Leu Leu
            115                 120                 125

Thr Lys Thr Leu Gly Trp Asp Ile Gln Glu Glu Leu Asn Lys Leu Thr
130                 135                 140

Lys Thr His Tyr Ser Pro Pro Lys Phe Asp Arg Gly Leu Leu Gly Arg
145                 150                 155                 160

Leu Gln Gly Leu Lys Tyr Trp Val Arg His Phe Ala Ser Phe Tyr Val
                165                 170                 175

Leu Ser Ala Met Glu Lys Phe Ala Gly Gln Ala Val Arg Val Leu Asp
            180                 185                 190

Ser Ile Pro Asp Val Thr Pro Asp Val His Asp Lys
            195                 200
```

<210> SEQ ID NO: 26
<211> LENGTH: 95
<212> TYPE: PRT
<213> ORGANISM: Kaposi's sarcoma-associated herpes-like virus

<400> SEQUENCE: 26

```
Met Ala Pro Val His Val Leu Cys Cys Val Ser Val Leu Leu Ala Thr
 1               5                  10                  15
```

Phe Tyr Leu Thr Pro Thr Glu Ser Ala Gly Ser Leu Val Ser Tyr Thr
                20                  25                  30

Pro Asn Ser Cys Cys Tyr Gly Phe Gln Gln His Pro Pro Pro Val Gln
            35                  40                  45

Ile Leu Lys Glu Trp Tyr Pro Thr Ser Pro Ala Cys Pro Lys Pro Gly
 50                  55                  60

Val Ile Leu Leu Thr Lys Arg Gly Arg Gln Ile Cys Ala Asp Pro Ser
 65                  70                  75                  80

Lys Asn Trp Val Arg Gln Leu Met Gln Arg Leu Pro Ala Ile Ala
                85                  90                  95

<210> SEQ ID NO: 27
<211> LENGTH: 94
<212> TYPE: PRT
<213> ORGANISM: Kaposi's sarcoma-associated herpes-like virus

<400> SEQUENCE: 27

Met Asp Thr Lys Gly Ile Leu Leu Val Ala Val Leu Thr Ala Leu Leu
 1               5                  10                  15

Cys Leu Gln Ser Gly Asp Thr Leu Gly Ala Ser Trp His Arg Pro Asp
                20                  25                  30

Lys Cys Cys Leu Gly Tyr Gln Lys Arg Pro Leu Pro Gln Val Leu Leu
            35                  40                  45

Ser Ser Trp Tyr Pro Thr Ser Gln Leu Cys Ser Lys Pro Gly Val Ile
 50                  55                  60

Phe Leu Thr Lys Arg Gly Arg Gln Val Cys Ala Asp Lys Ser Lys Asp
 65                  70                  75                  80

Trp Val Lys Lys Leu Met Gln Gln Leu Pro Val Thr Ala Arg
                85                  90

<210> SEQ ID NO: 28
<211> LENGTH: 114
<212> TYPE: PRT
<213> ORGANISM: Kaposi's sarcoma-associated herpes-like virus

<400> SEQUENCE: 28

Met Trp Ser Met Cys Trp Val Leu Arg Ala His Leu Gly Leu Leu Phe
 1               5                  10                  15

Trp Val Ala Val Ile Glu Leu Cys Ala Ala Ser Gly Pro Ala Thr Ile
                20                  25                  30

Met Ala Ser Asp Cys Cys Glu Asn Ser Leu Ser Ser Ala Arg Leu Pro
            35                  40                  45

Pro Asp Lys Leu Ile Cys Gly Trp Tyr Trp Thr Ser Thr Val Tyr Cys
 50                  55                  60

Arg Gln Lys Ala Val Ile Phe Val Thr His Ser Gly Arg Lys Val Cys
 65                  70                  75                  80

Gly Ser Pro Ala Lys Arg Arg Thr Arg Leu Leu Met Glu Lys His Thr
                85                  90                  95

Glu Ile Pro Leu Ala Lys Arg Val Ala Leu Arg Ala Gly Lys Gly Leu
            100                 105                 110

Cys Pro

<210> SEQ ID NO: 29
<211> LENGTH: 256
<212> TYPE: PRT
<213> ORGANISM: Kaposi's sarcoma-associated herpes-like virus -continued

```
<400> SEQUENCE: 29

Met Ala Ser Lys Asp Val Glu Glu Gly Val Glu Gly Pro Ile Cys Trp
1               5                   10                  15

Ile Cys Arg Glu Glu Val Gly Asn Glu Gly Ile His Pro Cys Ala Cys
                20                  25                  30

Thr Gly Glu Leu Asp Val Val His Pro Gln Cys Leu Ser Thr Trp Leu
            35                  40                  45

Thr Val Ser Arg Asn Thr Ala Cys Gln Met Cys Arg Val Ile Tyr Arg
        50                  55                  60

Thr Arg Thr Gln Trp Arg Ser Arg Leu Asn Leu Trp Pro Glu Met Glu
65                  70                  75                  80

Arg Gln Glu Ile Phe Glu Leu Phe Leu Leu Met Ser Val Val Val Ala
                85                  90                  95

Gly Leu Val Gly Val Ala Leu Cys Thr Trp Thr Leu Leu Val Ile Leu
                100                 105                 110

Thr Ala Pro Ala Gly Thr Phe Ser Pro Gly Ala Val Leu Gly Phe Leu
            115                 120                 125

Cys Phe Phe Gly Phe Tyr Gln Ile Phe Ile Val Phe Ala Phe Gly Gly
    130                 135                 140

Ile Cys Arg Val Ser Gly Thr Val Arg Ala Leu Tyr Ala Ala Asn Asn
145                 150                 155                 160

Thr Arg Val Thr Val Leu Pro Tyr Arg Pro Arg Arg Pro Thr Ala
                165                 170                 175

Asn Glu Asp Asn Ile Glu Leu Thr Val Leu Val Gly Pro Ala Gly Gly
            180                 185                 190

Thr Asp Glu Glu Pro Thr Asp Glu Ser Ser Gly Asp Val Ala Ser
        195                 200                 205

Gly Asp Lys Glu Arg Asp Gly Ser Ser Gly Asp Glu Pro Asp Gly Gly
    210                 215                 220

Pro Asn Asp Arg Ala Gly Leu Arg Gly Thr Ala Arg Thr Asp Leu Cys
225                 230                 235                 240

Ala Pro Thr Lys Lys Pro Val Arg Lys Asn His Pro Lys Asn Asn Gly
                245                 250                 255

<210> SEQ ID NO: 30
<211> LENGTH: 333
<212> TYPE: PRT
<213> ORGANISM: Kaposi's sarcoma-associated herpes-like virus

<400> SEQUENCE: 30

Met Glu Asp Glu Asp Val Pro Val Cys Trp Ile Cys Asn Glu Glu Leu
1               5                   10                  15

Gly Asn Glu Arg Phe Arg Ala Cys Gly Cys Thr Gly Glu Leu Glu Asn
                20                  25                  30

Val His Arg Ser Cys Leu Ser Thr Trp Leu Thr Ile Ser Arg Asn Thr
            35                  40                  45

Ala Cys Gln Ile Cys Gly Val Val Tyr Asn Thr Arg Val Val Trp Arg
        50                  55                  60

Pro Leu Arg Glu Met Thr Leu Leu Pro Arg Leu Thr Tyr Gln Glu Gly
65                  70                  75                  80

Leu Glu Leu Ile Val Phe Ile Phe Ile Met Thr Leu Gly Ala Ala Gly
                85                  90                  95

Leu Ala Ala Ala Thr Trp Val Trp Leu Tyr Ile Val Gly Gly His Asp
                100                 105                 110
```

-continued

```
Pro Glu Ile Asp His Val Ala Ala Ala Tyr Val Phe Val
        115                 120                 125

Phe Tyr Gln Leu Phe Val Val Phe Gly Leu Gly Ala Phe His Met
        130                 135                 140

Met Arg His Val Gly Arg Ala Tyr Ala Ala Val Asn Thr Arg Val Glu
145                 150                 155                 160

Val Phe Pro Tyr Arg Pro Arg Pro Thr Ser Pro Glu Cys Ala Val Glu
                165                 170                 175

Glu Ile Glu Leu Gln Glu Ile Leu Pro Arg Gly Asp Asn Gln Asp Glu
            180                 185                 190

Glu Gly Pro Ala Gly Ala Ala Pro Gly Asp Gln Asn Gly Pro Ala Gly
        195                 200                 205

Ala Ala Pro Gly Asp Gln Asp Gly Pro Ala Asp Gly Ala Pro Val His
    210                 215                 220

Arg Asp Ser Glu Glu Ser Val Asp Glu Ala Ala Gly Tyr Lys Glu Ala
225                 230                 235                 240

Gly Glu Pro Thr His Asn Asp Gly Arg Asp Asn Val Glu Pro Thr
                245                 250                 255

Ala Val Gly Cys Asp Cys Asn Asn Leu Gly Ala Glu Arg Tyr Arg Ala
            260                 265                 270

Thr Tyr Cys Gly Tyr Val Gly Ala Gln Ser Gly Asp Gly Ala Tyr
        275                 280                 285

Ser Val Ser Cys His Asn Lys Ala Gly Pro Ser Ser Leu Val Asp Ile
    290                 295                 300

Leu Pro Gln Gly Leu Pro Gly Gly Tyr Gly Ser Met Gly Val Ile
305                 310                 315                 320

Arg Lys Arg Ser Ala Val Ser Ser Ala Leu Met Phe His
                325                 330

<210> SEQ ID NO: 31
<211> LENGTH: 294
<212> TYPE: PRT
<213> ORGANISM: Herpes simplex

<400> SEQUENCE: 31

Met Ser Thr His Thr Glu Glu Gln His Gly Glu His Gln Tyr Leu Ser
1               5                   10                  15

Gln Val Gln His Ile Leu Asn Tyr Gly Ser Phe Lys Asn Asp Arg Thr
            20                  25                  30

Gly Thr Gly Thr Leu Ser Ile Phe Gly Thr Gln Ser Arg Phe Ser Leu
        35                  40                  45

Glu Asn Glu Phe Pro Leu Leu Thr Thr Lys Arg Val Phe Trp Arg Gly
    50                  55                  60

Val Val Glu Glu Leu Leu Trp Phe Ile Arg Gly Ser Thr Asp Ser Lys
65                  70                  75                  80

Glu Leu Ser Ala Ala Gly Val His Ile Trp Asp Ala Asn Gly Ser Arg
                85                  90                  95

Ser Phe Leu Asp Lys Leu Gly Phe Tyr Asp Arg Asp Glu Gly Asp Leu
            100                 105                 110

Gly Pro Val Tyr Gly Phe Gln Trp Arg His Phe Gly Ala Glu Tyr Lys
        115                 120                 125

Gly Val Gly Arg Asp Tyr Lys Gly Glu Gly Val Asp Gln Leu Lys Gln
    130                 135                 140

Leu Ile Asp Thr Ile Lys Thr Asn Pro Thr Asp Arg Arg Met Leu Met
145                 150                 155                 160
```

Cys Ala Trp Asn Val Ser Asp Ile Pro Lys Met Val Leu Pro Pro Cys
                165                 170                 175

His Val Leu Ser Gln Phe Tyr Val Cys Asp Gly Lys Leu Ser Cys Gln
            180                 185                 190

Leu Tyr Gln Arg Ser Ala Asp Met Gly Leu Gly Val Pro Phe Asn Ile
        195                 200                 205

Ala Ser Tyr Ser Leu Leu Thr Cys Met Ile Ala His Val Thr Asn Leu
    210                 215                 220

Val Pro Gly Glu Phe Ile His Thr Ile Gly Asp Ala His Ile Tyr Val
225                 230                 235                 240

Asp His Ile Asp Ala Leu Lys Met Gln Leu Thr Arg Thr Pro Arg Pro
                245                 250                 255

Phe Pro Thr Leu Arg Phe Ala Arg Asn Val Ser Cys Ile Asp Asp Phe
            260                 265                 270

Lys Ala Asp Asp Ile Ile Leu Glu Asn Tyr Asn Pro His Pro Ile Ile
        275                 280                 285

Lys Met His Met Ala Val
290

<210> SEQ ID NO: 32
<211> LENGTH: 290
<212> TYPE: PRT
<213> ORGANISM: H. ateles

<400> SEQUENCE: 32

Met Glu Glu Leu His Ala Glu His Gln Tyr Leu Ser Gln Val Lys His
1               5                   10                  15

Ile Leu Asn Cys Gly Asn Phe Lys His Asp Arg Thr Gly Val Gly Thr
            20                  25                  30

Leu Ser Val Phe Gly Met Gln Ser Arg Tyr Ser Leu Glu Lys Asp Phe
        35                  40                  45

Pro Leu Leu Thr Thr Lys Arg Val Phe Trp Arg Gly Val Val Glu Glu
    50                  55                  60

Leu Leu Trp Phe Ile Arg Gly Ser Thr Asp Ser Lys Glu Leu Ala Ala
65                  70                  75                  80

Ser Gly Val His Ile Trp Asp Ala Asn Gly Ser Arg Ser Tyr Leu Asp
                85                  90                  95

Lys Leu Gly Leu Phe Asp Arg Glu Glu Gly Asp Leu Gly Pro Val Tyr
            100                 105                 110

Gly Phe Gln Trp Arg His Phe Gly Ala Glu Tyr Gln Gly Leu Lys His
        115                 120                 125

Asn Tyr Gly Gly Glu Gly Val Asp Gln Leu Lys Gln Ile Ile Asn Thr
    130                 135                 140

Ile His Thr Asn Pro Thr Asp Arg Arg Met Leu Met Cys Ala Trp Asn
145                 150                 155                 160

Val Leu Asp Val Pro Lys Met Ala Leu Pro Pro Cys His Val Leu Ser
                165                 170                 175

Gln Phe Tyr Val Cys Asp Gly Lys Leu Ser Cys Gln Leu Tyr Gln Arg
            180                 185                 190

Ser Ala Asp Met Gly Leu Gly Val Pro Phe Asn Ile Ala Ser Tyr Ser
        195                 200                 205

Leu Leu Thr Cys Met Ile Ala His Val Ile Asp Leu Val Pro Gly Glu
    210                 215                 220

Phe Ile His Thr Leu Gly Asp Ala His Val Tyr Val Asn His Val Asp
225                 230                 235                 240

```
Ala Leu Thr Glu Gln Leu Thr Arg Thr Pro Arg Pro Phe Pro Thr Leu
                245                 250                 255

Lys Phe Ala Arg Lys Val Ala Ser Ile Asp Asp Phe Lys Ala Asn Asp
            260                 265                 270

Ile Ile Leu Glu Asn Tyr Asn Pro Tyr Pro Ser Ile Lys Met Pro Met
        275                 280                 285

Ala Val
    290

<210> SEQ ID NO: 33
<211> LENGTH: 301
<212> TYPE: PRT
<213> ORGANISM: Varicella-zoster virus

<400> SEQUENCE: 33

Met Gly Asp Leu Ser Cys Trp Thr Lys Val Pro Gly Phe Thr Leu Thr
1               5                  10                  15

Gly Glu Leu Gln Tyr Leu Lys Gln Val Asp Asp Ile Leu Arg Tyr Gly
            20                  25                  30

Val Arg Lys Arg Asp Arg Thr Gly Ile Gly Thr Leu Ser Leu Phe Gly
        35                  40                  45

Met Gln Ala Arg Tyr Asn Leu Arg Asn Glu Phe Pro Leu Leu Thr Thr
    50                  55                  60

Lys Arg Val Phe Trp Arg Ala Val Val Glu Glu Leu Leu Trp Phe Ile
65                  70                  75                  80

Arg Gly Ser Thr Asp Ser Lys Glu Leu Ala Ala Lys Asp Ile His Ile
                85                  90                  95

Trp Asp Ile Tyr Gly Ser Ser Lys Phe Leu Asn Arg Asn Gly Phe His
            100                 105                 110

Lys Arg His Thr Gly Asp Leu Gly Pro Ile Tyr Gly Phe Gln Trp Arg
        115                 120                 125

His Phe Gly Ala Glu Tyr Lys Asp Cys Gln Ser Asn Tyr Leu Gln Gln
    130                 135                 140

Gly Ile Asp Gln Leu Gln Thr Val Ile Asp Thr Ile Lys Thr Asn Pro
145                 150                 155                 160

Glu Ser Arg Arg Met Ile Ile Ser Ser Trp Asn Pro Lys Asp Ile Pro
                165                 170                 175

Leu Met Val Leu Pro Pro Cys His Thr Leu Cys Gln Phe Tyr Val Ala
            180                 185                 190

Asn Gly Glu Leu Ser Cys Gln Val Tyr Gln Arg Ser Gly Asp Met Gly
        195                 200                 205

Leu Gly Val Pro Phe Asn Ile Ala Gly Tyr Ala Leu Leu Thr Tyr Ile
    210                 215                 220

Val Ala His Val Thr Gly Leu Lys Thr Gly Asp Leu Ile His Thr Met
225                 230                 235                 240

Gly Asp Ala His Ile Tyr Leu Asn His Ile Asp Ala Leu Lys Val Gln
                245                 250                 255

Leu Ala Arg Ser Pro Lys Pro Phe Pro Cys Leu Lys Ile Ile Arg Asn
            260                 265                 270

Val Thr Asp Ile Asn Asp Phe Lys Trp Asp Asp Phe Gln Leu Asp Gly
        275                 280                 285

Tyr Asn Pro His Pro Pro Leu Lys Met Glu Met Ala Leu
    290                 295                 300
```

<210> SEQ ID NO: 34
<211> LENGTH: 312
<212> TYPE: PRT
<213> ORGANISM: Homo sapiens

<400> SEQUENCE: 34

```
Pro Val Ala Gly Ser Glu Leu Pro Arg Arg Pro Leu Pro Pro Ala Ala
1               5                   10                  15

Gln Glu Arg Asp Ala Glu Pro Arg Pro Pro His Pro Glu Leu Gln Tyr
            20                  25                  30

Leu Gly Gln Ile Gln His Ile Leu Arg Cys Gly Val Arg Lys Asp Asp
        35                  40                  45

Arg Thr Gly Thr Gly Thr Leu Ser Val Phe Gly Met Gln Ala Arg Tyr
    50                  55                  60

Ser Leu Arg Asp Glu Phe Pro Leu Leu Thr Thr Lys Arg Val Phe Trp
65                  70                  75                  80

Lys Gly Val Leu Glu Glu Leu Leu Trp Phe Ile Lys Gly Ser Thr Asn
                85                  90                  95

Ala Lys Glu Leu Ser Ser Lys Gly Val Lys Ile Trp Asp Ala Asn Gly
            100                 105                 110

Ser Arg Asp Phe Leu Asp Ser Leu Gly Phe Ser Thr Arg Glu Glu Gly
        115                 120                 125

Asp Leu Gly Pro Val Tyr Gly Phe Gln Trp Arg His Phe Gly Ala Glu
    130                 135                 140

Tyr Arg Asp Met Glu Ser Asp Tyr Ser Gly Gln Gly Val Asp Gln Leu
145                 150                 155                 160

Gln Arg Val Ile Asp Thr Ile Lys Thr Asn Pro Asp Asp Arg Arg Ile
                165                 170                 175

Ile Met Cys Ala Trp Asn Pro Arg Asp Leu Pro Leu Met Ala Leu Pro
            180                 185                 190

Pro Cys His Ala Leu Cys Gln Phe Tyr Val Val Asn Ser Glu Leu Ser
        195                 200                 205

Cys Gln Leu Tyr Gln Arg Ser Gly Asp Met Gly Leu Gly Val Pro Phe
    210                 215                 220

Asn Ile Ala Ser Tyr Ala Leu Leu Thr Tyr Met Ile Ala His Ile Thr
225                 230                 235                 240

Gly Leu Lys Pro Gly Asp Phe Ile His Thr Leu Gly Asp Ala His Ile
                245                 250                 255

Tyr Leu Asn His Ile Glu Pro Leu Lys Ile Gln Leu Gln Arg Glu Pro
            260                 265                 270

Arg Pro Phe Pro Lys Leu Arg Ile Leu Arg Lys Val Glu Lys Ile Asp
        275                 280                 285

Asp Phe Lys Ala Glu Asp Phe Gln Ile Glu Gly Tyr Asn Pro His Pro
    290                 295                 300

Thr Ile Lys Met Glu Met Ala Val
305                 310
```

<210> SEQ ID NO: 35
<211> LENGTH: 187
<212> TYPE: PRT
<213> ORGANISM: Herpes simplex

<400> SEQUENCE: 35

```
Met Val Gln Ala Leu Asn Cys Ile Val Ala Val Ala Gln Asn Met Gly
1               5                   10                  15
```

-continued

Ile Gly Lys Gln Gly Asn Leu Pro Trp Pro Arg Leu Met Asn Asp Phe
            20                  25                  30

Lys His Phe Gln Arg Met Thr Thr Thr Ser Ser Val Pro Asp Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Val Val Leu Ser Lys Glu Leu
65                  70                  75                  80

Lys Glu Leu Pro His Arg Ala His Phe Leu Ala Lys Ser Leu Asp Asp
                85                  90                  95

Ala Leu Lys Leu Thr Glu Gln Pro Glu Leu Ala Asn Lys Val Asp Met
            100                 105                 110

Val Trp Ile Ile Gly Gly Ser Ser Val Tyr Lys Glu Ala Met Ser Tyr
        115                 120                 125

Pro Cys Asp Leu Lys Leu Phe Val Thr Arg Ile Met Gln Asp Phe Glu
    130                 135                 140

Cys Asp Thr Phe Phe Pro Glu Phe Asp Leu Glu Lys Tyr Lys Leu Leu
145                 150                 155                 160

Ile Glu Tyr Pro Ser Val Leu Ser Asn Val Gln Glu Lys Ser Ile
                165                 170                 175

Lys Tyr Lys Phe Glu Val Tyr Glu Lys Asn His
            180                 185

<210> SEQ ID NO: 36
<211> LENGTH: 186
<212> TYPE: PRT
<213> ORGANISM: Homo sapiens

<400> SEQUENCE: 36

Val Gly Ser Leu Asn Cys Ile Val Ala Val Ser Gln Asn Met Gly Ile
1               5                   10                  15

Gly Lys Asn Gly Asp Leu Pro Trp Pro Leu Arg Asn Glu Phe Arg
            20                  25                  30

Tyr Phe Gln Arg Met Ile Thr Thr Ser Ser Val Glu Gly Lys Gln Asn
        35                  40                  45

Leu Val Ile Met Gly Lys Lys Ile Trp Phe Ser Ile Pro Glu Lys Asn
    50                  55                  60

Arg Pro Leu Lys Gly Arg Ile Asn Leu Val Leu Ser Arg Glu Leu Lys
65                  70                  75                  80

Glu Pro Pro Gln Gly Ala His Phe Leu Ser Arg Ser Leu Asp Asp Ala
                85                  90                  95

Leu Lys Leu Thr Glu Gln Pro Glu Leu Ala Asn Lys Val Asp Met Val
            100                 105                 110

Trp Ile Val Gly Gly Ser Ser Val Tyr Lys Glu Ala Met Asn His Pro
        115                 120                 125

Gly His Leu Lys Leu Phe Val Thr Arg Ile Met Gln Asp Phe Glu Ser
    130                 135                 140

Asp Thr Phe Phe Pro Glu Ile Asp Leu Glu Lys Tyr Lys Leu Leu Pro
145                 150                 155                 160

Glu Tyr Pro Gly Val Leu Ser Asp Val Gln Glu Glu Lys Gly Ile Lys
                165                 170                 175

Tyr Lys Phe Glu Val Tyr Glu Lys Asn Asp
            180                 185

```
<210> SEQ ID NO: 37
<211> LENGTH: 186
<212> TYPE: PRT
<213> ORGANISM: Pig

<400> SEQUENCE: 37

Val Arg Pro Leu Asn Cys Ile Val Ala Val Ser Gln Asn Met Gly Ile
1               5                   10                  15

Gly Lys Asn Gly Asp Leu Pro Trp Pro Leu Arg Asn Glu Tyr Lys
            20                  25                  30

Tyr Phe Gln Arg Met Thr Thr Thr Ser Ser Val Glu Gly Lys Gln Asn
        35                  40                  45

Leu Val Ile Met Gly Arg Lys Thr Trp Phe Ser Ile Pro Glu Lys Asn
    50                  55                  60

Arg Pro Leu Lys Asp Arg Ile Asn Ile Val Leu Ser Arg Glu Leu Lys
65                  70                  75                  80

Glu Pro Pro Gln Gly Ala His Phe Leu Ala Lys Ser Leu Asp Asp Ala
                85                  90                  95

Leu Lys Leu Thr Glu Gln Pro Glu Leu Lys Asp Lys Val Asp Met Val
            100                 105                 110

Trp Ile Val Gly Gly Ser Ser Val Tyr Lys Glu Ala Met Asn Lys Pro
        115                 120                 125

Gly His Ile Arg Leu Phe Val Thr Arg Ile Met Lys Glu Phe Glu Ser
    130                 135                 140

Asp Thr Phe Phe Pro Glu Ile Asp Leu Glu Lys Tyr Lys Leu Leu Ser
145                 150                 155                 160

Glu Cys Ser Gly Val Pro Ser Asp Val Gln Glu Glu Lys Gly Ile Lys
                165                 170                 175

Tyr Lys Phe Glu Val Tyr Glu Lys Asn Asn
            180                 185

<210> SEQ ID NO: 38
<211> LENGTH: 182
<212> TYPE: PRT
<213> ORGANISM: Drosophila

<400> SEQUENCE: 38

Met Leu Arg Phe Asn Leu Ile Val Ala Val Cys Glu Asn Phe Gly Ile
1               5                   10                  15

Gly Ile Arg Gly Asp Leu Pro Trp Arg Ile Lys Ser Glu Leu Lys Tyr
            20                  25                  30

Phe Ser Arg Thr Thr Lys Arg Thr Ser Asp Pro Thr Lys Gln Asn Ala
        35                  40                  45

Val Val Met Gly Arg Lys Thr Tyr Phe Gly Val Pro Glu Ser Lys Arg
    50                  55                  60

Pro Leu Pro Asp Arg Leu Asn Ile Val Leu Ser Thr Thr Leu Gln Glu
65                  70                  75                  80

Ser Asp Leu Pro Lys Gly Val Leu Leu Cys Pro Asn Leu Glu Thr Ala
                85                  90                  95

Met Lys Ile Leu Glu Glu Gln Asn Glu Val Glu Asn Ile Trp Ile Val
            100                 105                 110

Gly Gly Ser Gly Val Tyr Glu Glu Ala Met Ala Ser Pro Arg Cys His
        115                 120                 125

Arg Leu Tyr Ile Thr Gln Ile Met Gln Lys Phe Asp Cys Asp Thr Phe
    130                 135                 140
```

-continued

```
Phe Pro Ala Ile Pro Asp Ser Phe Arg Glu Val Ala Pro Asp Ser Asp
145                 150                 155                 160

Met Pro Leu Gly Val Gln Glu Glu Asn Gly Ile Lys Phe Glu Tyr Lys
                165                 170                 175

Ile Leu Glu Lys His Ser
            180

<210> SEQ ID NO: 39
<211> LENGTH: 93
<212> TYPE: PRT
<213> ORGANISM: Homo sapiens

<400> SEQUENCE: 39

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

<210> SEQ ID NO: 40
<211> LENGTH: 90
<212> TYPE: PRT
<213> ORGANISM: Homo sapiens

<400> SEQUENCE: 40

Met Lys Val Ser Ala Ala Arg Leu Ala Val Ile Leu Ile Ala Thr Ala
1               5                   10                  15

Leu Cys Ala Pro Ala Ser Ala Ser Pro Tyr Ser Ser Asp Thr Thr Pro
                20                  25                  30

Cys Cys Phe Ala Tyr Ile Ala Arg Pro Leu Pro Arg Ala His Ile Lys
            35                  40                  45

Glu Tyr Phe Tyr Thr Ser Gly Lys Cys Ser Asn Pro Ala Val Val Phe
    50                  55                  60

Val Thr Arg Lys Asn Arg Gln Val Cys Ala Asn Pro Glu Lys Lys Trp
65                  70                  75                  80

Val Arg Glu Tyr Ile Asn Ser Leu Glu Ser
                85                  90

<210> SEQ ID NO: 41
<211> LENGTH: 92
<212> TYPE: PRT
<213> ORGANISM: Homo sapiens

<400> SEQUENCE: 41

Met Lys Leu Cys Val Thr Val Leu Ser Leu Leu Met Leu Val Ala Ala
1               5                   10                  15

Phe Cys Ser Pro Ala Leu Ser Ala Pro Met Gly Ser Asp Pro Pro Thr
                20                  25                  30

Ala Cys Cys Phe Ser Tyr Thr Ala Arg Lys Leu Pro Arg Asn Phe Val
            35                  40                  45
```

```
Val Asp Tyr Tyr Glu Thr Ser Ser Leu Cys Ser Gln Pro Ala Val Val
    50                  55                  60

Phe Gln Thr Lys Arg Gly Lys Gln Val Cys Ala Asp Pro Ser Glu Ser
65                  70                  75                  80

Trp Val Gln Glu Tyr Val Tyr Asp Leu Glu Leu Asn
                85                  90

<210> SEQ ID NO: 42
<211> LENGTH: 147
<212> TYPE: PRT
<213> ORGANISM: Mus musculus

<400> SEQUENCE: 42

Met Gln Val Pro Val Met Leu Leu Gly Leu Leu Phe Thr Val Ala Gly
1               5                   10                  15

Trp Ser Ile His Val Leu Ser Gln Pro Asp Ala Val Asn Ala Pro Leu
                20                  25                  30

Thr Cys Cys Tyr Ser Phe Thr Ser Lys Met Ile Pro Met Ser Arg Leu
            35                  40                  45

Glu Ser Tyr Lys Arg Thr Ser Ser Arg Cys Pro Lys Glu Ala Val Val
    50                  55                  60

Phe Val Thr Lys Leu Lys Arg Glu Val Cys Ala Asp Pro Lys Lys Glu
65                  70                  75                  80

Trp Val Gln Thr Tyr Ile Lys Asn Leu Asp Arg Asn Gln Met Arg Ser
                85                  90                  95

Glu Pro Thr Thr Leu Phe Lys Thr Ala Ser Ala Leu Arg Ser Ser Ala
            100                 105                 110

Pro Leu Asn Val Lys Leu Thr Arg Lys Ser Glu Ala Asn Ala Ser Thr
        115                 120                 125

Thr Phe Ser Thr Thr Ser Ser Thr Ser Val Gly Val Thr Ser Val
    130                 135                 140

Thr Val Asn
145

<210> SEQ ID NO: 43
<211> LENGTH: 147
<212> TYPE: PRT
<213> ORGANISM: Rat

<400> SEQUENCE: 43

Met Gln Val Ser Val Thr Leu Leu Gly Leu Leu Phe Thr Val Ala Ala
1               5                   10                  15

Cys Ser Ile His Val Leu Ser Gln Arg Asp Ala Val Asn Ala Pro Leu
                20                  25                  30

Thr Cys Cys Tyr Ser Phe Thr Gly Lys Met Ile Pro Met Ser Arg Leu
            35                  40                  45

Glu Asn Tyr Lys Arg Thr Ser Ser Pro Cys Pro Lys Glu Ala Val Val
    50                  55                  60

Phe Val Thr Lys Leu Lys Arg Glu Ile Cys Ala Asp Pro Asn Lys Glu
65                  70                  75                  80

Trp Val Gln Lys Tyr Ile Arg Lys Leu Asp Gln Asn Gln Val Arg Ser
                85                  90                  95

Glu Thr Thr Val Phe Tyr Lys Ile Ala Ser Thr Leu Arg Thr Ser Ala
            100                 105                 110

Pro Leu Asn Val Asn Leu Thr His Lys Ser Glu Ala Asn Ala Ser Thr
        115                 120                 125
```

-continued

```
Leu Phe Ser Thr Thr Thr Ser Ser Thr Ser Val Glu Val Thr Ser Met
    130                 135                 140

Thr Glu Asn
145

<210> SEQ ID NO: 44
<211> LENGTH: 96
<212> TYPE: PRT
<213> ORGANISM: Homo sapiens

<400> SEQUENCE: 44

Met Lys Val Ser Ala Ala Leu Leu Trp Leu Leu Leu Ile Ala Ala Ala
  1               5                  10                  15

Phe Ser Pro Gln Gly Leu Thr Gly Pro Ala Ser Val Pro Thr Thr Cys
                 20                  25                  30

Cys Phe Asn Leu Ala Asn Arg Lys Ile Pro Leu Gln Arg Leu Glu Ser
             35                  40                  45

Tyr Arg Arg Thr Ser Gly Lys Cys Pro Gln Lys Ala Val Ile Phe Lys
         50                  55                  60

Thr Lys Leu Ala Lys Asp Ile Cys Ala Asp Pro Lys Lys Arg Trp Val
 65                  70                  75                  80

Gln Asp Ser Met Lys Tyr Leu Asp Gln Lys Ser Pro Thr Pro Lys Pro
                 85                  90                  95

<210> SEQ ID NO: 45
<211> LENGTH: 212
<212> TYPE: PRT
<213> ORGANISM: Homo sapiens

<400> SEQUENCE: 45

Met Asn Ser Phe Ser Thr Ser Ala Phe Gly Pro Val Ala Phe Ser Leu
  1               5                  10                  15

Gly Leu Leu Leu Val Leu Pro Ala Ala Phe Pro Ala Pro Val Pro Pro
                 20                  25                  30

Gly Glu Asp Ser Lys Asp Val Ala Ala Pro His Arg Gln Pro Leu Thr
             35                  40                  45

Ser Ser Glu Arg Ile Asp Lys Gln Ile Arg Tyr Ile Leu Asp Gly Ile
         50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
                115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190
```

-continued

```
Leu Ile Leu Arg Ser Phe Lys Glu Phe Leu Gln Ser Ser Leu Arg Ala
            195                 200                 205

Leu Arg Gln Met
    210

<210> SEQ ID NO: 46
<211> LENGTH: 51
<212> TYPE: PRT
<213> ORGANISM: Chlamydomonas

<400> SEQUENCE: 46

Glu Asp Ser Cys Trp Ile Cys Leu Ala Gly Ala Glu Ser Gly Leu Arg
  1               5                  10                  15

Pro Cys Arg Cys Pro Arg Ser Val His Leu Ser Cys Leu Gly Arg Trp
                 20                  25                  30

Gln Leu Gln Gln Ala Gly Arg Ser Glu Glu Gln Arg Cys Arg Phe Cys
            35                  40                  45

Thr Cys Val
    50

<210> SEQ ID NO: 47
<211> LENGTH: 59
<212> TYPE: PRT
<213> ORGANISM: C. elegans

<400> SEQUENCE: 47

Glu Lys Tyr Cys Lys Phe Cys Phe Gly Thr Glu Ser Asp Asn Ala Leu
  1               5                  10                  15

Ser Phe Val His Pro Cys Arg Cys Arg Gly Ser Ile His Trp Val His
                 20                  25                  30

His Gln Cys Leu Ala Met Trp Phe Ser Lys Ala Asn Ala Val Gln Gln
            35                  40                  45

Val Met Cys Ile Gln Cys Gln Thr Arg Tyr Gln
    50                  55

<210> SEQ ID NO: 48
<211> LENGTH: 63
<212> TYPE: PRT
<213> ORGANISM: Saccharomyces cerevisiae

<400> SEQUENCE: 48

Gly Ala Thr Cys Arg Ile Cys Arg Gly Glu Ala Thr Glu Asp Asn Pro
  1               5                  10                  15

Leu Phe His Pro Cys Lys Cys Arg Gly Ser Ile Lys Tyr Met His Glu
                 20                  25                  30

Ser Cys Leu Leu Glu Trp Val Ala Ser Lys Asn Ile Asp Ile Ser Lys
            35                  40                  45

Pro Gly Ala Asp Val Lys Cys Asp Ile Cys His Tyr Pro Ile Gln
    50                  55                  60

<210> SEQ ID NO: 49
<211> LENGTH: 55
<212> TYPE: PRT
<213> ORGANISM: C. elegans

<400> SEQUENCE: 49

Thr Val Ile Cys Arg Ile Cys Phe Asp Asn Asp Thr Ser Ser Asp Ser
  1               5                  10                  15

Leu Ile Lys Pro Cys Ser Cys Ser Gly Thr Val Ala Tyr Val His Asn
                 20                  25                  30
```

-continued

Gly Cys Leu Glu Gln Trp Val Arg Thr Thr Ser Asn Ile Gln Cys Thr
            35                  40                  45

Ile Cys Gln Asp Met Phe Glu
    50                  55

<210> SEQ ID NO: 50
<211> LENGTH: 52
<212> TYPE: PRT
<213> ORGANISM: C. elegans

<400> SEQUENCE: 50

Arg Arg Ile Cys Arg Ile Cys Gln Met His Glu Gly Asp Met Val Arg
1               5                   10                  15

Pro Cys Asp Cys Ala Gly Thr Met Gly Asp Val His Glu Glu Cys Leu
            20                  25                  30

Thr Lys Trp Val Asn Met Ser Asn Lys Lys Thr Cys Glu Ile Cys Lys
        35                  40                  45

Ser Glu Tyr Thr
    50

<210> SEQ ID NO: 51
<211> LENGTH: 53
<212> TYPE: PRT
<213> ORGANISM: swine pox virus

<400> SEQUENCE: 51

Met Asp Pro Val Cys Trp Ile Cys Lys Asp Asp Tyr Ser Ile Glu Lys
1               5                   10                  15

Asn Tyr Cys Asn Cys Lys Asn Glu Tyr Lys Val Val His Asp Glu Cys
            20                  25                  30

Met Lys Lys Trp Ile Gln Tyr Ser Arg Glu Arg Ser Cys Lys Leu Cys
        35                  40                  45

Asn Lys Glu Tyr Asn
    50

<210> SEQ ID NO: 52
<211> LENGTH: 53
<212> TYPE: PRT
<213> ORGANISM: Kaposi's sarcoma-associated herpesvirus

<400> SEQUENCE: 52

Val Pro Val Cys Trp Ile Cys Asn Glu Glu Leu Gly Asn Glu Arg Phe
1               5                   10                  15

Arg Ala Cys Gly Cys Thr Gly Glu Leu Glu Asn Val His Arg Ser Cys
            20                  25                  30

Leu Ser Thr Trp Leu Thr Ile Ser Arg Asn Thr Ala Cys Gln Ile Cys
        35                  40                  45

Gly Val Val Tyr Asn
    50

<210> SEQ ID NO: 53
<211> LENGTH: 53
<212> TYPE: PRT
<213> ORGANISM: Kaposi's sarcoma-associated herpesvirus

<400> SEQUENCE: 53

Gly Pro Ile Cys Trp Ile Cys Arg Glu Glu Ile Gly Asn Glu Gly Ile
1               5                   10                  15

His Pro Cys Ala Cys Thr Gly Glu Leu Asp Val Val His Pro Gln Cys
            20                  25                  30

-continued

Leu Ser Thr Trp Leu Thr Val Ser Arg Asn Thr Ala Cys Gln Met Cys
            35                  40                  45

Arg Val Ile Tyr Arg
        50

<210> SEQ ID NO: 54
<211> LENGTH: 53
<212> TYPE: PRT
<213> ORGANISM: Bovine herpesvirus type 4

<400> SEQUENCE: 54

Tyr Ala Glu Cys Trp Ile Cys Lys Gly Ser Glu Gly Ile Ile Asp Val
 1               5                  10                  15

Lys Tyr Cys His Cys Ile Gly Asp Leu Gln Tyr Val His Ser Glu Cys
            20                  25                  30

Leu Val His Trp Ile Arg Val Ser Gly Thr Lys Gln Cys Lys Phe Cys
            35                  40                  45

Gln Tyr Thr Tyr Ile
        50

<210> SEQ ID NO: 55
<211> LENGTH: 53
<212> TYPE: PRT
<213> ORGANISM: Bovine herpesvirus type 4

<400> SEQUENCE: 55

Gly Lys Gln Cys Trp Ile Cys Arg Asp Gly Glu Ser Leu Pro Glu Ala
 1               5                  10                  15

Arg Tyr Cys Asn Cys Tyr Gly Asp Leu Gln Tyr Cys His Glu Glu Cys
            20                  25                  30

Leu Lys Thr Trp Ile Ser Met Ser Gly Glu Lys Lys Cys Lys Phe Cys
            35                  40                  45

Gln Thr Pro Tyr Lys
        50

<210> SEQ ID NO: 56
<211> LENGTH: 50
<212> TYPE: PRT
<213> ORGANISM: Herpes simplex

<400> SEQUENCE: 56

Gln Lys Lys Cys Leu Ile Cys Cys Asn Ile Gly Glu Glu Leu Leu
 1               5                  10                  15

Gln Ala Cys Asp Cys Pro Ser Arg Val His His Thr Cys Leu Gln Ser
            20                  25                  30

His Ile Gln Cys Phe Lys Ser His Cys Thr Phe Cys Glu Lys Lys
            35                  40                  45

Tyr Lys
    50

<210> SEQ ID NO: 57
<211> LENGTH: 53
<212> TYPE: PRT
<213> ORGANISM: Homo sapiens

<400> SEQUENCE: 57

Ile Gly Gly Cys Cys Val Cys Ser Asp Glu Arg Gly Trp Ala Glu Asn
 1               5                  10                  15

Pro Leu Val Tyr Cys Asp Gly His Gly Cys Ser Val Ala Val His Gln
            20                  25                  30

-continued

Ala Cys Tyr Gly Ile Val Gln Val Pro Thr Gly Pro Trp Phe Cys Arg
              35                  40                  45

Lys Cys Glu Ser Gln
         50

<210> SEQ ID NO: 58
<211> LENGTH: 52
<212> TYPE: PRT
<213> ORGANISM: Homo sapiens

<400> SEQUENCE: 58

Arg Val Val Cys Phe Leu Cys Ala Ser Ser Gly His Val Glu Phe Val
 1               5                  10                  15

Tyr Cys Gln Val Cys Cys Glu Pro Phe His Lys Phe Cys Leu Glu Glu
             20                  25                  30

Asn Glu Arg Pro Leu Glu Asp Gln Leu Glu Asn Trp Cys Cys Arg Arg
             35                  40                  45

Cys Lys Phe Cys
         50

<210> SEQ ID NO: 59
<211> LENGTH: 47
<212> TYPE: PRT
<213> ORGANISM: Homo sapiens

<400> SEQUENCE: 59

Ser Ile Ser Cys Gln Ile Cys Glu His Ile Leu Ala Asp Pro Val Glu
 1               5                  10                  15

Thr Asn Cys Lys His Val Phe Cys Arg Val Cys Ile Leu Arg Cys Leu
             20                  25                  30

Lys Val Met Gly Ser Tyr Cys Pro Ser Cys Arg Tyr Pro Cys Phe
             35                  40                  45

<210> SEQ ID NO: 60
<211> LENGTH: 49
<212> TYPE: PRT
<213> ORGANISM: Herpes simplex

<400> SEQUENCE: 60

Gly Asp Val Cys Ala Val Cys Thr Asp Glu Ile Ala Pro His Leu Arg
 1               5                  10                  15

Cys Asp Thr Phe Pro Cys Met His Arg Phe Cys Ile Pro Cys Met Lys
             20                  25                  30

Thr Trp Asn Gln Leu Arg Asn Thr Cys Pro Leu Cys Asn Ala Lys Leu
             35                  40                  45

Val

<210> SEQ ID NO: 61
<211> LENGTH: 43
<212> TYPE: PRT
<213> ORGANISM: Homo sapiens

<400> SEQUENCE: 61

Phe Leu Arg Cys Gln Gln Cys Gln Ala Glu Ala Lys Cys Pro Lys Leu
 1               5                  10                  15

Leu Pro Cys Leu His Thr Leu Cys Ser Gly Cys Leu Glu Ala Ser Gly
             20                  25                  30

Met Gln Cys Pro Ile Cys Gln Ala Pro Trp Pro
             35                  40

```
<210> SEQ ID NO: 62
<211> LENGTH: 49
<212> TYPE: PRT
<213> ORGANISM: Homo sapiens

<400> SEQUENCE: 62

Ile Leu Glu Cys Pro Ile Cys Leu Glu Leu Ile Lys Glu Pro Val Ser
 1               5                  10                  15

Thr Lys Cys Asp His Ile Phe Cys Lys Phe Cys Met Leu Lys Leu Leu
            20                  25                  30

Asn Gln Lys Lys Gly Pro Ser Gln Cys Pro Leu Cys Lys Asn Asp Ile
        35                  40                  45

Thr
```